US010793567B2

(12) United States Patent
Fuller et al.

(10) Patent No.: US 10,793,567 B2
(45) Date of Patent: Oct. 6, 2020

(54) BICYCLIC INHIBITORS OF HISTONE DEACETYLASE

(71) Applicant: Rodin Therapeutics, Inc., Waltham, MA (US)

(72) Inventors: Nathan Oliver Fuller, Arlington, MA (US); John A. Lowe, III, Stonington, CT (US)

(73) Assignee: Rodin Therapeutics, Inc., Waltham, MA (US)

( * ) Notice: Subject to any disclaimer, the term of this patent is extended or adjusted under 35 U.S.C. 154(b) by 0 days.

(21) Appl. No.: 16/477,466

(22) PCT Filed: Jan. 11, 2018

(86) PCT No.: PCT/US2018/013262
§ 371 (c)(1),
(2) Date: Jul. 11, 2019

(87) PCT Pub. No.: WO2018/132533
PCT Pub. Date: Jul. 19, 2018

(65) Prior Publication Data
US 2019/0337953 A1 Nov. 7, 2019

Related U.S. Application Data

(60) Provisional application No. 62/555,298, filed on Sep. 7, 2017, provisional application No. 62/445,022, filed on Jan. 11, 2017.

(51) Int. Cl.
*A61K 31/519* (2006.01)
*C07D 471/04* (2006.01)
(Continued)

(52) U.S. Cl.
CPC .......... *C07D 471/04* (2013.01); *A61K 31/437* (2013.01); *A61K 31/519* (2013.01); *A61P 25/28* (2018.01); *C07D 487/04* (2013.01)

(58) Field of Classification Search
CPC .............. A61K 31/4439; A61K 31/444; A61K 31/519; C07D 471/04; C07D 487/04
(Continued)

(56) References Cited
U.S. PATENT DOCUMENTS 5,112,824 A    5/1992  Baldwin et al.
5,872,136 A    2/1999  Anthony et al.
(Continued)

FOREIGN PATENT DOCUMENTS

CN    103601718 A    2/2014
CN    103864754 A    6/2014
(Continued)

OTHER PUBLICATIONS

U.S. Appl. No. 15/741,609, filed Jan. 3, 2018, 2018-0194760, Allowed.
(Continued)

*Primary Examiner* — Jeffrey H Murray
(74) *Attorney, Agent, or Firm* — McCarter & English, LLP; Steven G. Davis; Michael J. DeGrazia

(57) ABSTRACT

Provided are compounds of the formula

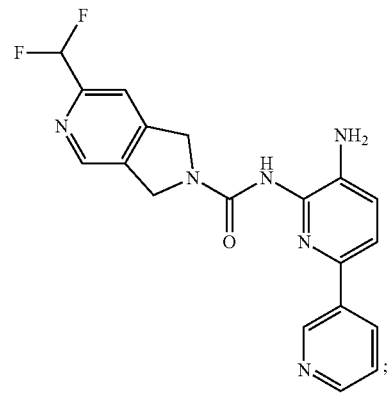

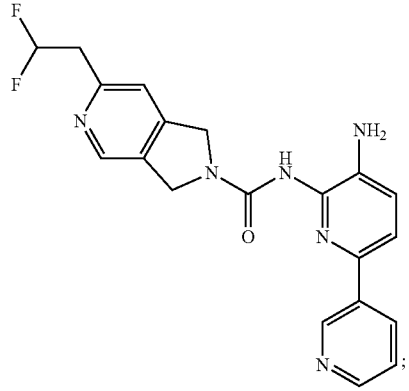

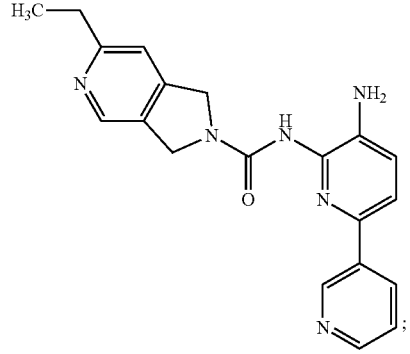

(Continued)

-continued
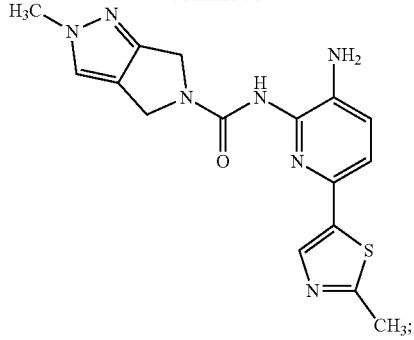
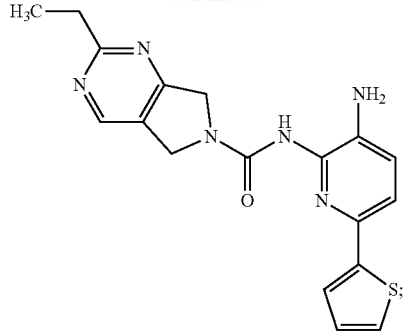
-continued
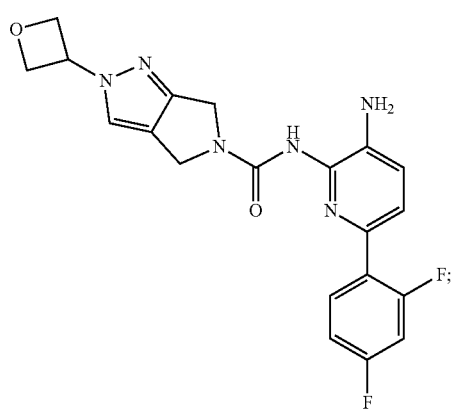
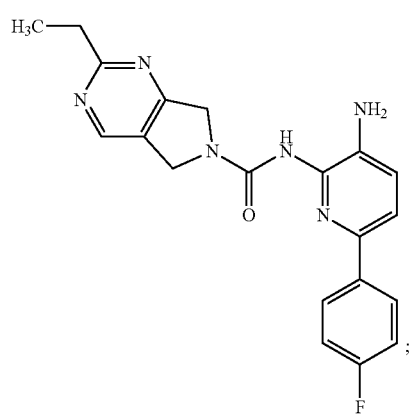
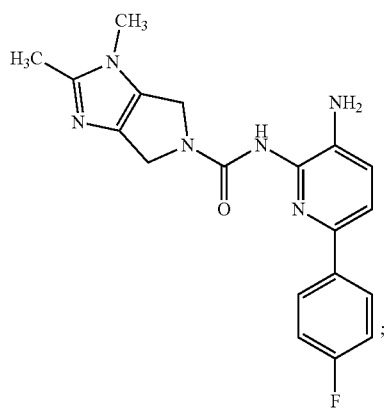
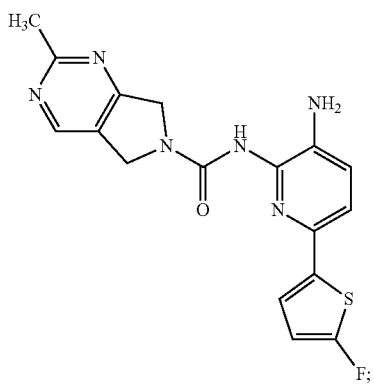
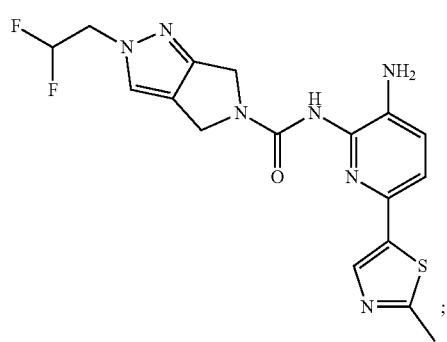
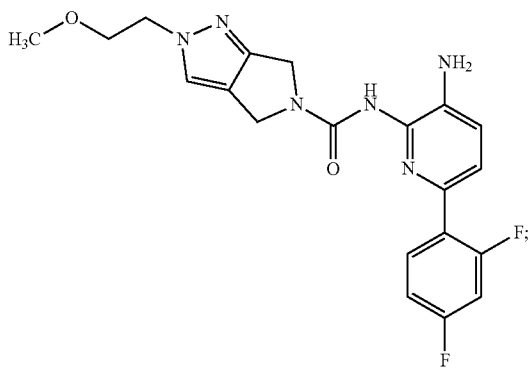

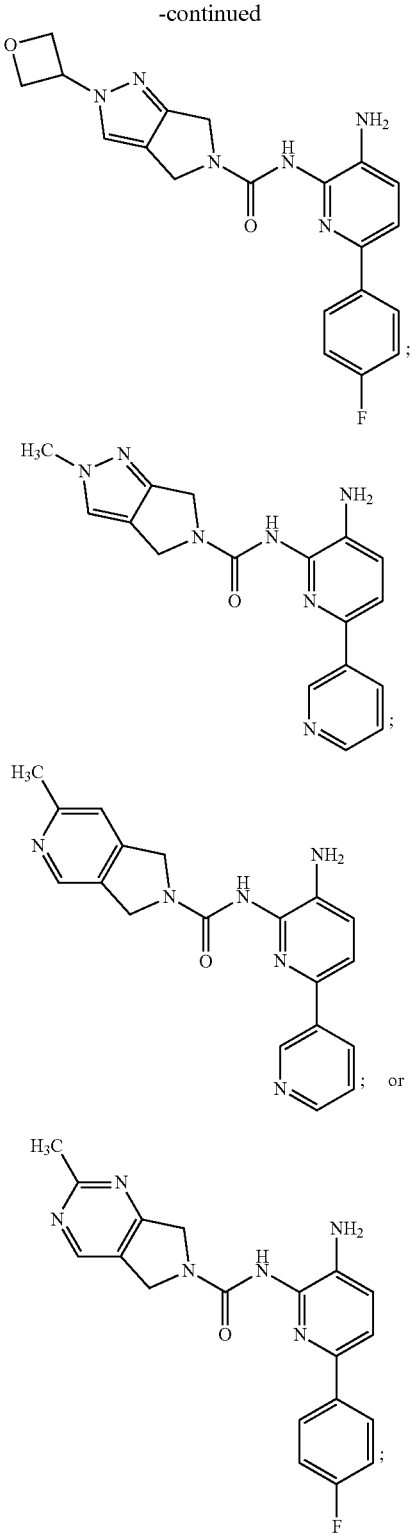

and pharmaceutically acceptable salts and composition thereof, which are useful in the treatment of conditions associated with inhibition of HDAC (e.g. HDAC2).

16 Claims, No Drawings

(51) Int. Cl.
A61P 25/28 (2006.01)
A61K 31/437 (2006.01)
C07D 487/04 (2006.01)

(58) Field of Classification Search
USPC ...... 514/265.1, 300, 303; 544/280; 546/113, 546/256, 275.7
See application file for complete search history.

(56) References Cited

U.S. PATENT DOCUMENTS

| | | |
|---|---|---|
| 7,544,695 B2 | 6/2009 | Berk et al. |
| 7,834,026 B2 | 11/2010 | Berk et al. |
| 7,863,279 B2 | 1/2011 | Even et al. |
| 7,868,205 B2 | 1/2011 | Moradei et al. |
| 7,981,874 B2 | 7/2011 | Close et al. |
| 8,349,825 B2 | 1/2013 | Mampreian et al. |
| 8,461,189 B2 | 6/2013 | Heidebrecht, Jr. et al. |
| 8,686,020 B2 | 4/2014 | Hamblett et al. |
| 8,703,959 B2 | 4/2014 | Kutose et al. |
| 8,809,544 B2 | 8/2014 | Kutose et al. |
| 8,962,849 B2 | 2/2015 | Kutose et al. |
| 8,962,850 B2 | 2/2015 | Kutose et al. |
| 8,981,107 B2 | 3/2015 | Kutose et al. |
| 9,951,069 B1 | 4/2018 | Fuller et al. |
| 10,421,756 B2 | 9/2019 | Jefson et al. |
| 2002/0183324 A1 | 12/2002 | Jacobson et al. |
| 2003/0187026 A1 | 10/2003 | Li et al. |
| 2003/0199511 A1 | 10/2003 | Li et al. |
| 2005/0025995 A1 | 2/2005 | Cheng et al. |
| 2005/0153981 A1 | 7/2005 | Li et al. |
| 2005/0245530 A1 | 11/2005 | Borzilleri et al. |
| 2006/0173050 A1 | 8/2006 | Liu et al. |
| 2006/0235028 A1 | 10/2006 | Li et al. |
| 2006/0270686 A1 | 11/2006 | Kelly et al. |
| 2007/0004741 A1 | 1/2007 | Apodaca et al. |
| 2007/0037794 A1 | 2/2007 | Ungashe et al. |
| 2007/0135437 A1 | 6/2007 | Benjamin et al. |
| 2008/0064871 A1 | 3/2008 | Hirata et al. |
| 2008/0103182 A1 | 5/2008 | Ackermann et al. |
| 2008/0132503 A1 | 6/2008 | Moradei et al. |
| 2008/0280891 A1 | 11/2008 | Kelly et al. |
| 2009/0022047 A1 | 1/2009 | Seto et al. |
| 2009/0058982 A1 | 3/2009 | Seto et al. |
| 2009/0062297 A1 | 3/2009 | Heidebrecht et al. |
| 2009/0156825 A1 | 6/2009 | Heidebrecht, Jr. et al. |
| 2009/0207712 A1 | 8/2009 | Seto et al. |
| 2009/0286782 A1 | 11/2009 | Ibrahim et al. |
| 2009/0286783 A1 | 11/2009 | Ibrahim et al. |
| 2009/0306086 A1 | 12/2009 | Ibrahim et al. |
| 2009/0306087 A1 | 12/2009 | Ibrahim et al. |
| 2010/0041670 A1 | 2/2010 | Even et al. |
| 2010/0099676 A1 | 4/2010 | Endoh et al. |
| 2010/0310500 A1 | 12/2010 | Graupe et al. |
| 2011/0009365 A1 | 1/2011 | Dubois et al. |
| 2011/0021494 A1 | 1/2011 | Maier et al. |
| 2011/0105472 A1 | 5/2011 | Greul et al. |
| 2011/0118248 A1 | 5/2011 | Ungashe et al. |
| 2011/0224155 A1 | 9/2011 | Tachdjian et al. |
| 2012/0184572 A1 | 7/2012 | Song et al. |
| 2012/0295881 A1 | 11/2012 | Lange et al. |
| 2013/0210880 A1 | 8/2013 | Amberg et al. |
| 2013/0331382 A1 | 12/2013 | Hubbard et al. |
| 2014/0128391 A1 | 5/2014 | van Duzer et al. |
| 2014/0187780 A1 | 7/2014 | Kim et al. |
| 2014/0329684 A1 | 11/2014 | Muller et al. |
| 2014/0364605 A1 | 12/2014 | Li et al. |
| 2015/0057300 A1 | 2/2015 | Tafesse et al. |
| 2015/0094329 A1 | 4/2015 | Nokura et al. |
| 2015/0266866 A1 | 9/2015 | Conn et al. |
| 2015/0322076 A1 | 11/2015 | Chen et al. |
| 2016/0096833 A1 | 4/2016 | Emmitte et al. |
| 2018/0009818 A1 | 1/2018 | Miyazaki et al. |
| 2018/0194760 A1 | 7/2018 | Jefson et al. |

(56) References Cited

U.S. PATENT DOCUMENTS

| | | |
|---|---|---|
| 2018/0194769 A1 | 7/2018 | Jefson et al. |
| 2018/0215759 A1 | 8/2018 | Fuller et al. |

FOREIGN PATENT DOCUMENTS

| | | |
|---|---|---|
| CN | 105777632 A | 7/2016 |
| CN | 106946890 A | 7/2017 |
| DE | 4212748 A1 | 10/1993 |
| EP | 2712655 A1 | 4/2014 |
| GB | 2515785 A | 1/2015 |
| GB | 2516303 A | 1/2015 |
| JP | H11-049676 A | 2/1999 |
| JP | H11-209366 A | 8/1999 |
| JP | 2003-192673 A | 7/2003 |
| JP | 2003-300940 A | 10/2003 |
| JP | 2008-094847 A | 4/2008 |
| JP | 2008-179067 A | 8/2008 |
| JP | 2008-179068 A | 8/2008 |
| JP | 2009-023986 A | 2/2009 |
| JP | 2009-514858 A | 4/2009 |
| JP | 2009-516743 A | 4/2009 |
| JP | 2009-523725 A | 6/2009 |
| JP | 2009-209090 A | 9/2009 |
| JP | 2009-536615 A | 10/2009 |
| JP | 2010-524908 A | 7/2010 |
| JP | 2010-531358 A | 9/2010 |
| JP | 2012-107001 A | 6/2012 |
| JP | 2012-529435 A | 11/2012 |
| JP | 2013-020223 A | 1/2013 |
| JP | 5-208961 B2 | 6/2013 |
| JP | 2014-101353 A | 6/2014 |
| JP | 2014-523857 A | 9/2014 |
| WO | 1992/01675 A2 | 2/1992 |
| WO | 1996/11929 A1 | 4/1996 |
| WO | 1996/11930 A1 | 4/1996 |
| WO | 1996/18617 A1 | 6/1996 |
| WO | 1996/21660 A1 | 7/1996 |
| WO | 1996/23783 A1 | 8/1996 |
| WO | 1996/32938 A1 | 10/1996 |
| WO | 1997/08167 A1 | 3/1997 |
| WO | 1997/15557 A1 | 5/1997 |
| WO | 1997/36901 A1 | 10/1997 |
| WO | 1998/55472 A1 | 12/1998 |
| WO | 1999/65897 A1 | 12/1999 |
| WO | 2000/002860 A1 | 1/2000 |
| WO | 2000/055114 A1 | 9/2000 |
| WO | 2001/021597 A1 | 3/2001 |
| WO | 2002/014315 A2 | 2/2002 |
| WO | 2002/020011 A2 | 3/2002 |
| WO | 2002/026708 A1 | 4/2002 |
| WO | 2002/032900 A2 | 4/2002 |
| WO | 2002/046172 A2 | 6/2002 |
| WO | 2002/053160 A1 | 7/2002 |
| WO | 2002/068417 A2 | 9/2002 |
| WO | 2002/089738 A2 | 11/2002 |
| WO | 2003/042190 A1 | 5/2003 |
| WO | 2003/051366 A2 | 6/2003 |
| WO | 2003/055447 A2 | 7/2003 |
| WO | 2003/059269 A2 | 7/2003 |
| WO | 2003/062224 A1 | 7/2003 |
| WO | 2003/095437 A1 | 11/2003 |
| WO | 2004/000318 A2 | 12/2003 |
| WO | 2004/000820 A2 | 12/2003 |
| WO | 2004/016597 A2 | 2/2004 |
| WO | 2004/045518 A2 | 6/2004 |
| WO | 2004/071426 A2 | 8/2004 |
| WO | 2004/072033 A2 | 8/2004 |
| WO | 2005/009988 A1 | 2/2005 |
| WO | 2005/014580 A1 | 2/2005 |
| WO | 2005/016862 A1 | 2/2005 |
| WO | 2005/079802 A1 | 9/2005 |
| WO | 2005/095386 A1 | 10/2005 |
| WO | 2005/097740 A1 | 10/2005 |
| WO | 2005/121093 A1 | 12/2005 |
| WO | 2006/019833 A1 | 2/2006 |
| WO | 2006/044975 A2 | 4/2006 |
| WO | 2006/051311 A1 | 5/2006 |
| WO | 2006/065479 A2 | 6/2006 |
| WO | 2006/067445 A2 | 6/2006 |
| WO | 2006/067446 A1 | 6/2006 |
| WO | 2006/076644 A2 | 7/2006 |
| WO | 2006/077168 A1 | 7/2006 |
| WO | 2006/080884 A1 | 8/2006 |
| WO | 2006/084017 A2 | 8/2006 |
| WO | 2006/120133 A2 | 11/2006 |
| WO | 2006/128129 A1 | 11/2006 |
| WO | 2006/128172 A2 | 11/2006 |
| WO | 2006/135604 A2 | 12/2006 |
| WO | 2006/137772 A1 | 12/2006 |
| WO | 2006130403 A1 | 12/2006 |
| WO | 2007/002313 A2 | 1/2007 |
| WO | 2007/008541 A2 | 1/2007 |
| WO | 2007/049158 A2 | 5/2007 |
| WO | 2007/050980 A2 | 5/2007 |
| WO | 2007/055374 A1 | 5/2007 |
| WO | 2007/055941 A1 | 5/2007 |
| WO | 2007/056341 A1 | 5/2007 |
| WO | 2007/061880 A1 | 5/2007 |
| WO | 2007/061978 A1 | 5/2007 |
| WO | 2007/064797 A2 | 6/2007 |
| WO | 2007/071598 A1 | 6/2007 |
| WO | 2007/087129 A2 | 8/2007 |
| WO | 2007/087130 A2 | 8/2007 |
| WO | 2007/118137 A1 | 10/2007 |
| WO | 2007/119463 A1 | 10/2007 |
| WO | 2007/122830 A1 | 11/2007 |
| WO | 2007/125984 A1 | 11/2007 |
| WO | 2007/126765 A2 | 11/2007 |
| WO | 2007/129044 A1 | 11/2007 |
| WO | 2007/129052 A1 | 11/2007 |
| WO | 2007/138072 A2 | 12/2007 |
| WO | 2007/139002 A1 | 12/2007 |
| WO | 2007/143557 A2 | 12/2007 |
| WO | 2008/005457 A2 | 1/2008 |
| WO | 2008/009963 A2 | 1/2008 |
| WO | 2008/010985 A2 | 1/2008 |
| WO | 2008/011611 A2 | 1/2008 |
| WO | 2008/012418 A1 | 1/2008 |
| WO | 2008/013963 A2 | 1/2008 |
| WO | 2008/016643 A2 | 2/2008 |
| WO | 2008/024970 A2 | 2/2008 |
| WO | 2008/024978 A2 | 2/2008 |
| WO | 2008/036272 A1 | 3/2008 |
| WO | 2008/047229 A2 | 4/2008 |
| WO | 2008/053913 A1 | 5/2008 |
| WO | 2008/067874 A1 | 6/2008 |
| WO | 2008/074788 A1 | 6/2008 |
| WO | 2008/078837 A1 | 7/2008 |
| WO | 2008/092199 A1 | 8/2008 |
| WO | 2008/093024 A2 | 8/2008 |
| WO | 2008/115262 A2 | 9/2008 |
| WO | 2008/115719 A1 | 9/2008 |
| WO | 2008/119015 A2 | 10/2008 |
| WO | 2008/129280 A1 | 10/2008 |
| WO | 2008/139152 A1 | 11/2008 |
| WO | 2008/145843 A1 | 12/2008 |
| WO | 2008/151184 A1 | 12/2008 |
| WO | 2008/151211 A1 | 12/2008 |
| WO | 2008/154221 A2 | 12/2008 |
| WO | 2009/005638 A2 | 1/2009 |
| WO | 2009/022171 A1 | 2/2009 |
| WO | 2009/032861 A1 | 3/2009 |
| WO | 2009/037001 A2 | 3/2009 |
| WO | 2009/052319 A1 | 4/2009 |
| WO | 2009/078992 A1 | 6/2009 |
| WO | 2009/100406 A2 | 8/2009 |
| WO | 2009/109710 A1 | 9/2009 |
| WO | 2009/115267 A2 | 9/2009 |
| WO | 2009/156484 A2 | 12/2009 |
| WO | 2010/006191 A1 | 1/2010 |
| WO | 2010/007046 A2 | 1/2010 |
| WO | 2010/007756 A1 | 1/2010 |
| WO | 2010/008739 A2 | 1/2010 |
| WO | 2010/032147 A2 | 3/2010 |

(56) References Cited

FOREIGN PATENT DOCUMENTS

| WO | 2010/034838 A2 | 4/2010 |
|---|---|---|
| WO | 2010/046780 A2 | 4/2010 |
| WO | 2010/068863 A2 | 6/2010 |
| WO | 2010/075376 A2 | 7/2010 |
| WO | 2010/088574 A1 | 8/2010 |
| WO | 2010/108921 A1 | 9/2010 |
| WO | 2010/111527 A1 | 9/2010 |
| WO | 2010/112520 A1 | 10/2010 |
| WO | 2010/127855 A1 | 11/2010 |
| WO | 2010/137350 A1 | 12/2010 |
| WO | 2010/151747 A1 | 12/2010 |
| WO | 2011/008931 A2 | 1/2011 |
| WO | 2011/012661 A1 | 2/2011 |
| WO | 2011/072275 A2 | 6/2011 |
| WO | 2011/073328 A1 | 6/2011 |
| WO | 2011/082400 A2 | 7/2011 |
| WO | 2011/119869 A1 | 9/2011 |
| WO | 2011/125568 A1 | 10/2011 |
| WO | 2011/133920 A1 | 10/2011 |
| WO | 2011/134925 A1 | 11/2011 |
| WO | 2012/003405 A1 | 1/2012 |
| WO | 2012/004217 A1 | 1/2012 |
| WO | 2012/020131 A2 | 2/2012 |
| WO | 2012/020133 A1 | 2/2012 |
| WO | 2012/024604 A2 | 2/2012 |
| WO | 2012/061337 A1 | 5/2012 |
| WO | 2012/064559 A1 | 5/2012 |
| WO | 2012/074050 A1 | 6/2012 |
| WO | 2012/085650 A1 | 6/2012 |
| WO | 2012/085789 A1 | 6/2012 |
| WO | 2012/101062 A1 | 8/2012 |
| WO | 2012/117097 A1 | 9/2012 |
| WO | 2012/123745 A1 | 9/2012 |
| WO | 2012/127385 A1 | 9/2012 |
| WO | 2012/147890 A1 | 11/2012 |
| WO | 2012/149540 A1 | 11/2012 |
| WO | 2012/152915 A1 | 11/2012 |
| WO | 2012/154880 A1 | 11/2012 |
| WO | 2012/156918 A1 | 11/2012 |
| WO | 2012/156919 A1 | 11/2012 |
| WO | 2012/156920 A1 | 11/2012 |
| WO | 2012/166951 A1 | 12/2012 |
| WO | 2013/013815 A1 | 1/2013 |
| WO | 2013/013817 A1 | 1/2013 |
| WO | 2013/017480 A1 | 2/2013 |
| WO | 2013/024004 A1 | 2/2013 |
| WO | 2013/033068 A1 | 3/2013 |
| WO | 2013/038390 A1 | 3/2013 |
| WO | 2013/041602 A1 | 3/2013 |
| WO | 2013/055984 A1 | 4/2013 |
| WO | 2013/059648 A1 | 4/2013 |
| WO | 2013/064884 A1 | 5/2013 |
| WO | 2013/152198 A1 | 10/2013 |
| WO | 2013/152727 A1 | 10/2013 |
| WO | 2013/163404 A1 | 10/2013 |
| WO | 2013/178816 A1 | 12/2013 |
| WO | 2013/180193 A1 | 12/2013 |
| WO | 2013/188813 A2 | 12/2013 |
| WO | 2014/000418 A1 | 1/2014 |
| WO | 2014/005125 A2 | 1/2014 |
| WO | 2014/012511 A1 | 1/2014 |
| WO | 2014/015167 A2 | 1/2014 |
| WO | 2014/025808 A1 | 2/2014 |
| WO | 2014/031928 A2 | 2/2014 |
| WO | 2014/047111 A1 | 3/2014 |
| WO | 2014/055955 A1 | 4/2014 |
| WO | 2014/056620 A1 | 4/2014 |
| WO | 2014/074906 A1 | 5/2014 |
| WO | 2014/081299 A1 | 5/2014 |
| WO | 2014/081300 A1 | 5/2014 |
| WO | 2014/081301 A1 | 5/2014 |
| WO | 2014/081303 A1 | 5/2014 |
| WO | 2014/089112 A1 | 6/2014 |
| WO | 2014/144169 A1 | 9/2014 |
| WO | 2014/146995 A1 | 9/2014 |
| WO | 2014/149164 A1 | 9/2014 |
| WO | 2014/151936 A1 | 9/2014 |
| WO | 2014/153208 A1 | 9/2014 |
| WO | 2014/164704 A2 | 10/2014 |
| WO | 2014/181287 A1 | 11/2014 |
| WO | 2014/187297 A1 | 11/2014 |
| WO | 2014/187298 A1 | 11/2014 |
| WO | 2014/190199 A1 | 11/2014 |
| WO | 2014/194270 A1 | 12/2014 |
| WO | 2015/031725 A1 | 3/2015 |
| WO | 2015/035059 A1 | 3/2015 |
| WO | 2015/051043 A1 | 4/2015 |
| WO | 2015/051458 A1 | 4/2015 |
| WO | 2015/061247 A2 | 4/2015 |
| WO | 2015/077246 A1 | 5/2015 |
| WO | 2015/110999 A1 | 7/2015 |
| WO | 2015/120800 A1 | 8/2015 |
| WO | 2015/140572 A1 | 9/2015 |
| WO | 2015/142903 A2 | 9/2015 |
| WO | 2015/157057 A1 | 10/2015 |
| WO | 2015/170218 A1 | 11/2015 |
| WO | 2016/020307 A1 | 2/2016 |
| WO | 2016/042341 A1 | 3/2016 |
| WO | 2016/057779 A2 | 4/2016 |
| WO | 2016/058544 A1 | 4/2016 |
| WO | 2016/061527 A1 | 4/2016 |
| WO | 2016/100711 A1 | 6/2016 |
| WO | 2016/133838 A1 | 8/2016 |
| WO | 2016/173557 A1 | 11/2016 |
| WO | 2016/176657 A1 | 11/2016 |
| WO | 2016/183266 A1 | 11/2016 |
| WO | 2017/007755 A1 | 1/2017 |
| WO | 2017/007756 A1 | 1/2017 |
| WO | 2017/027984 A1 | 2/2017 |
| WO | 2017/044889 A1 | 3/2017 |
| WO | 2017/046133 A1 | 3/2017 |
| WO | 2017/075694 A1 | 5/2017 |
| WO | 2017/106818 A1 | 6/2017 |
| WO | 2017/146116 A1 | 8/2017 |
| WO | 2017/156265 A1 | 9/2017 |

OTHER PUBLICATIONS

U.S. Appl. No. 15/741,657, filed Jan. 3, 2018, 2018-0194769, Published.

U.S. Appl. No. 15/934,299, filed Mar. 23, 2018, 2018-0215759, Allowed.

Abel et al., pigenetic targets of HDAC inhibition in neurodegenerative and psychiatric disorders. Curr Opin Pharmacol. Feb. 2008;8(1):57-64.

Bennett et al., Cecil Textbook of Medicine, 2th Edition, W.B. Sanders Company, Philadelphia. vol. 1, pp. 1004-1010, (1996).

Bowers et al., The Class I HDAC inhibitor RGFP963 enhances consolidation of cued fear extinction. Learn Mem. Mar. 16, 2015;22(4):225-31.

CAS Registry No. 1072874-82-8. Entered STN: Nov. 14, 2008, 1 page.

CDC, CDC and Fungal Diseases. Retrieved online at: http://www.cdc.gov/ncezid/dfwed/mycotics. 2 pages, Sep. 2011.

Choong et al., A novel histone deacetylase 1 and 2 isoform-specific inhibitor alleviates experimental Parkinson's Disease. Neurobiology of Aging. DOI: 10.1016/j.neurobiolaging.2015.10.001, 54 pages, Oct. 2, 2015.

Dorostkar et al., Analyzing dendritic spine pathology in Alzheimer's disease: problems and opportunities. Acta Neuropathol. Jul. 2015;130(1):1-19.

Faraco et al., The therapeutic potential of HDAC inhibitors in the treatment of multiple sclerosis. Mol Med. May-Jun. 2011;17(5-6):442-7.

Fischer et al., Recovery of learning and memory is associated with chromatin remodelling. Nature. May 10, 2007;447 (7141):178-82.

Graff et al., an epigenetic blockade of cognitive functions in the neurodegenerating brain. Nature. Feb. 29, 2012;483 (7388):222-6.

Grohol, Symptoms & Treatments of Mental Disorders. Mental Disorders & Conditions—DSM. Retrieved online at: https://psychcentral.com/disorders/ 9 pages, Feb. 27, 2019.

(56) References Cited

OTHER PUBLICATIONS

Guan et al., HDAC2 negatively regulates memory formation and synaptic plasticity. Nature. May 7, 2009;459 (7243):55-60.

Gura, Systems for identifying new drugs are often faulty. Science. Nov. 7, 1997;278(5340):1041-2.

Herman et al., Histone deacetylase inhibitors reverse gene silencing in Friedreich's ataxia. Nat Chem Biol. Oct. 2006;2(10):551-8.

Johnson et al., Relationships between drug activity in NCI preclinical in vitro and in vivo models and early clinical trials. Br J Cancer. May 18, 2001;84(10):1424-31.

Kattar et al., Parallel medicinal chemistry approaches to selective HDAC1/HDAC2 inhibitor (SHI-1:2) optimization. Bioorg Med Chem Lett. Feb. 15, 2009;19(4):1168-72.

Levenson et al., Regulation of histone acetylation during memory formation in the hippocampus. J Biol Chem. Sep. 24, 2004;279(39):40545-59.

Masliah et al., Altered expression of synaptic proteins occurs early during progression of Alzheimer's disease. Neurology. Jan. 9, 2001;56(1):127-9.

MedicineNet.com, Definition of Cancer. Retrieved online at: http://www.medterms.com. 1 page, Sep. 18, 2004.

MedlinePlus, Infections. Retrieved online at: https://medlineplus.gov/infections.html. 10 pages, Jul. 6, 2016.

Methot et al., Exploration of the internal cavity of histone deacetylase (HDAC) with selective HDAC1/HDAC2 inhibitors (SHI-1:2). Bioorg Med Chem Lett. Feb. 1, 2008;18(3):973-8.

Mielcarek et al., SAHA decreases HDAC 2 and 4 levels in vivo and improves molecular phenotypes in the R6/2 mouse model of Huntington's disease. PLoS One. 2011;6(11):e27746, 10 pages.

Pearce et al., Failure modes in anticancer drug discovery and development. Cancer Drug Design and Discovery, Elsevier Inc., Stephen Neidle (Ed.). Chapter 18, pp. 424-435, (2008).

Qin et al., Social deficits in Shank3-deficient mouse models of autism are rescued by histone deacetylase (HDAC) inhibition. Nat Neurosci. Apr. 2018;21(4):564-575.

Schulz-Schaeffer, The synaptic pathology of alpha-synuclein aggregation in dementia with Lewy bodies, Parkinson's disease and Parkinson's disease dementia. Acta Neuropathol. Aug. 2010;120(2):131-43.

She et al., Selectivity and Kinetic Requirements of HDAC Inhibitors as Progranulin Enhancers for Treating Frontotemporal Dementia. Cell Chem Biol. Jul. 20, 2017;24(7):892-906.e5.

Sprow et al., Histone acetylation in the nucleus accumbens shell modulates ethanol-induced locomotor activity in DBA/2J mice. Alcohol Clin Exp Res. Sep. 2014;38(9):2377-86.

Stevens, Fungal Skin Infections. UNM School of Medicine, Continuum of Care. Retrieved online at: hsc.unm.edu/som/coc. 1 page, (2000).

Tan et al., Upregulation of histone deacetylase 2 in laser capture nigral microglia in Parkinson's disease. Neurobiol Aging. Aug. 2018; 8 pages, pre-publication version.

UCSF Medical Center, Neurological Disorders. Retrieved online at: https://www.ucshealth.org/conditions/neurological_disorders/ 1 page, (2016).

University of Maryland Medical Center, Myeloproliferative disorders. Retrieved online at: http://www.umm.edu/health/-medical/altmed/condition/myeloproliferative-disorders. 8 pages, (2017).

Wagner et al., Kinetically Selective Inhibitors of Histone Deacetylase 2 (HDAC2) as Cognition Enhancers. Chem Sci. Jan. 1, 2015;6(1):804-815.

Xu et al., Dendritic spine dysgenesis in Rett syndrome. Front Neuroanat. Sep. 10, 2014;8:97. 8 pages.

Zhu et al., Investigation on the isoform selectivity of histone deacetylase inhibitors using chemical feature based pharmacophore and docking approaches. Eur J Med Chem. May 2010;45(5):1777-91.

Copending U.S. Appl. No. 16/726,990, filed Aug. 16, 2018.
Copending U.S. Appl. No. 16/681,213, filed Aug. 16, 2018.
U.S. Appl. No. 15/741,609, filed Jan. 3, 2018, U.S. Pat. No. 10,421,756, Issued.
U.S. Appl. No. 16/726,990, filed Dec. 26, 2019, Pending.
U.S. Appl. No. 15/867,982, filed Jan. 11, 2018, U.S. Pat. No. 9,951,069, Issued.
U.S. Appl. No. 15/934,299, filed Mar. 23, 2018, U.S. Pat. No. 10,519,149, Issued.
U.S. Appl. No. 16/381,213, filed Nov. 12, 2019, Pending.

BICYCLIC INHIBITORS OF HISTONE DEACETYLASE

RELATED APPLICATIONS

This application is a 35 U.S.C. § 371 national stage filing of International Application No. PCT/US2018/013262 filed Jan. 11, 2018, which in turn claims priority to U.S. Provisional Application No. 62/445,022 filed Jan. 11, 2017 and U.S. Provisional Application No. 62/555,298 filed Sep. 7, 2017, the entire contents of each of which are incorporated herein by reference.

STATEMENT REGARDING FEDERALLY SPONSORED RESEARCH AND DEVELOPMENT

This invention was made with government support under Small Business Innovation Research (SBIR) grant 1R43AG048651-01A1 awarded by the National Institute of Health (NIH). The government has certain rights in the invention.

BACKGROUND

Inhibitors of histone deacetylases (HDAC) have been shown to modulate transcription and to induce cell growth arrest, differentiation and apoptosis. HDAC inhibitors also enhance the cytotoxic effects of therapeutic agents used in cancer treatment, including radiation and chemotherapeutic drugs. Marks, P., Rifkind, R. A., Richon, V. M., Breslow, R., Miller, T., Kelly, W. K. Histone deacetylases and cancer: causes and therapies. Nat Rev Cancer, 1, 194-202, (2001); and Marks, P. A., Richon, V. M., Miller, T., Kelly, W. K. Histone deacetylase inhibitors. Adv Cancer Res, 91, 137-168, (2004). Moreover, recent evidence indicates that transcriptional dysregulation may contribute to the molecular pathogenesis of certain neurodegenerative disorders, such as Huntington's disease, spinal muscular atrophy, amyotropic lateral sclerosis, and ischemia. Langley, B., Gensert, J. M., Beal, M. F., Ratan, R. R. Remodeling chromatin and stress resistance in the central nervous system: histone deacetylase inhibitors as novel and broadly effective neuroprotective agents. Curr Drug Targets CNS Neurol Disord, 4, 41-50, (2005). A recent review has summarized the evidence that aberrant histone acetyltransferase (HAT) and histone deacetylases (HDAC) activity may represent a common underlying mechanism contributing to neurodegeneration. Moreover, using a mouse model of depression, Nestler has recently highlighted the therapeutic potential of histone deacetylation inhibitors (HDAC5) in depression. Tsankova, N. M., Berton, O., Renthal, W., Kumar, A., Neve, R. L., Nestler, E. J. Sustained hippocampal chromatin regulation in a mouse model of depression and antidepressant action. Nat Neurosci, 9, 519-525, (2006).

There are 18 known human histone deacetylases, grouped into four classes based on the structure of their accessory domains. Class I includes HDAC1, HDAC2, HDAC3, and HDAC8 and has homology to yeast Rpd3. HDAC4, HDAC5, HDAC7, and HDAC9 belong to class IIa and have homology to yeast Hda1. HDAC6 and HDAC10 contain two catalytic sites and are classified as class IIb. Class III (the sirtuins) includes SIRT1, SIRT2, SIRT3, SIRT4, SIRT5, SIRT6, and SIRT7. HDAC11 is another recently identified member of the HDAC family and has conserved residues in its catalytic center that are shared by both class I and class II deacetylases and is sometimes placed in class IV.

HDACs have been shown to be powerful negative regulators of long-term memory processes. Nonspecific HDAC inhibitors enhance synaptic plasticity as well as long-term memory (Levenson et al., 2004, J. Biol. Chem. 279:40545-40559; Lattal et al., 2007, Behav Neurosci 121:1125-1131; Vecsey et al., 2007, J. Neurosci 27:6128; Bredy, 2008, Learn Mem 15:460-467; Guan et al., 2009, Nature 459:55-60; Malvaez et al., 2010, Biol. Psychiatry 67:36-43; Roozendaal et al., 2010, J. Neurosci. 30:5037-5046). For example, HDAC inhibition can transform a learning event that does not lead to long-term memory into a learning event that does result in significant long-term memory (Stefanko et al., 2009, Proc. Natl. Acad. Sci. USA 106:9447-9452). Furthermore, HDAC inhibition can also generate a form of long-term memory that persists beyond the point at which normal memory fails. HDAC inhibitors have been shown to ameliorate cognitive deficits in genetic models of Alzheimer's disease (Fischer et al., 2007, Nature 447:178-182; Kilgore et al., 2010, Neuropsychopharmacology 35:870-880). These demonstrations suggest that modulating memory via HDAC inhibition have considerable therapeutic potential for many memory and cognitive disorders.

The role of individual HDACs in long-term memory has been explored in two recent studies. Kilgore et al. 2010, Neuropsychopharmacology 35:870-880 revealed that nonspecific HDAC inhibitors, such as sodium butyrate, inhibit class I HDACs (HDAC1, HDAC2, HDAC3, HDAC8) with little effect on the class IIa HDAC family members (HDAC4, HDAC5, HDAC7, HDAC9). This suggests that inhibition of class I HDACs may be critical for the enhancement of cognition observed in many studies. Indeed, forebrain and neuron specific overexpression of HDAC2, but not HDAC1, decreased dendritic spine density, synaptic density, synaptic plasticity and memory formation. (Guan et al., 2009, Nature, 459:55-60). In contrast, HDAC2 knockout mice exhibited increased synaptic density, increased synaptic plasticity and increased dendritic density in neurons. These HDAC2 deficient mice also exhibited enhanced learning and memory in a battery of learning behavioral paradigms. This work demonstrates that HDAC2 is a key regulator of synaptogenesis and synaptic plasticity. Additionally, Guan et al. showed that chronic treatment of mice with SAHA (an HDAC 1, 2, 3, 6, 8 inhibitor) reproduced the effects seen in the HDAC2 deficient mice and rescued the cognitive impairment in the HDAC2 overexpressing mice.

The inhibition of HDAC2 (selectively or in combination with inhibition of other class I HDACs; as the primary target, or as part of a complex with other proteins) is an attractive therapeutic target. Selective inhibition might be achieved by targeting specific HDAC isoforms such as HDAC2, in isolation, or as part of a functional multi-protein complex. Such inhibition has the potential for enhancing cognition and facilitating the learning process through increasing synaptic and dendritic density in neuronal cell populations. In addition, inhibition of specific HDACs, such as HDAC2, may also be therapeutically useful in treating a wide variety of other diseases and disorders.

SUMMARY

Disclosed are compounds and pharmaceutically acceptable salts thereof, and pharmaceutical compositions, which are useful in the treatment of conditions associated with the activity of HDAC (e.g., HDAC2). (See e.g., Table 2).

One of the advantages of certain compounds described herein is that they possess improved brain exposure and have higher free brain concentration. For example, the brain Cmax exposure and projected free brain concentration of Compound 14 is 4-fold higher than comparator 1 (which only differs from Compound 14 by the absence of a methyl group. See Table 5) when comparator 1 data is scaled for comparison. In addition, Compound 17 (which only differs by the presence of an ethyl group when compared with comparator 1) is nearly 7-fold higher in brain Cmax exposure and 5-fold higher in projected free brain concentration when comparator 1 data is scaled for comparison. See Table 5.

Certain compounds described herein provide enhanced safety parameters. For example, replacement of the bottom phenyl ring for heteroaromatics afforded compounds with improved performance in colony forming unit assays, showing fewer effects on human erythroid and myeloid progenitors. See e.g., Table 4, Compounds 4, 8, 11, and 12 compared to comparator 2 and 3. Changing a 4-fluorophenyl group for a 2,4-difluorophenyl group also has a profound effect in safety parameters. See Table 4, Comparator 6 with Compound 9.

Certain compounds described herein perform well in a cell lysate assay employing an exogenous substrate to measure HDAC inhibitory activity. See Table 3.

Conditions which are treatable by the disclosed compounds include, but are not limited to, neurological disorders, memory or cognitive function disorders or impairments, extinction learning disorders, fungal diseases or infections, inflammatory diseases, hematological diseases, neoplastic diseases, psychiatric disorders, and memory loss.

DETAILED DESCRIPTION

1. Compounds

Provided herein are compounds of the formula:

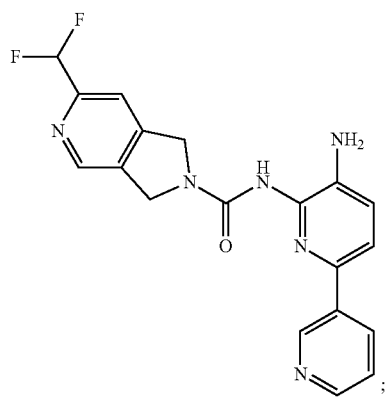

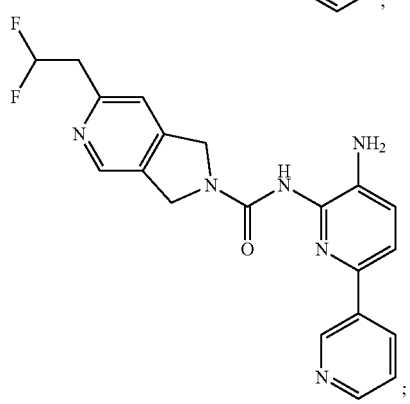

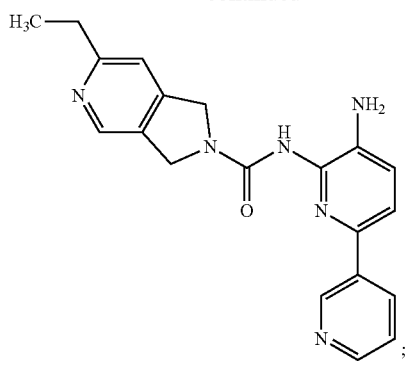

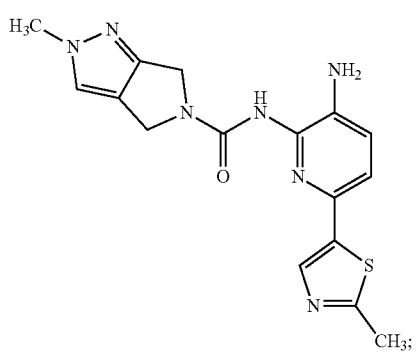

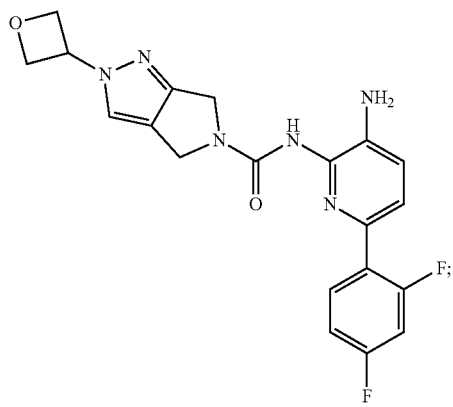

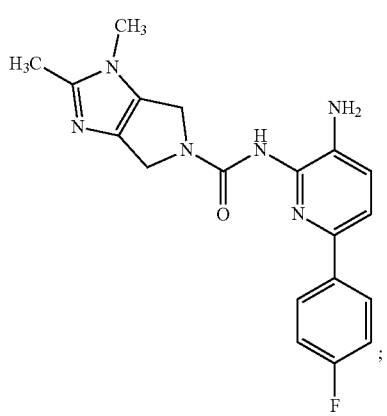

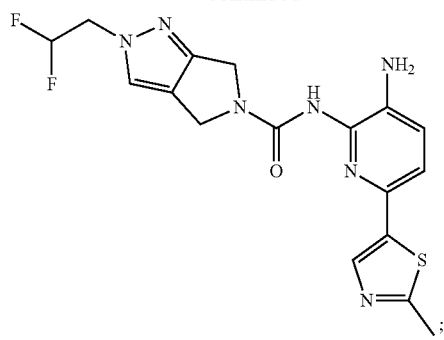
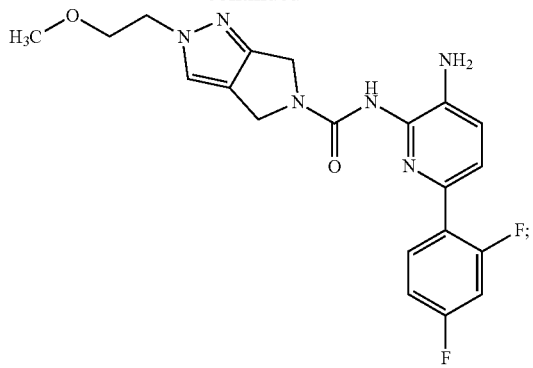
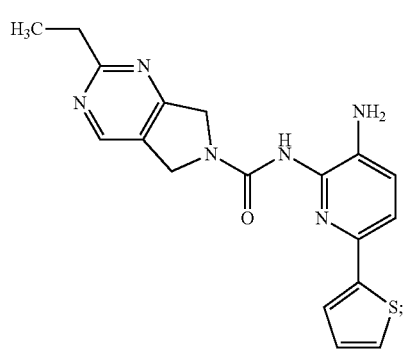
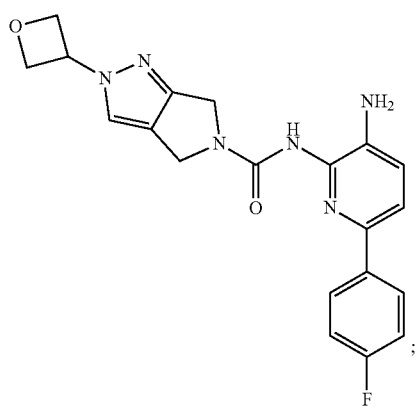
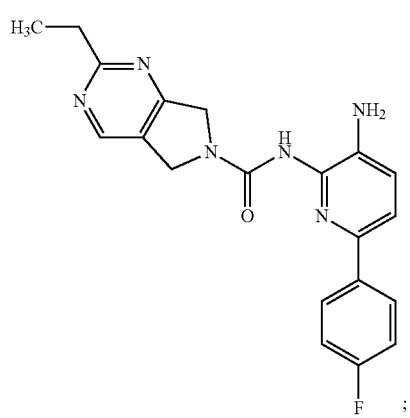
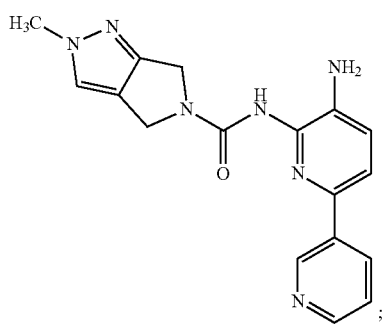
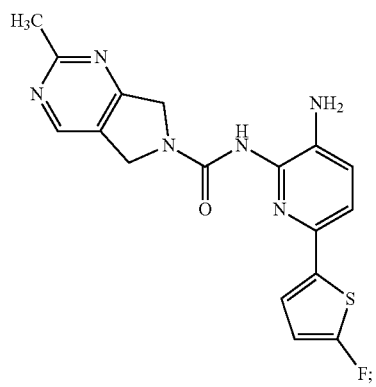
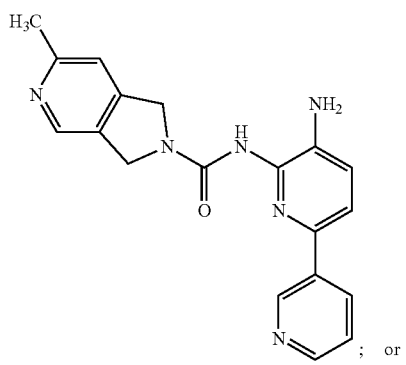

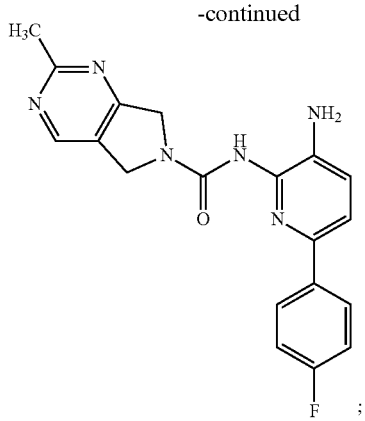

or a pharmaceutically acceptable salt thereof.

2. Definitions

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

Pharmaceutically acceptable salts as well as the neutral forms of the compounds described herein are included. For use in medicines, the salts of the compounds refer to non-toxic "pharmaceutically acceptable salts." Pharmaceutically acceptable salt forms include pharmaceutically acceptable acidic/anionic or basic/cationic salts. Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts. Pharmaceutically acceptable acidic/anionic salts include, e.g., the acetate, benzenesulfonate, benzoate, bicarbonate, bitartrate, carbonate, citrate, dihydrochloride, gluconate, glutamate, glycollylarsanilate, hexylresorcinate, hydrobromide, hydrochloride, malate, maleate, malonate, mesylate, nitrate, salicylate, stearate, succinate, sulfate, tartrate, and tosylate.

The term "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The terms "treatment," "treat," and "treating" refer to reversing, alleviating, reducing the likelihood of developing, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

The term "effective amount" or "therapeutically effective amount" includes an amount of a compound described herein that will elicit a biological or medical response of a subject.

3. Uses, Formulation and Administration

In some embodiments, compounds and compositions described herein are useful in treating conditions associated with the activity of HDAC. Such conditions include for example, those described below.

Recent reports have detailed the importance of histone acetylation in central nervous system ("CNS") functions such as neuronal differentiation, memory formation, drug addiction, and depression (Citrome, Psychopharmacol. Bull. 2003, 37, Suppl. 2, 74-88; Johannessen, CNS Drug Rev. 2003, 9, 199-216; Tsankova et al., 2006, Nat. Neurosci. 9, 519-525; Bousiges et al., 2013, PLoS ONE 8(3), e57816). Thus, in one aspect, the provided compounds and compositions may be useful in treating a neurological disorder. Examples of neurological disorders include: (i) chronic neurodegenerative diseases such as fronto-temporal lobar degeneration (frontotemporal dementia, FTD), FTD-GRN, familial and sporadic amyotrophic lateral sclerosis (FALS and ALS, respectively), familial and sporadic Parkinson's disease, Huntington's disease, familial and sporadic Alzheimer's disease, multiple sclerosis, muscular dystrophy, olivopontocerebellar atrophy, multiple system atrophy, Wilson's disease, progressive supranuclear palsy, diffuse Lewy body disease, corticodentatonigral degeneration, progressive familial myoclonic epilepsy, striatonigral degeneration, torsion dystonia, familial tremor, Down's Syndrome, Gilles de la Tourette syndrome, Hallervorden-Spatz disease, diabetic peripheral neuropathy, dementia pugilistica, AIDS Dementia, age related dementia, age associated memory impairment, and amyloidosis-related neurodegenerative diseases such as those caused by the prion protein (PrP) which is associated with transmissible spongiform encephalopathy (Creutzfeldt-Jakob disease, Gerstmann-Straussler-Scheinker syndrome, scrapie, and kuru), and those caused by excess cystatin C accumulation (hereditary cystatin C angiopathy); and (ii) acute neurodegenerative disorders such as traumatic brain injury (e.g., surgery-related brain injury), cerebral edema, peripheral nerve damage, spinal cord injury, Leigh's disease, Guillain-Barre syndrome, lysosomal storage disorders such as lipofuscinosis, Alper's disease, restless leg syndrome, vertigo as result of CNS degeneration; pathologies arising with chronic alcohol or drug abuse including, for example, the degeneration of neurons in locus coeruleus and cerebellum, drug-induced movement disorders; pathologies arising with aging including degeneration of cerebellar neurons and cortical neurons leading to cognitive and motor impairments; and pathologies arising with chronic amphetamine abuse to including degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor) and Wernicke-Korsakoff's related dementia. Neurological disorders affecting sensory neurons include Friedreich's ataxia, diabetes, peripheral neuropathy, and retinal neuronal degeneration. Other neurological disorders include nerve injury or trauma associated with spinal cord injury. Neurological disorders of limbic and cortical systems include cerebral amyloidosis, Pick's atrophy, and Rett syndrome. In another aspect, neurological disorders include disorders of mood, such as affective disorders and anxiety; disorders of social behavior, such as character defects and personality disorders; disorders of learning, memory, and intelligence, such as mental retardation and dementia. Thus, in one aspect the disclosed compounds and compositions may be useful in treating schizophrenia, delirium, attention deficit hyperactivity disorder (ADHD), schizoaffective disorder, Alzheimer's disease, vascular dementia, Rubinstein-Taybi syndrome, depression, mania, attention deficit disorders, drug addiction, dementia, dementia including BPSD manifestations, agitation, apathy, anxiety, psychoses, personality disorders, bipolar disorders, unipolar affective disorder, obsessive-compulsive disorders, eating disorders, post-traumatic stress disorders, irritability, adolescent conduct disorder and disinhibition. They may also be useful for spontaneous, toxic, neoplastic, post-traumatic and post-infectious tinnitus and smelling impairment.

Transcription is thought to be a key step for long-term memory formation (Alberini, 2009, Physiol. Rev. 89, 121-145). Transcription is promoted by specific chromatin modifications, such as histone acetylation, which modulate histone-DNA interactions (Kouzarides, 2007, Cell, 128:693-705), as well as transcription factor-DNA interactions. Modifying enzymes, such as histone acetyltransferases (HATs) and histone deacetylases (HDACs), regulate the state of acetylation on histone tails. In general, histone acetylation promotes gene expression, whereas histone deacetylation leads to gene silencing, although treatment with HDAC inhibitors can result in both upregulation and downregulation of the expression levels of specific genes. Numerous studies have shown that a potent HAT, cAMP response element-binding protein (CREB)-binding protein (CBP), is necessary for long-lasting forms of synaptic plasticity and long term memory (for review, see Barrett, 2008, Learn Mem 15:460-467). Thus, in one aspect, the provided compounds and compositions may be useful for promoting cognitive function and enhancing learning and memory formation.

The compounds and compositions described herein may also be used for treating fungal diseases or infections.

In another aspect, the compounds and compositions described herein may be used for treating inflammatory diseases such as stroke, rheumatoid arthritis, lupus erythematosus, ulcerative colitis and traumatic brain injuries (Leoni et al., PNAS, 99(5); 2995-3000(2002); Suuronen et al. J. Neurochem. 87; 407-416 (2003) and Drug Discovery Today, 10: 197-204 (2005).

In yet another aspect, the compounds and compositions described herein may be used for treating a cancer caused by the proliferation of neoplastic cells. Such cancers include e.g., solid tumors, neoplasms, carcinomas, sarcomas, leukemias, lymphomas and the like. In one aspect, cancers that may be treated by the compounds and compositions described herein include, but are not limited to: cardiac cancer, lung cancer, gastrointestinal cancer, genitourinary tract cancer, liver cancer, nervous system cancer, gynecological cancer, hematologic cancer, skin cancer, and adrenal gland cancer. In one aspect, the compounds and compositions described herein are useful in treating cardiac cancers selected from sarcoma (angiosarcoma, fibrosarcoma, rhabdomyosarcoma, liposarcoma), myxoma, rhabdomyoma, fibroma, lipoma and teratoma. In another aspect, the compounds and compositions described herein are useful in treating a lung cancer selected from bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, and mesothelioma. In one aspect, the compounds and compositions described herein are useful in treating a gastrointestinal cancer selected from esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), and large bowel (adenocarcinoma, tubular adenoma, villous adenoma, hamartoma, leiomyoma). In one aspect, the compounds and compositions described herein are useful in treating a genitourinary tract cancer selected from kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma). In one aspect, the compounds and compositions described herein are useful in treating a liver cancer selected from hepatoma (hepatocellular carcinoma), cholangiocarcinoma, hepatoblastoma, angiosarcoma, hepatocellular adenoma, and hemangioma.

In some embodiments, the compounds described herein relate to treating, a bone cancer selected from osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochondroma (osteocartilaginous exostoses), benign chondroma, chondroblastoma, chondromyxofibroma, osteoid osteoma and giant cell tumors.

In one aspect, the compounds and compositions described herein are useful in treating a nervous system cancer selected from skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), and spinal cord (neurofibroma, meningioma, glioma, sarcoma).

In one aspect, the compounds and compositions described herein are useful in treating a gynecological cancer selected from uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

In one aspect, the compounds and compositions described herein are useful in treating a skin cancer selected from malignant melanoma, basal cell carcinoma, squamous cell carcinoma, Karposi's sarcoma, moles dysplastic nevi, lipoma, angioma, dermatofibroma, keloids, and psoriasis.

In one aspect, the compounds and compositions described herein are useful in treating an adrenal gland cancer selected from neuroblastoma.

In one aspect, the compounds and compositions described herein are useful in treating cancers that include, but are not limited to: leukemias including acute leukemias and chronic leukemias such as acute lymphocytic leukemia (ALL), Acute myeloid leukemia (AML), chronic lymphocytic leukemia (CLL), chronic myelogenous leukemia (CML) and Hairy Cell Leukemia; lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), Hodgkin's disease and non-Hodgkin's lymphomas, large-cell lymphomas, diffuse large B-cell lymphoma (DLBCL); Burkitt's lymphoma; mesothelioma, primary central nervous system (CNS) lymphoma; multiple myeloma; childhood solid tumors such as brain tumors, neuroblastoma, retinoblastoma, Wilm's tumor, bone tumors, and soft-tissue sarcomas, common solid tumors of adults such as head and neck cancers (e.g., oral, laryngeal and esophageal), genito urinary cancers (e.g., prostate, bladder, renal, uterine, ovarian, testicular, rectal and colon), lung cancer, breast cancer, pancreatic cancer, melanoma and other skin cancers, stomach cancer, brain tumors, liver cancer and thyroid cancer.

In one aspect, the compounds and compositions described herein are useful in treating a condition in a subject selected from a neurological disorder, memory or cognitive function disorder or impairment, extinction learning disorder, fungal disease or infection, inflammatory disease, hematological disease, psychiatric disorders, and neoplastic disease. In another aspect, the compounds and compositions described herein are useful in treating a condition selected from a) a cognitive function disorder or impairment associated with Alzheimer's disease, Huntington's disease, seizure induced memory loss, schizophrenia, Rubinstein Taybi syndrome, Rett Syndrome, Fragile X, Lewy body dementia, vascular dementia, fronto-temporal lobar degeneration (frontotemporal dementia, FTD), FTD-GRN, ADHD, dyslexia, bipolar disorder and social, cognitive and learning disorders associated with autism, traumatic head injury, attention deficit disorder, anxiety disorder, conditioned fear response, panic disorder, obsessive compulsive disorder, posttraumatic stress disorder (PTSD), phobia, social anxiety disorder, substance dependence recovery, Age Associated Memory Impairment (AAMI), Age Related Cognitive Decline (ARCD), ataxia, or Parkinson's disease; b) a hematological disease selected from acute myeloid leukemia, acute promyelocytic leukemia, acute lymphoblastic leukemia, chronic myelogenous leukemia, myelodysplastic syndromes, and sickle cell anemia; c) a neoplastic disease; and d) an extinction learning disorder selected from fear extinction and post-traumatic stress disorder. In one aspect, the condition treated by the compounds and compostions described herein is the condition is Alzheimer's disease, Huntington's disease, frontotemporal dementia, Freidreich's ataxia, post-traumatic stress disorder (PTSD), Parkinson's disease, depression, or substance dependence recovery.

In one aspect, the present disclosure provides a method of treating a condition described herein comprising administering to a subject an effective amount of a compound, or pharmaceutically acceptable salt described herein, or a composition thereof.

Also provided is the use of one or more of the compounds, or pharmaceutically acceptable salts thereof described herein, or a provided composition, for treating a condition described herein.

Also provided is the use of one or more of the compounds, or pharmaceutically acceptable salts thereof described herein for the manufacture of a medicament for treating a condition described herein.

Subjects may also be selected to be suffering from one or more of the described conditions before treatment with one or more of the described compounds, or pharmaceutically acceptable salts or compositions commences.

The present disclosure also provides pharmaceutically acceptable compositions comprising a compound described herein, or a pharmaceutically acceptable salt thereof; and a pharmaceutically acceptable carrier. These compositions can be used to treat one or more of the conditions described above.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Liquid dosage forms, injectable preparations, solid dispersion forms, and dosage forms for topical or transdermal administration of a compound are included herein.

The amount of provided compounds that may be combined with carrier materials to produce a composition in a single dosage form will vary depending upon the patient to be treated and the particular mode of administration. In some embodiments, provided compositions may be formulated so that a dosage of between 0.01-100 mg/kg body weight/day of the provided compound, such as e.g., 0.1-100 mg/kg body weight/day, can be administered to a patient receiving these compositions.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

EXEMPLIFICATION

Spots were visualized by UV light (254 and 365 nm). Purification by column and flash chromatography was carried out using silica gel (200-300 mesh). Solvent systems are reported as the ratio of solvents.

NMR spectra were recorded on a Bruker 400 (400 MHz) spectrometer. $^1$H chemical shifts are reported in δ values in ppm with tetramethylsilane (TMS, =0.00 ppm) as the internal standard. See, e.g., the data provided in Table 1.

LCMS spectra were obtained on an Agilent 1200 series 6110 or 6120 mass spectrometer with ESI (+) ionization mode. See, e.g., the data provided in Table 1.

Example 1
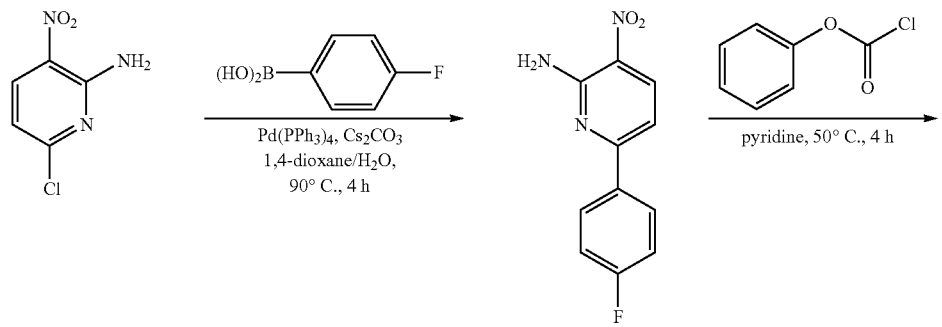
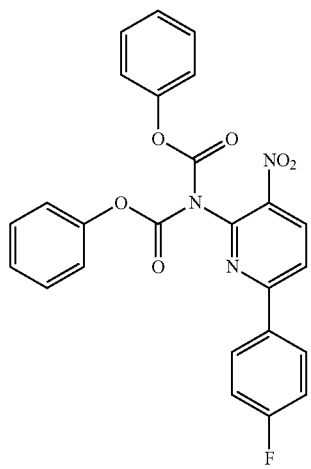
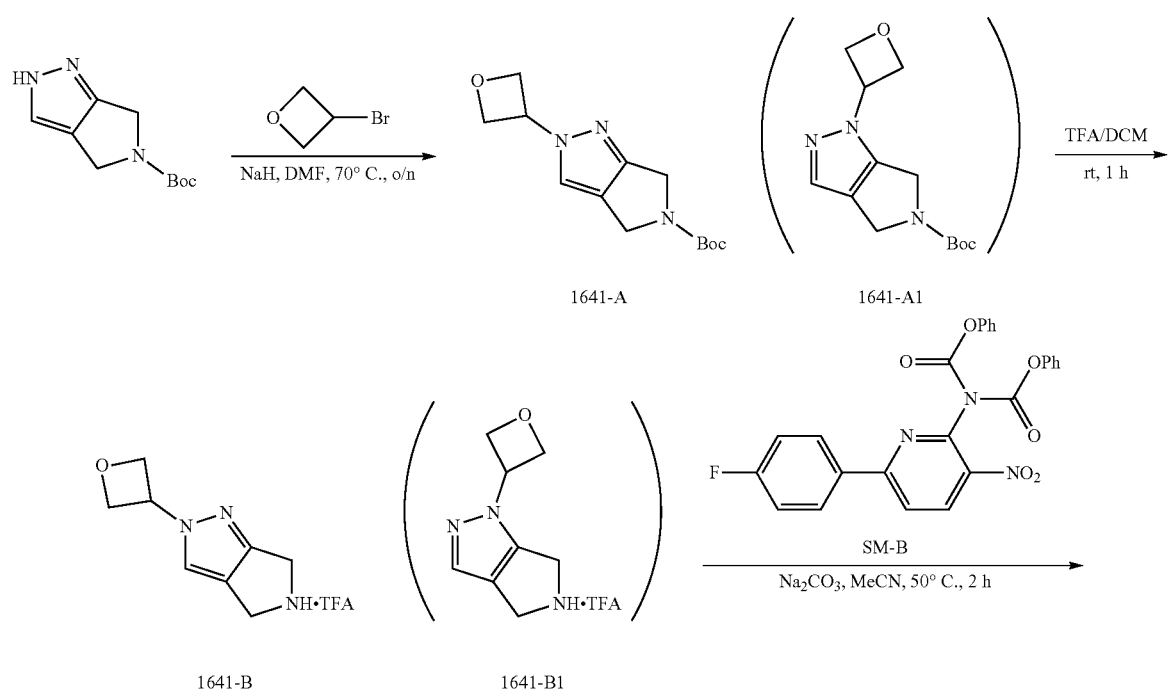

-continued

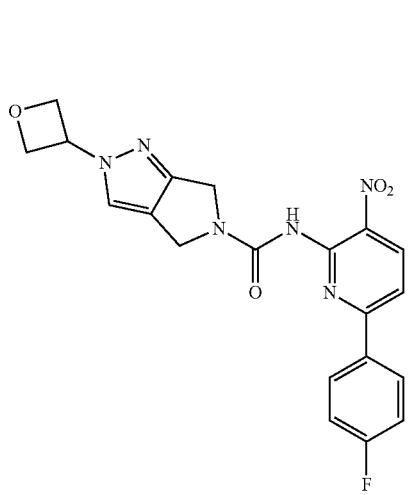 [SMILES: Nc1ccc(-c2ccc(F)cc2)nc1NC(=O)N1Cc2cn(C3COC3)nc2C1]

1641-C

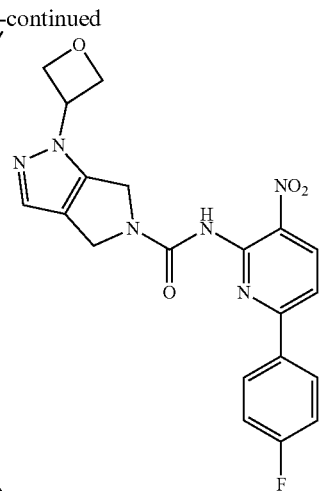

1641-C1

H₂, Pd/C
MeOH, rt, 1 h
→

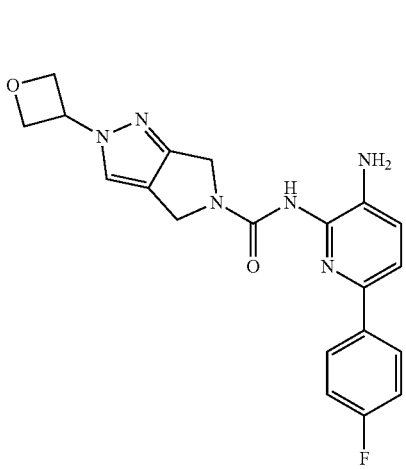

Compound 1

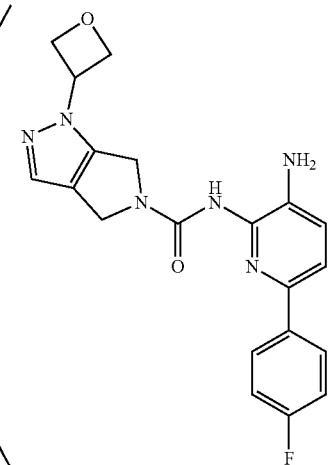

T-1641A

Synthesis of SM-A.

A mixture of 6-chloro-3-nitropyridin-2-amine (10.0 g, 57.6 mmol), 4-fluorophenylboronic acid (8.87 g, 63.4 mmol) and Cs₂CO₃ (37.56 g, 115.2 mmol) in dioxane/H₂O (200 mL/20 mL) was treated with Pd(PPh₃)₄ (2.44 g, 2.9 mmol) under a N₂ atmosphere. The mixture was stirred at 95° C. for 2 h and then concentrated in vacuo. The residue was dissolved with EtOAc (200 mL) and the solution was washed with brine (100 mL×3). The organic layer was dried over anhydrous Na₂SO₄ and then concentrated in vacuo. The residue was purified by column chromatography on silica gel (PE:EtOAc=10:1~3:1) to give SM-A (11.2 g, 83%) as a yellow solid. MS 234.2 [M+H]⁺.

Synthesis of SM-B.

To a stirred solution of SM-A (3.0 g, 13.0 mmol) in pyridine (60 mL) was added phenyl carbonochloridate (4.45 g, 28.5 mmol) dropwise while the reaction mixture was cooled with an ice bath. The resulting mixture was then warmed to RT following addition, and then was stirred at 50° C. for 4 h. The mixture was concentrated in vacuo, and the residue was purified by column chromatography on silica gel (PE:EtOAc=8:1~3:1) to give SM-B (5.2 g, 84%) as a yellow solid. MS 474.4 [M+H]⁺.

Synthesis of 1641-A and 1641-A1.

To a solution of tert-butyl 4,6-dihydropyrrolo[3,4-c]pyrazole-5(2H)-carboxylate (450 mg, 2.15 mmol) in DMF (8 mL) was added NaH (60% in mineral oil) (155 mg, 3.87 mmol) under ice bath cooling, and the reaction mixture was than allowed to warm to room temperature and stirred at room temperature for 30 min. 3-Bromooxetane (471 mg, 3.44 mmol) was then added to the reaction mixture, and the reaction was stirred at 70° C. overnight. The mixture was quenched with ice water (50 mL), extracted with EtOAc (15 mL×3), and the combined organic layers were washed with brine (12 mL×3), dried over anhydrous Na₂SO₄ and then concentrated in vacuo. The residue was purified by column chromatography on silica gel (PE:EtOAc=3:1~1:1) to give 1641-A and 1641-A1 (410 mg, 72%) as a colorless oil. MS 266.0 [M+H]⁺.

Synthesis of 1641-B and 1642-B1.

To a solution of 1641-A and 1642-A1 (410 mg, 1.55 mmol) in DCM (12 mL) was added TFA (3 mL), and the reaction mixture was stirred at room temperature for 1 h. The solvent was removed in vacuo to give 1641-B and 1641-B1 as a crude product which was carried on to the next step without further purification. MS 166.1 [M+H]⁺.

Synthesis of 1641-C and 1641-C1.

To a solution of 1641-B and 1641-B1 (crude product from last step) and SM-B (407 mg, 0.86 mmol) in MeCN (15 mL) was added Na$_2$CO$_3$ (912 mg, 8.6 mmol). The resulting reaction mixture was stirred at 50° C. for 2 h, whereupon the mixture was filtered and the filtrate was concentrated in vacuo. The residue was purified by column chromatography on silica gel (DCM:MeOH=80:1~50:1) to give 1641-C and 1641-C1 (230 mg, 63%) as a yellow solid. MS 425.0 [M+H]$^+$.

Synthesis of Compound 1 and T-1641A.

A mixture of 1641-C and 1641-C1 (230 mg, 0.54 mmol) and Pd/C (200 mg) in MeOH (30 mL) was stirred under a H$_2$ atmosphere (1 atm) at room temperature for 1 h. Pd/C was then removed by filtration through the Celite, and the filtrate was concentrated. The crude residue was purified by HPLC using chiral separation (Column: Chiralcel OD-3; Solvent: MeOH; Flow rate: 2 mL/min; RT$_{1641}$=2.359 min, RT$_{1641A}$=3.066 min) to give Compound 1 (110 mg, 52%) as a white solid (MS 395.2 [M+H]$^+$) and T-1641A (55 mg, 26%) as a white solid. MS 395.2 [M+H]$^+$.

Example 2

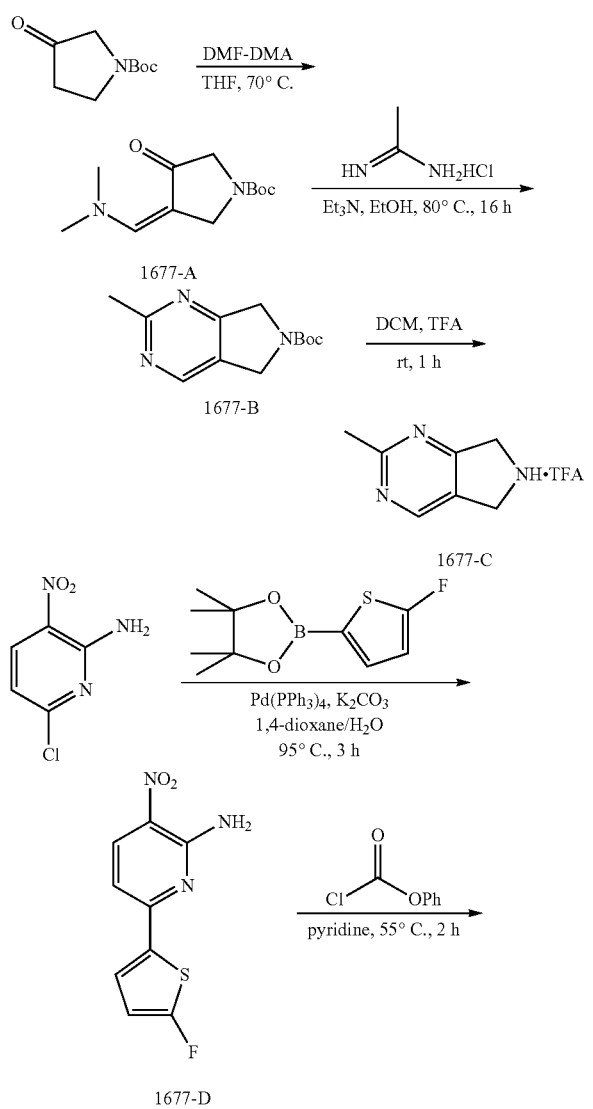

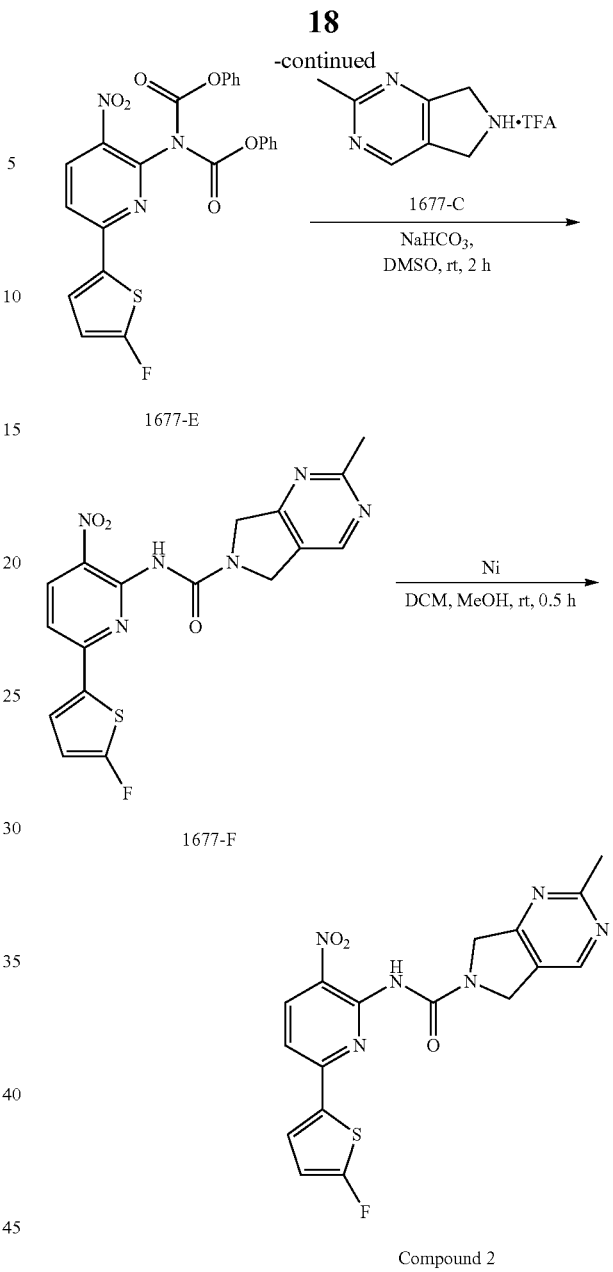

Synthesis of 1677-A.

To a solution of tert-butyl 3-oxopyrrolidine-1-carboxylate (2.0 g, 10.8 mmol) in THF (20 mL) was added DMF-DMA (3.8 g, 32.4 mmol). The reaction mixture was stirred at 70° C. for 12 h and then concentrated to give 1677-A (4.0 g) as a crude product which was carried on without further purification. MS 241.2 [M+H]$^+$.

Synthesis of 1677-B.

To a solution of 1677-A (2.0 g, crude product from last step) in EtOH (20 mL) was added acetimidamide hydrochloride (3.1 g, 33.0 mmol) and Et$_3$N (3.3 g, 33.0 mmol). The reaction mixture was stirred at 80° C. for 16 h, then was diluted with water (50 mL), and extracted with EtOAc (20 mL×3). The combined organic layers were washed with brine (20 mL×3), dried over anhydrous Na$_2$SO$_4$ and then concentrated in vacuo. The residue was purified by column chromatography on silica gel (PE:EtOAc=0:1~10:1) to give 1677-B (1.6 g, 83%) as a brown solid. MS 236.1 [M+H]$^+$.

Synthesis of 1677-C.

To a solution of 1677-B (800 mg, 3.4 mmol) in DCM (6 mL) was added TFA (6 mL) dropwise while cooling the reaction mixture in an ice bath. The reaction mixture was allowed to warm to room temperature, and was then stirred at room temperature for 1 h. The solvent was removed in vacuo to give 1677-C (850 mg) as a crude product which was carried on without further purification. MS 136.0 [M+H]$^+$.

Synthesis of 1677-D.

A mixture of 6-chloro-3-nitropyridin-2-amine (670 mg, 3.75 mmol), 2-(5-fluorothiophen-2-yl)-4,4,5,5-tetramethyl-1,3,2-dioxaborolane (898 mg, 3.94 mmol) and K$_2$CO$_3$ (1.55 g, 11.25 mmol) in dioxane/H$_2$O (25 mL/2.5 mL) was treated with Pd(PPh$_3$)$_4$ (216 mg, 0.19 mmol) under a N$_2$ atmosphere. The reaction mixture was stirred at 95° C. for 3 h and then concentrated in vacuo. The crude residue was dissolved with EtOAc (200 mL) and the resulting solution was washed with brine (100 mL×3). The organic layer was dried over anhydrous Na$_2$SO$_4$ and then concentrated in vacuo. The residue was purified by column chromatography on silica gel (PE:EtOAc=7:1~5:1) to give 1677-D (900 mg, 93%) as a yellow solid. MS 240.1 [M+H]$^+$.

Synthesis of 1677-E.

To a stirred solution of 1677-D (460 mg, 1.92 mmol) in pyridine (10 mL) was added phenyl carbonochloridate (900 mg, 5.77 mmol) dropwise. After the addition was completed, the mixture was stirred at 55° C. for 2 h. The mixture was concentrated in vacuo. The residue was purified by column chromatography on silica gel (PE:DCM=20:1~1:3) to give 1677-E (700 mg, 76%) as a yellow solid. MS 479.8 [M+H]$^+$.

Synthesis of 1677-F.

To a solution of 1677-E (200 mg, 0.42 mmol) and 1677-C (116 mg, crude product) in DMSO (5 mL) was added NaHCO$_3$ (352 mg, 4.2 mmol). The reaction mixture was stirred at room temperature for 2 h, whereupon the mixture was diluted with water (50 mL), and extracted with EtOAc (20 mL×3). The combined organic layers were washed with brine (20 mL×3), dried over anhydrous Na$_2$SO$_4$ and then concentrated in vacuo. The residue was purified by Prep-TLC (EA:PE=5:1) to give 1677-F (80 mg, 48%) as a brown solid. MS 400.9 [M+H]$^+$.

Synthesis of Compound 2.

A mixture of 1677-F (68 mg, 0.17 mmol) and Raney Ni (20 mg) in DCM/MeOH (3 mL/5 mL) was stirred at room temperature for 0.5 h. The Ni was then removed by filtration through Celite, the filtrate was concentrated, and the crude residue was purified by Prep-TLC (DCM:MeOH=10:1) to give Compound 2 (20 mg, 27%) as a gray solid. MS 371.2 [M+H]$^+$.

Example 3

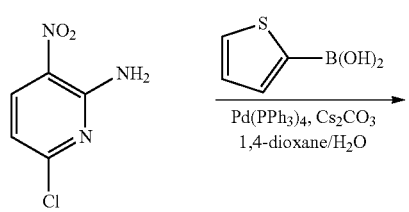

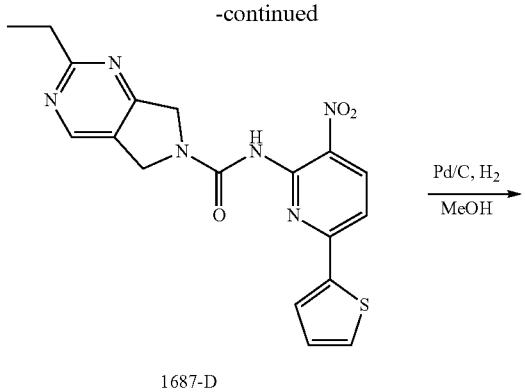

1687-D

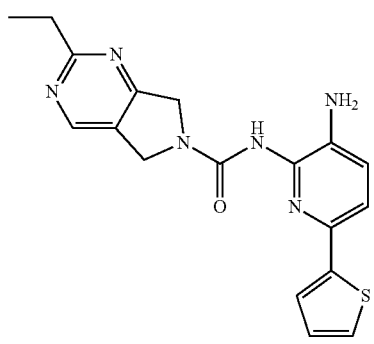

Compound 3

Synthesis of SM-H.

A mixture of 6-chloro-3-nitropyridin-2-amine (10.00 g, 57.6 mmol), thiophen-2-ylboronic acid (8.12 g, 63.4 mmol) and $Cs_2CO_3$ (37.56 g, 115.2 mmol) in dioxane/$H_2O$ (200 mL/20 mL) was treated with $Pd(PPh_3)_4$ (2.44 g, 2.88 mmol) under a $N_2$ atmosphere. The reaction mixture was stirred at 95° C. for 2 h and then concentrated in vacuo. The crude residue was dissolved with EtOAc (200 mL) and the resulting solution was washed with brine (100 mL×3). The organic layer was dried over anhydrous $Na_2SO_4$ and then concentrated in vacuo. The residue was purified by column chromatography on silica gel (PE:EtOAc=5:1~3:1) to give SM-H (10.0 g, 79%) as a yellow solid. MS 222.2 $[M+H]^+$.

Synthesis of SM-J.

To a solution of SM-H (1.30 g, 5.88 mmol) in pyridine (20 mL) was added phenyl carbonochloridate (2.29 g, 14.7 mmol) dropwise. After the addition was completed, the mixture was heated to 50° C. and stirred at that temperature for 4 h. The mixture was then concentrated in vacuo, and the crude residue was purified by column chromatography on silica gel (PE:EtOAc=8:1~3:1) to give SM-J (2.4 g, 89%) as a yellow solid. MS 462.4 $[M+H]^+$.

Synthesis of 1687-A.

A solution of tert-butyl 3-oxopyrrolidine-1-carboxylate (4.0 g, 21.6 mmol) and DMF-DMA (7.6 g, 64.8 mmol in THF (40 mL) was stirred at 70° C. for 16 h. The solution was concentrated in vacuo to give 1687-A as a crude product which was used directly in the next step without purification. MS 241.3 $[M+H]^+$.

Synthesis of 1687-B.

To a solution of 1687-A (8.2 mmol, crude product from last step) in EtOH (10 mL) was added $Et_3N$ (4.1 g, 41.0 mmol) and propionimidamide hydrochloride (3.55 g, 32.8 mmol). The resulting reaction mixture was stirred at 80° C. for 24 h. After the mixture was cooled to room temperature, the mixture was diluted with water (50 mL) and extracted with DCM (30 mL×3). The combined organic layers were washed with brine (30 mL×3), dried over anhydrous $Na_2SO_4$ and then concentrated in vacuo. The crude residue was purified by column chromatography on silica gel (PE:DCM=10:1~1:2) to give 1687-B (1.0 g, 49%) as a brown solid. MS 250.3 $[M+H]^+$.

Synthesis of 1687-C.

To a solution of 1687-B (1.0 g, 4.02 mmol) in DCM (10 mL) was added TFA (5 mL) dropwise. The reaction mixture was stirred at room temperature for 1 h, and then the solution was concentrated in vacuo to give 1687-C as a crude product which was used directly in the next step without purification. MS 150.3 $[M+H]^+$.

Synthesis of 1687-D.

A mixture of SM-J (292 mg, 0.63 mmol) and 1687-C (0.82 mmol) in DMSO (8 mL) was treated with $Na_2CO_3$ (537 mg, 5.07 mmol), and the resulting reaction mixture was stirred at room temperature for 2 h. The mixture was then diluted with water (20 mL), extracted with EtOAc (20 mL×3), and the combined organic layers were washed with brine (20 mL×3), dried over anhydrous $Na_2SO_4$ and then concentrated in vacuo. The crude residue was purified by column chromatography on silica gel (DCM:MeOH=100:1~50:1) to give 1687-D (150 mg, 60%) as a yellow solid. MS 397.4 $[M+H]^+$.

Synthesis of Compound 3.

A mixture of 1687-D (100 mg, 0.25 mmol) and Pd/C (100 mg) in MeOH (10 mL) was stirred under a $H_2$ atmosphere (1 atm) at room temperature for 1 h. The Pd/C was then removed by filtration through Celite, the filtrate was concentrated, and the crude residue was purified by Prep-TLC (DCM:MeOH=10:1) to give Compound 3 (45 mg, 49%) as a yellow solid (MS 367.4 $[M+H]^+$).

Example 4

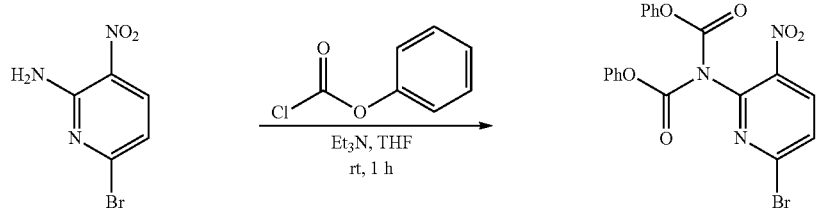

SM-E

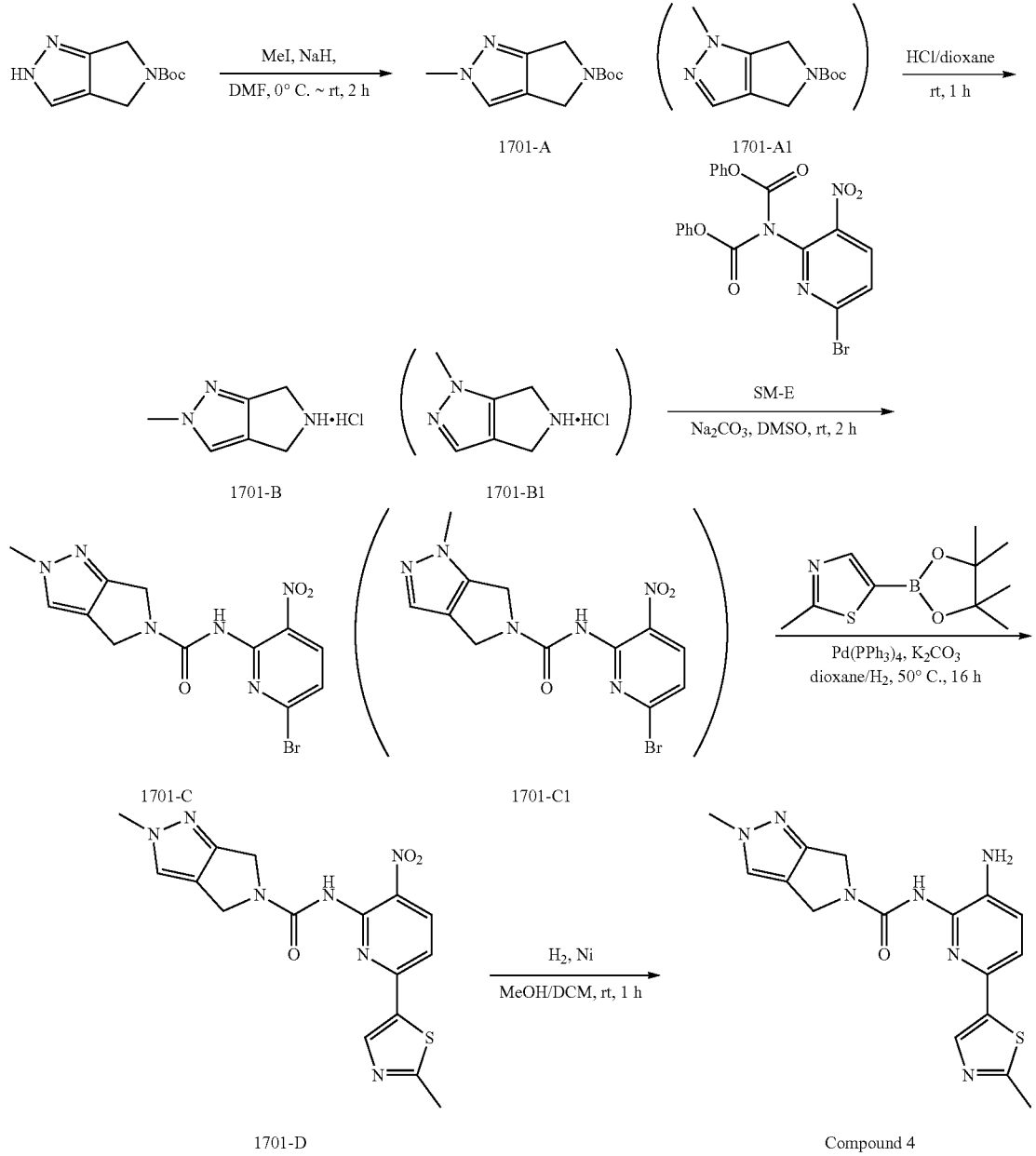

Synthesis of SM-E.

To a solution of 6-bromo-3-nitropyridin-2-amine (5.0 g, 23.0 mmol) and Et₃N (6.9 g, 69.0 mmol) in THF (60 mL) cooled to 0° C. was added phenyl carbonochloridate (10.8 g, 69.0 mmol) dropwise. After the addition was completed, the mixture was allowed to warm to room temperature, and was stirred at room temperature for 1 h. After 1 h, the reaction mixture was filtered and concentrated in vacuo. The residue was recrystallized from petroleum ether to give SM-E (10.2 g, 97%) as a light yellow solid. MS 458.0, 460.0 [M+H]⁺.

Synthesis of 1701-A and 1701-A1.

To a solution of tert-butyl 4,6-dihydropyrrolo[3,4-c] pyrazole-5(2H)-carboxylate (1.00 g, 4.78 mmol) in DMF (10 mL) cooled to 0° C. was added NaH (60% in mineral oil) (420 mg, 10.5 mmol), and the resulting reaction mixture was allowed to warm to room temperature and stirred at room temperature for 30 min. At this point, MeI (814 mg, 5.74 mmol) was added into the reaction mixture and stirring at room temperature was continued for 2 h. The reaction was then quenched with water (50 mL), extracted with EtOAc (30 mL×3), and the combined organic layers were washed with brine (10 mL×3), dried over anhydrous Na₂SO₄ and then concentrated in vacuo to give crude 1701-A and 1701-A1 (920 mg, 86%) as a yellow oil. The crude product was taken on to the next step without further purification. MS 224.1 [M+H]⁺.

Synthesis of 1701-B and 1701-B1.

To a round bottomed flask containing a mixture of 1701-A and 1701-A1 (920 mg, 4.13 mmol) and cooled with an ice bath was added HCl/1,4-dioxane (4N, 10 mL). The reaction mixture was stirred at room temperature for 1 h. The solvent was then removed in vacuo to give 1701-B and 1701-B1 as a crude product which was taken on to the next step without purification. MS 124.1 [M+H]⁺.

Synthesis of 1701-C.

To a solution of 1701-B and 1701-B1 (crude product from last step) and SM-E (800 mg, 1.75 mmol) in DMSO (10 mL) was added Na$_2$CO$_3$ (1.48 g, 13.97 mmol). The mixture was stirred at room temperature for 4 h. The mixture was diluted with water (50 mL), extracted with EtOAc (20 mL×3). The combined organic layer was washed with brine (20 mL×3), dried over anhydrous Na$_2$SO$_4$ and then concentrated in vacuo. The residue was purified by column chromatography on silica gel (DCM:MeOH=100:1~30:1) to give 1701-C and 1701-C1 as a yellow solid. The regioisomers were then separated by Prep-TLC (DCM:EA=4:1) to give 1701-C (150 mg, 23%) as a yellow solid. MS 367.0, 369.0 [M+H]$^+$.

Synthesis of 1701-D.

A mixture of 1701-C (150 mg, 0.41 mmol), 2-methyl-5-(4,4,5,5-tetramethyl-1,3,2-dioxaborolan-2-yl)thiazole (120 mg, 0.53 mmol) and K$_2$CO$_3$ (169 mg, 1.23 mmol) in dioxane/H$_2$O (10 mL/2 mL) was treated with Pd(PPh$_3$)$_4$ (23.6 mg, 0.02 mmol) under a N$_2$ atmosphere. The reaction mixture was stirred at 50° C. for 16 h, and was then concentrated in vacuo. The crude residue was dissolved with EtOAc (20 mL), and the resulting solution was washed with brine (10 mL×3). The organic layer was dried over anhydrous Na$_2$SO$_4$ and then concentrated in vacuo. The crude residue was purified by Prep-TLC (DCM:MeOH=20:1) to give 1701-D (90 mg, 57%) as a yellow solid. MS 386.4 [M+H]$^+$.

Synthesis of Compound 4.

A mixture of 1701-D (90 mg, 0.23 mmol) and Raney Ni (90 mg) in MeOH/DCM (10 mL/2 mL) was stirred under a H$_2$ atmosphere (1 atm) at room temperature for 1 h. The Raney Ni was then removed by filtration through Celite, the filtrate was concentrated, and the crude residue was purified by Prep-TLC (DCM:MeOH=10:1) to give Compound 4 (25 mg, 31%) as a gray solid (MS 356.4 [M+H]$^+$).

Example 5

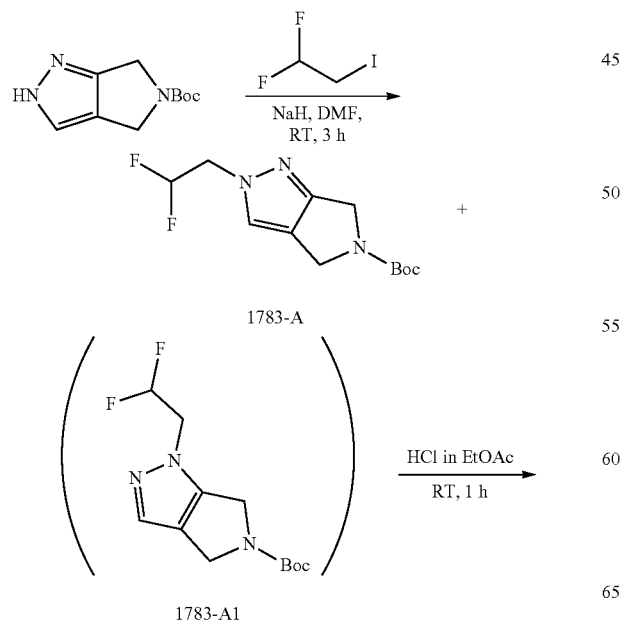

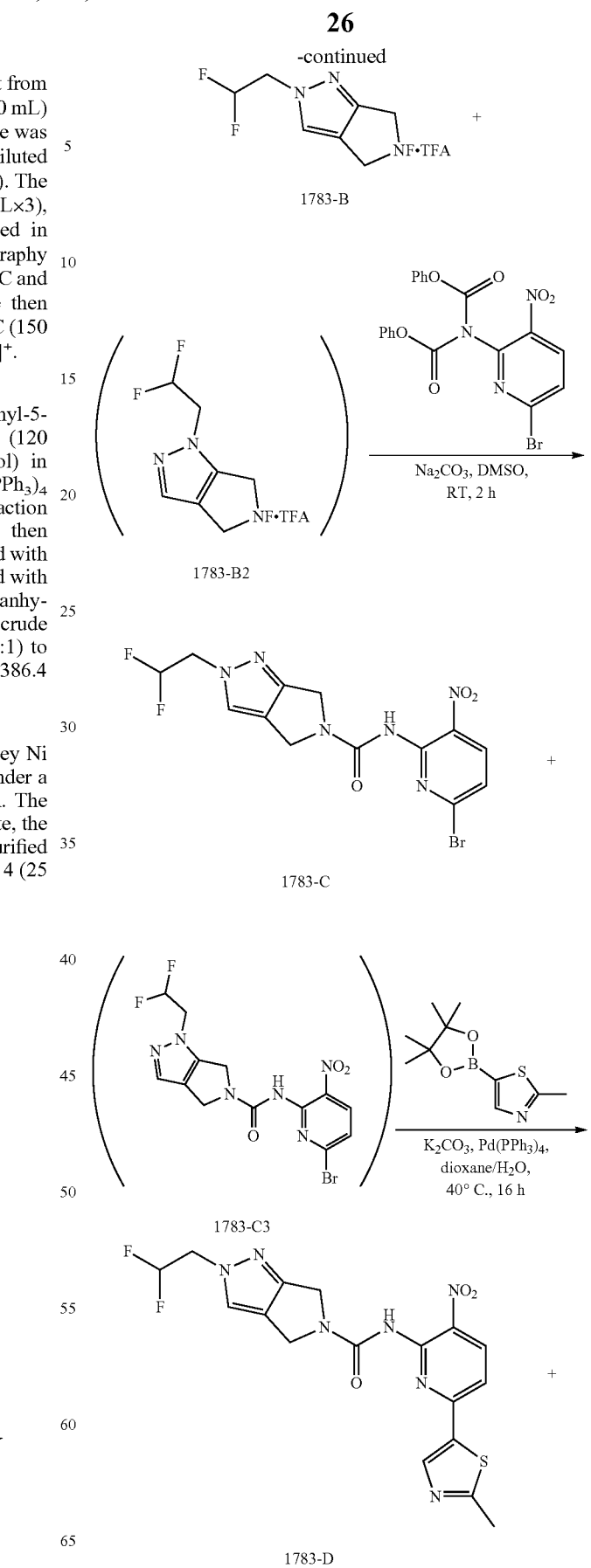

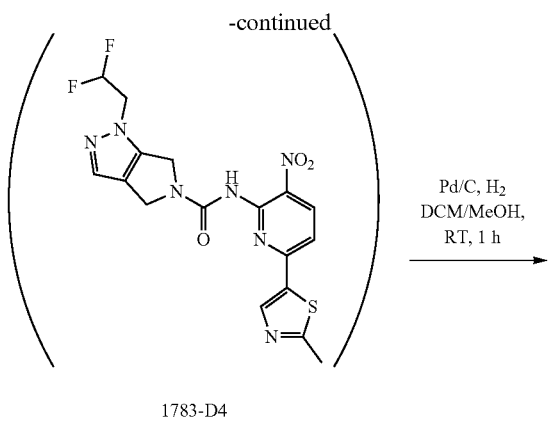

1783-D4

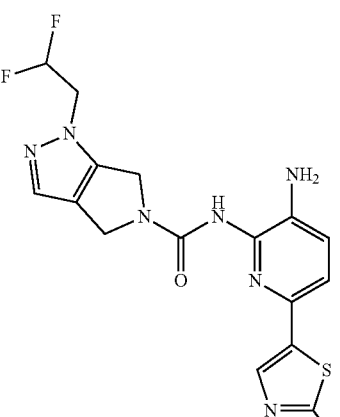

Compound 5

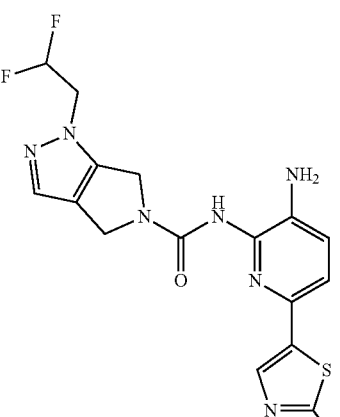

T-1783-A

Synthesis of 1783-A and 1783-A1.

A solution of tert-butyl 4,6-dihydropyrrolo[3,4-c] pyrazole-5(2H)-carboxylate (600 mg, 2.88 mmol) in DMF (8 mL) was cooled to 0° C., and then was treated with NaH (60% in mineral oil) (184 mg, 4.6 mmol). The reaction was allowed to warm to room temperature, was stirred at room temperature for 30 min, and then 1,1-difluoro-2-iodoethane (829 mg, 4.32 mmol) was added. After stirring at room temperature for 3 h, the mixture was quenched with water (45 mL) and extracted with EtOAc (14 mL×3). The combined organic layers were washed with brine (10 mL×3), dried over anhydrous $Na_2SO_4$ and then concentrated in vacuo. The crude residue was purified by column chromatography on silica gel (PE:EtOAc=3:1~3:2) to give a mixture of 1783-A and 1783-A1 (520 mg, 66%) as a white solid. MS 274.1 $[M+H]^+$.

Synthesis of 1783-B and 1783-B1.

A mixture of 1783-A and 1783-A1 (520 mg, 1.9 mmol) was treated with HCl/EtOAc (4 M, 16 mL), and the reaction mixture was stirred at room temperature for 1 h. The solvent was then removed in vacuo to give a mixture of 1783-B and 1783-B1 (460 mg, 98%) as gray solid which was taken on to the next step without purification. MS 174.0 $[M+H]^+$.

Synthesis of 1783-C and 1783-C1.

A solution of the regioisomeric mixture of 1783-B and 1783-B1 (460 mg, 1.87 mmol) and SM-E (450 mg, 0.98 mmol) in DMSO (10 mL) was treated with $Na_2CO_3$ (1.04 g, 9.8 mmol). The reaction mixture was stirred at room temperature for 2 h, then was diluted with water (60 mL), and extracted with EtOAc (15 mL×4). The combined organic layers were washed with brine (13 mL×3), dried over anhydrous $Na_2SO_4$ and then concentrated in vacuo. The crude residue was purified by column chromatography on silica gel (DCM:MeOH=60:1~45:1) to give a mixture of 1783-C and 1783-C1 (380 mg, 92%) as a yellow solid. MS 417.0 $[M+H]^+$.

Synthesis of 1783-D and 1783-D1.

A mixture of 1783-C and 1783-C1 (380 mg, 0.91 mmol), 2-methyl-5-(4,4,5,5-tetramethyl-1,3,2-dioxaborolan-2-yl) thiazole (278 mg, 1.09 mmol) and $K_2CO_3$ (264 mg, 1.91 mmol) in dioxane/$H_2O$ (14 mL/2 mL) was treated with $Pd(PPh_3)_4$ (81 mg, 0.07 mmol) under a $N_2$ atmosphere. The reaction mixture was stirred at 40° C. overnight, and was then concentrated in vacuo. The crude residue was dissolved with DCM (50 mL), washed with brine (15 mL×3), the organic layer was dried over anhydrous $Na_2SO_4$ and then concentrated in vacuo. The crude residue was purified by column chromatography on silica gel (DCM:MeOH=50: 1~30:1) to give a mixture 1783-D and 1783-D1 (240 mg, 61%) as a brown solid. MS 436.2 $[M+H]^+$.

Synthesis of Compound 5.

A mixture of 1783-D and 1783-D1 (240 mg, 0.55 mmol) and Pd/C (200 mg) in MeOH/DCM (30 mL/10 mL) was stirred under a $H_2$ atmosphere (1 atm) at room temperature for 1 h. The Pd/C was then removed by filtration through Celite, the filtrate was concentrated, and the resulting crude residue was purified via HPLC to separate the regioisomers using chiral chromatography (Column: Chiralcel OJ-3; Solvent: MeOH; Flow rate: 2 mL/min; $RT_{1783}$=2.146 min, $RT_{1641A}$=1.363 min) to give Compound 5 (32 mg, 21%) as a white solid. MS 406.1 $[M+H]^+$.

Example 6
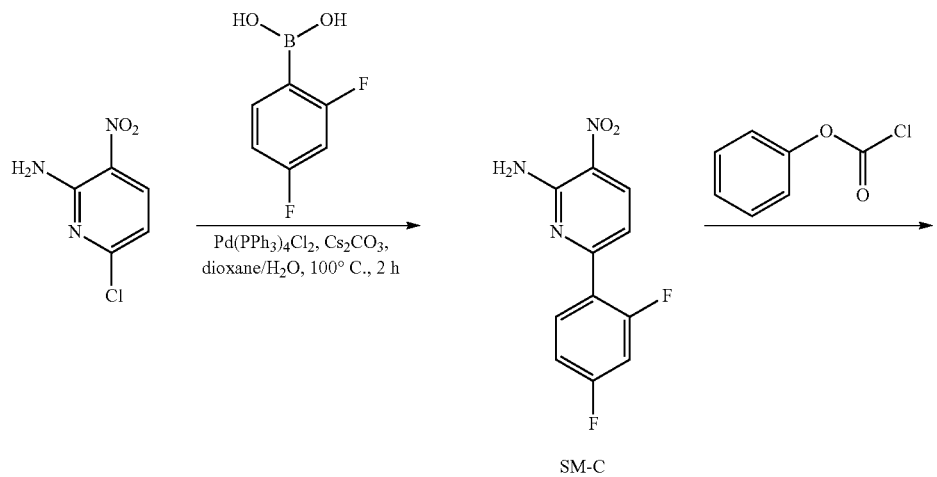
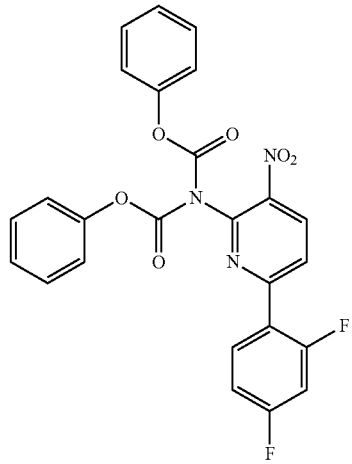
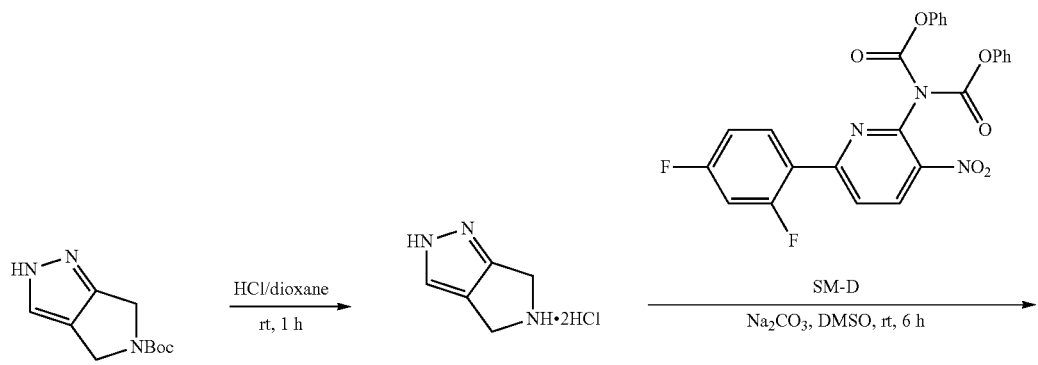

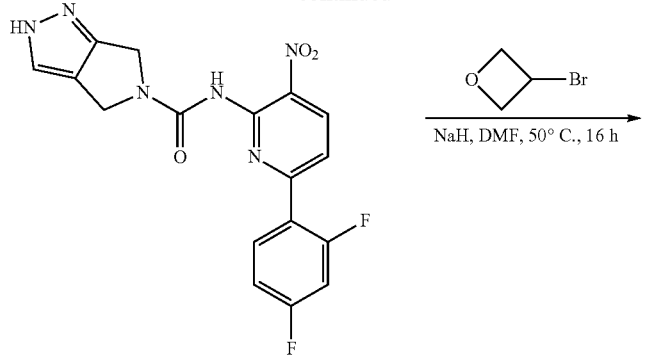

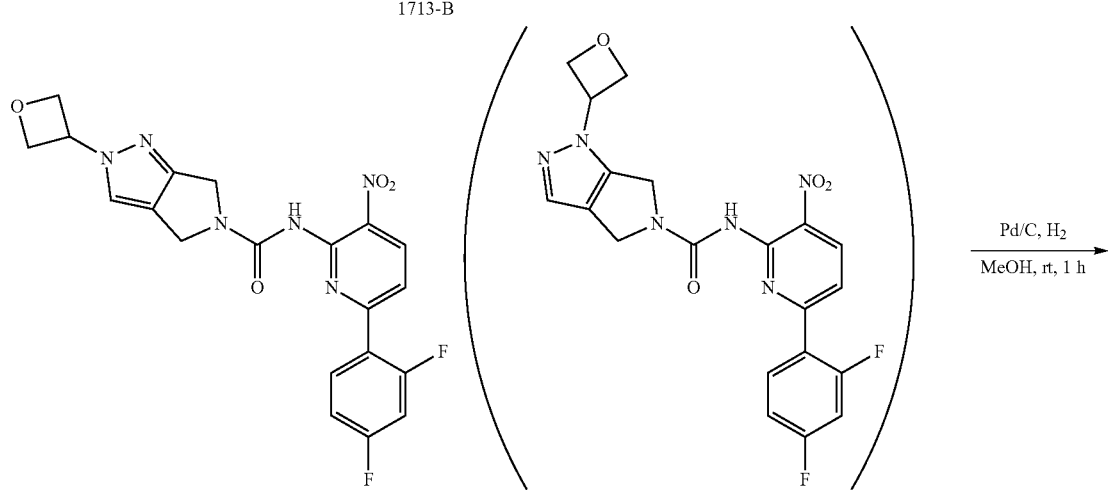

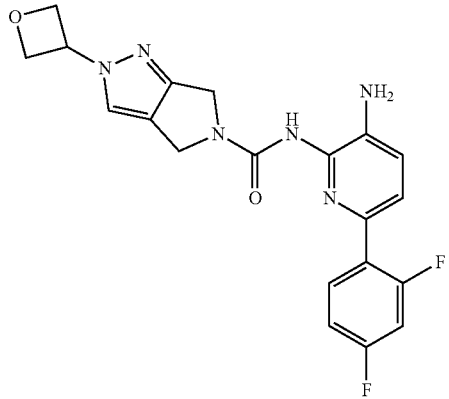

Synthesis of SM-C.

A mixture of 6-chloro-3-nitropyridin-2-amine (4.58 g, 26.4 mmol), 2,4-difluorophenylboronic acid (5.00 g, 31.7 mmol) and $Cs_2CO_3$ (25.73 g, 79.2 mmol) in dioxane/$H_2O$ (100 mL/10 mL) was treated with $Pd(PPh_3)_4$ (1.10 g, 0.95 mmol) under a $N_2$ atmosphere. The mixture was stirred at 100° C. for 2 h and then concentrated in vacuo. The residue was dissolved with EtOAc (200 mL) and the solution was washed with brine (100 mL×3). The organic layer was dried over anhydrous $Na_2SO_4$ and then concentrated in vacuo. The residue was purified by column chromatography on silica gel (PE:EtOAc=7:1~5:1) to give SM-C (4.0 g, 61%) as a yellow solid. MS 252.1 $[M+H]^+$.

Synthesis of SM-D.

A solution of SM-C (4.0 g, 15.94 mmol) in pyridine (60 mL) was cooled to 0° C., and then phenyl carbonochloridate (7.50 g, 47.81 mmol) was added dropwise. After the addition was completed, the mixture was heated to 50° C., and was stirred at 50° C. for 4 h. The mixture was then cooled to room temperature and was concentrated in vacuo. The crude residue was purified by column chromatography on silica gel (PE:DCM=3:2~1:1) to give SM-D (7.1 g, 91%) as a yellow solid. MS 492.1 [M+H]$^+$.

Synthesis of 1713-A.

A solution of tert-butyl 4,6-dihydropyrrolo[3,4-c] pyrazole-5(2H)-carboxylate (205 mg, 0.98 mmol) in HCl/dioxane (4N, 8 mL) was stirred at room temperature for 1 h. The solvent was removed in vacuo to give 1713-A as a crude product which was taken on to the next step without further purification. MS 110.1 [M+H]$^+$.

Synthesis of 1713-B.

A mixture of 1713-A (crude product from last step) and SM-D (400 mg, 0.82 mmol) in DMSO (8 mL) was treated with Na$_2$CO$_3$ (691 mg, 6.52 mmol), and the resulting reaction mixture was stirred at room temperature for 2 h. The mixture was then diluted with water (20 mL), and extracted with EtOAc (20 mL×3). The combined organic layers were washed with brine (20 mL×3), dried over anhydrous Na$_2$SO$_4$ and then concentrated in vacuo. The residue was purified by column chromatography on silica gel (DCM:MeOH=100:1~50:1) to give 1713-B (270 mg, 86%) as a yellow solid. MS 387.1 [M+H]$^+$.

Synthesis of 1713-C and 1713-C1.

A solution of 1713-B (215 mg, 0.56 mmol) in DMF (3 mL) was cooled to 0° C. and then was treated with NaH (60% in mineral oil) (67 mg, 1.68 mmol). The resulting reaction mixture was allowed to warm to room temperature, and was stirred at room temperature for 30 min. After 30 min, 3-bromooxetane (92 mg, 0.67 mmol) was added, and the reaction mixture was stirred at 50° C. overnight. The mixture was then cooled to room temperature and was quenched with water (20 mL), then extracted with EtOAc (20 mL×3). The combined organic layers were washed with brine (10 mL×3), dried over anhydrous Na$_2$SO$_4$ and then concentrated in vacuo. The residue was purified by column chromatography on silica gel (DCM:MeOH=100:1~30:1) to give a mixture 1713-C and 1713-C1 (65 mg, 26%) isolated as a yellow solid. MS 443.1 [M+H]$^+$.

Synthesis of Compound 6 and T-1713A.

A mixture of 1713-C and 1713-C1 (65 mg, 0.15 mmol) and Pd/C (65 mg) in MeOH (5 mL) was stirred under a H$_2$ atmosphere (1 atm) at room temperature for 1 h. The Pd/C was then removed by filtration through Celite, the filtrate was concentrated, and the crude residue was purified by HPLC, using chiral chromatography (Column: Chiralcel OD-3; Solvent: MeOH; Flow rate: 2 mL/min; RT$_{1713}$=2.45 min, RT$_{1713A}$=3.99 min) to give Compound 6 (10 mg, 16%) as a white solid (MS 413.2 [M+H]$^+$) and T-1713A (5 mg, 8%) as a white solid. MS 413.1 [M+H]$^+$.

Example 7

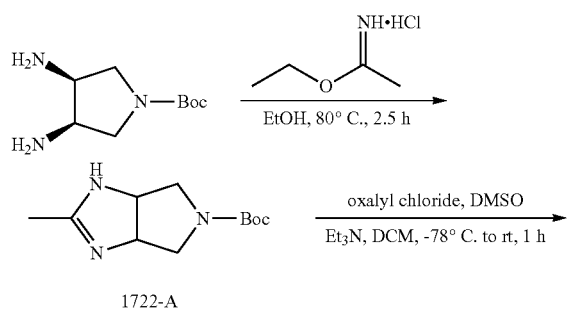

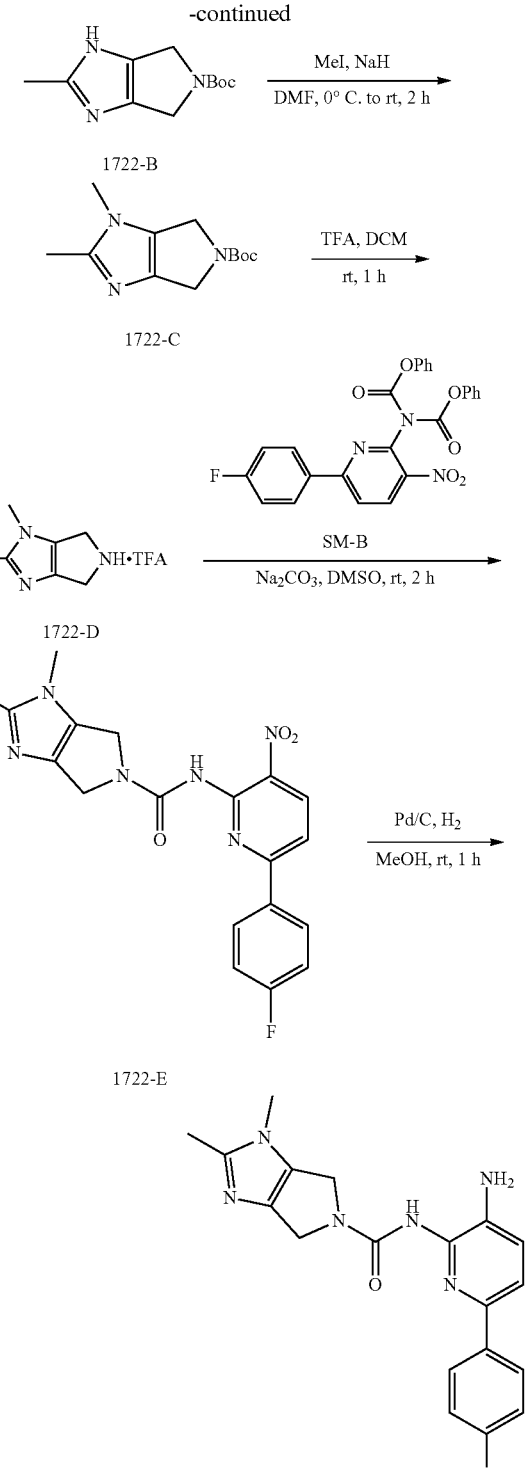

Compound 7

Synthesis of 1722-A.

To a solution of (3R,4S)-tert-butyl 3,4-diaminopyrrolidine-1-carboxylate (3.3 g, 16.4 mmol) in anhydrous ethanol (80 mL) was added ethyl acetimidate hydrochloride (2.65 g, 21.3 mmol), and the reaction mixture was stirred at 80° C. for 2.5 h. The mixture was evaporated in vacuo and the residue was purified by column chromatography on silica gel (DCM:MeOH=50:1~20:1) to give the 1722-A (3.0 g, 81%) as a brown oil. MS 226.4 [M+H]$^+$.

Synthesis of 1722-B.

To a stirred solution of oxalyl chloride (2.69 g, 21.3 mmol) in DCM (48 mL) at −78° C. was added a solution of DMSO (3.16 g, 42.6 mmol) in DCM (24 mL) dropwise. The resulting reaction mixture was stirred for 10 min, and then a solution of 1722-A (3 g, 13.3 mmol) in DCM (24 mL) was added dropwise over 10 min, followed by triethylamine (6.73 g, 66.7 mmol), which was added dropwise over 10 min. The reaction mixture was stirred with gradual warming for 1 h. The reaction was then quenched with water (100 mL), and the organic phase was washed with brine (30 mL×3), dried over Na$_2$SO$_4$ and concertrated in vacuo. The crude residue was purified by flash chromatography on silica gel (DCM:MeOH=50:1~20:1) to give 1722-B (1.5 g, 51%) as a white solid. MS 224.4 [M+H]$^+$.

Synthesis of 1722-C.

A solution of 1722-B (300 mg, 1.35 mmol) in DMF (6 mL) was cooled to 0° C., and then treated with NaH (60% in mineral oil) (81 mg, 2.03 mmol). The reaction was allowed to warm to room temperature, and was stirred at room temperature for 30 min. After 30 min, MeI (383 mg, 2.70 mmol) was added to the reaction mixture, and stirring at room temperature was continued for 2 h. The reaction mixture was then quenched with water (50 mL), extracted with EtOAc (30 mL×3), and the combined organic layers were washed with brine (10 mL×3), dried over anhydrous Na$_2$SO$_4$ and then concentrated in vacuo to give 1722-C (350 mg) as a crude product which was taken on without further purification. MS 238.2 [M+H]$^+$.

Synthesis of 1722-D.

To a solution of 1722-C (350 mg, crude product from last step) in DCM (6 mL) cooled to 0° C. was added TFA (3 mL) dropwise. The resulting reaction mixture was stirred at room temperature for 1 h, and the solvent was removed in vacuo to give 1722-D (360 mg) as a crude product which was taken on to the next step without further purification. MS 138.4 [M+H]$^+$.

Synthesis of 1722-E.

A mixture of 1722-D (150 mg, crude product from last step) and SM-B (249 mg, 0.53 mmol) in DMSO (5 mL) was treated with Na$_2$CO$_3$ (561 mg, 5.3 mmol), and the reaction mixture was stirred at room temperature for 2 h. The mixture was then diluted with water (30 mL), extracted with EtOAc (20 mL×3), and the combined organic layers were washed with brine (10 mL×3), dried over anhydrous Na$_2$SO$_4$ and then concentrated in vacuo. The residue was purified by Prep-TLC (EA:PE=5:1) to give 1722-E (30 mg, 14%) as a light yellow solid. MS 397.2 [M+H]$^+$.

Synthesis of Compound 7.

A mixture of 1722-E (30 mg, 0.076 mmol) and Pd/C (10 mg) in MeOH (4 mL) was stirred under a H$_2$ atmosphere (1 atm) at room temperature for 1 h. The Pd/C was then removed by filtration through Celite, the filtrate was concentrated, and the residue was purified by Prep-TLC (EA: MeOH=10:1) to give Compound 7 (5 mg, 18%) as a light yellow solid. MS 3672 [M+H]$^+$.

Example 8

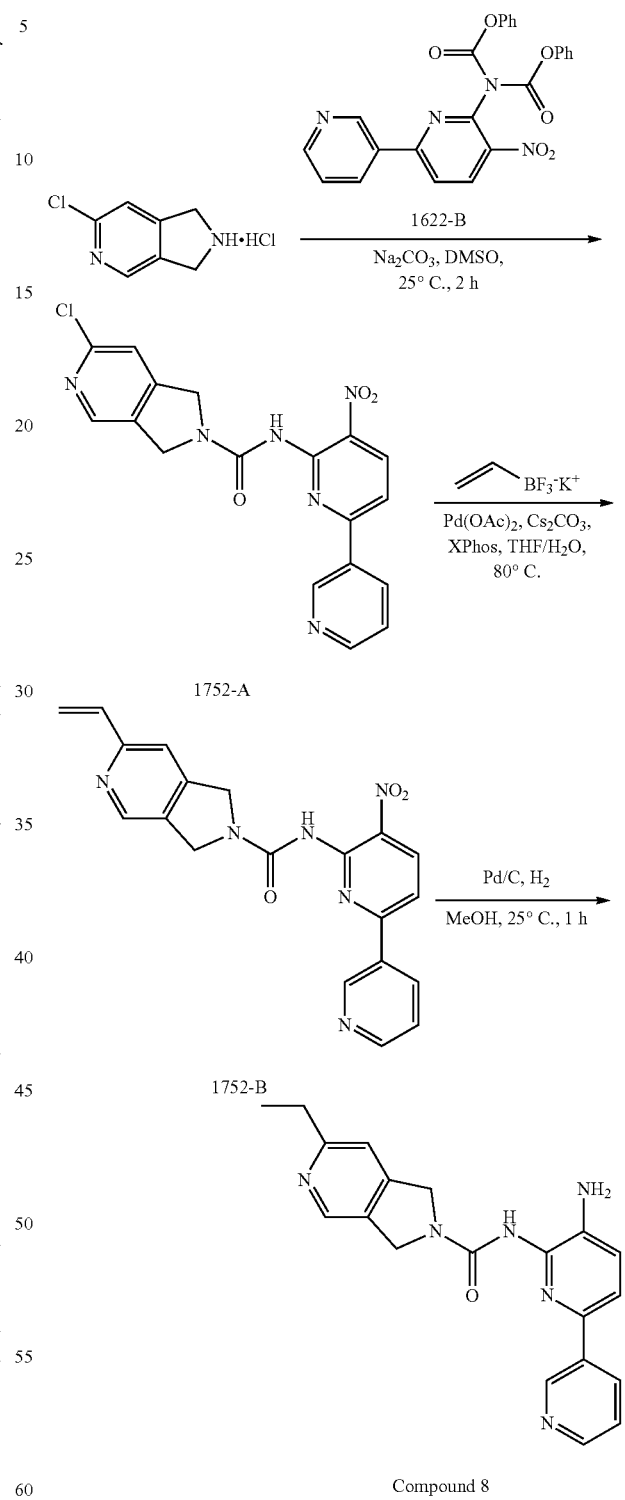

Synthesis of 1752-A.

A mixture of 1622-B (300 mg, 0.658 mmol) and 6-chloro-2,3-dihydro-1H-pyrrolo[3,4-c]pyridine hydrochloride (151 mg, 0.789 mmol) in DMSO (10 mL) was treated with Na$_2$CO$_3$ (558 mg, 5.263 mmol) and the reaction mixture was stirred at 25° C. for 2 h. The mixture was then diluted with water (20 mL), and extracted with EtOAc (20 mL×3). The combined organic layers were washed with brine (20 mL×3), dried over anhydrous Na₂SO₄ and then concentrated in vacuo. The residue was purified by column chromatography on silica gel (DCM:MeOH=100:1~50:1) to give 1752-A (200 mg, 77%) as a yellow solid. MS 397.1 [M+H]⁺.

Synthesis of 1752-B.

A mixture of 1752-A (200 mg, 0.50 mmol), potassium trifluoro(vinyl)borate (135 mg, 1.01 mmol), X-phos (12 mg, 0.025 mmol) and Cs₂CO₃ (493 mg, 1.51 mmol) in 1,4-dioxane/H₂O (17 mL/3 mL) was treated with Pd(OAc)₂ (3 mg, 0.01 mmol) under a N₂ atmosphere. The mixture was stirred at 80° C. for 4 h, at which point LCMS indicated the reaction had gone to completion. The reaction mixture was then extracted with DCM (15 mL×3), and the combined organic layers were dried over anhydrous Na₂SO₄ and then concentrated in vacuo. The residue was purified by column chromatography on silica gel (DCM:MeOH=50:1~12:1) to give 1752-B (100 mg, 51%) as a yellow solid. MS 388.1 [M+H]⁺.

Synthesis of Compound 8.

A mixture of 1752-B (100 mg, 0.257 mmol) and Pd/C (100 mg) in MeOH (10 mL) was stirred under a H₂ atmosphere (1 atm) at 25° C. for 1 h. The Pd/C was then removed by filtration through Celite, the filtrate was concentrated, and the residue was purified by Prep-TLC (DCM:MeOH=10:1) to give Compound 8 (40 mg, 43%) as a gray solid. MS 361.2 [M+H]⁺.

Example 9

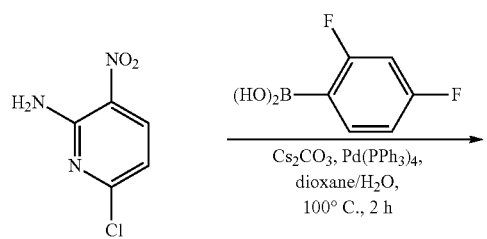

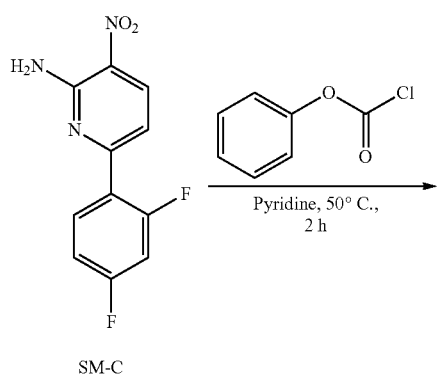

SM-C

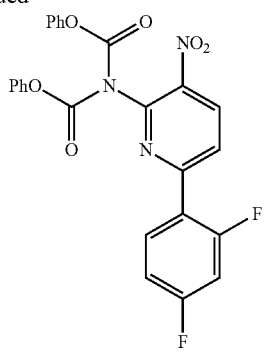

SM-D

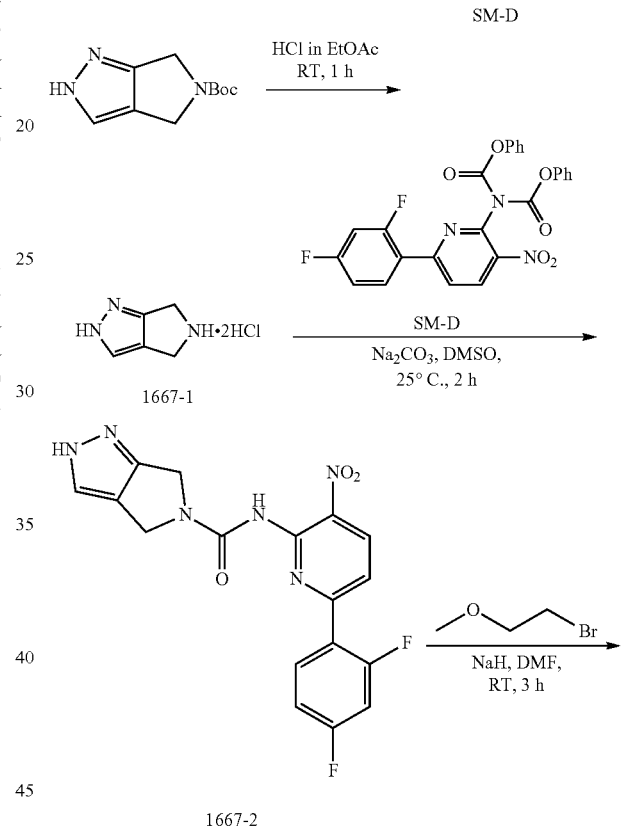

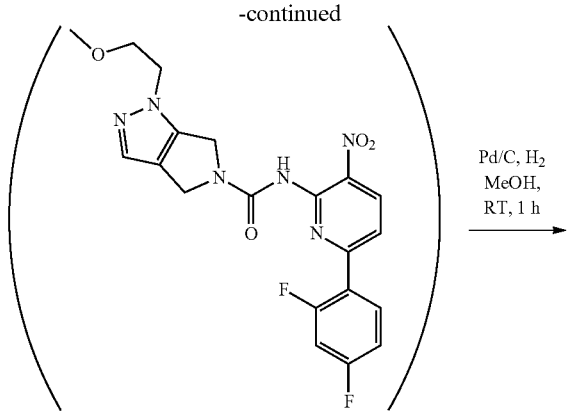

1667-3A

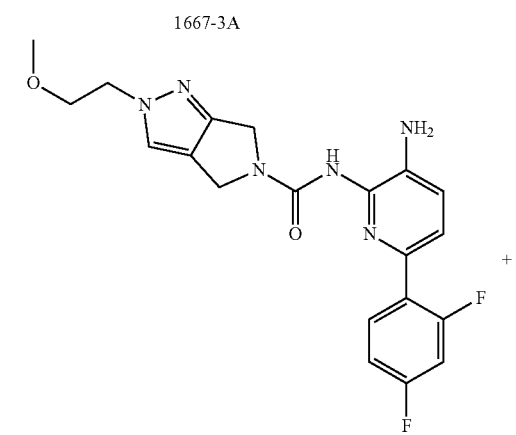

Compound 9

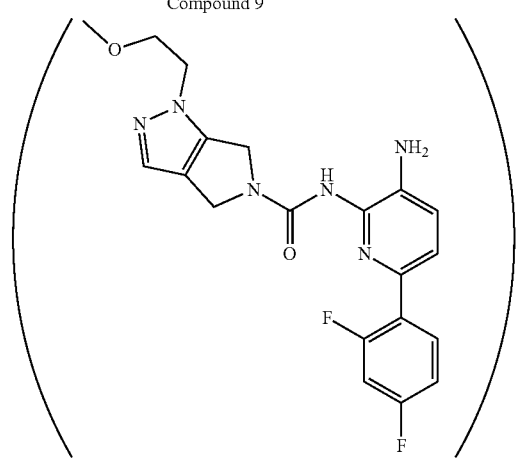

T-1667A

Synthesis of SM-C.

A mixture of 6-chloro-3-nitropyridin-2-amine (4.58 g, 26.4 mmol), 2,4-difluorophenylboronic acid (5.00 g, 31.7 mmol) and $Cs_2CO_3$ (25.73 g, 79.2 mmol) in dioxane/$H_2O$ (100 mL/10 mL) was treated with $Pd(PPh_3)_4$ (1.10 g, 0.95 mmol) under a $N_2$ atmosphere. The mixture was stirred at 100° C. for 2 h and then concentrated in vacuo. The residue was dissolved with EtOAc (200 mL) and the resulting solution was washed with brine (100 mL×3). The organic layer was dried over anhydrous $Na_2SO_4$ and then concentrated in vacuo. The residue was purified by column chromatography on silica gel (PE:EtOAc=7:1~5:1) to give SM-C (4.0 g, 61%) as a yellow solid. MS 252.1 $[M+H]^+$.

Synthesis of SM-D.

A stirred solution of SM-C (4.0 g, 15.94 mmol) in pyridine (60 mL) was added phenyl carbonochloridate (7.50 g, 47.81 mmol) dropwise at 0° C. After the addition was completed, the mixture was stirred at 50° C. for 4 h. The mixture was concentrated in vacuo. The residue was purified by column chromatography on silica gel (PE:DCM=3:2~1:1) to give SM-D (7.1 g, 91%) as a yellow solid. MS 492.1 $[M+H]^+$.

Synthesis of 1667-1.

A solution of tert-butyl 4,6-dihydropyrrolo[3,4-c] pyrazole-5(2H)-carboxylate (205 mg, 0.98 mmol) in HCl/EA (4N, 8 mL) was stirred at room temperature for 1 h. The solvent was removed in vacuo to give 1667-1 as a crude product which was taken on to the next step without purification. MS 110.1 $[M+H]^+$.

Synthesis of 1667-2.

A mixture of 1667-1 (crude product from last step) and SM-D (400 mg, 0.82 mmol) in DMSO (8 mL) was treated with $Na_2CO_3$ (691 mg, 6.52 mmol), and the resulting reaction mixture was stirred at room temperature for 2 h. The mixture was diluted with water (20 mL), extracted with EtOAc (20 mL×3). The combined organic layers were washed with brine (20 mL×3), dried over anhydrous $Na_2SO_4$ and then concentrated in vacuo. The residue was purified by column chromatography on silica gel (DCM:MeOH=100:1~50:1) to give 1667-2 (270 mg, 86%) as a yellow solid. MS 387.1 $[M+H]^+$.

Synthesis of 1667-3 and 1667-3A.

A solution of 1667-2 (270 mg, 0.70 mmol) in DMF (5 mL) was cooled to 0° C. and then treated with NaH (60% in mineral oil) (84 mg, 2.10 mmol). The resulting reaction mixture was allowed to warm to room temperature, and then was stirred at room temperature for 30 min. After 30 min, 1-bromo-2-methoxyethane (194 mg, 1.40 mmol) was added to the reaction mixture, and stirring was continued at room temperature for 2 h. The mixture was then quenched with water (15 mL), and extracted with EtOAc (20 mL×3). The combined organic layers were washed with brine (10 mL×3), dried over anhydrous $Na_2SO_4$ and then concentrated in vacuo. The residue was purified by column chromatography on silica gel (DCM:MeOH=100:1~30:1) to give a mixture of 1667-3 and 1667-3A (300 mg, 97%) as a yellow solid. MS 445.0 $[M+H]^+$.

Synthesis of Compound 9 and T-1667A.

A mixture of 1667-3 and 1667-3A (300 mg, 0.68 mmol) and Pd/C (300 mg) in MeOH (15 mL) was stirred at room temperature for 1 h under a $H_2$ atmosphere (1 atm). The Pd/C was then removed by filtration through Celite, the filtrate was concentrated, and the residue was purified by column chromatography on silica gel (DCM:MeOH=100:1~30:1) to give Compound 8 and T-1667A. The mixture was then further purified by HPLC using chiral chromatography (Column: Chiralcel OJ-3; Solvent: MeOH/MeCN=1/1; Flow rate: 2 mL/min; $RT_{1667}$=1.74 min, $RT_{1667A}$=0.93 min) to give Compound 9 (80 mg, 28%) as a white solid (MS 415.1 $[M+H]'$) and T-1667A (40 mg, 14%) as a white solid. MS 415.1 $[M+H]^+$.

Example 10—Intentionally Omitted

Example 11

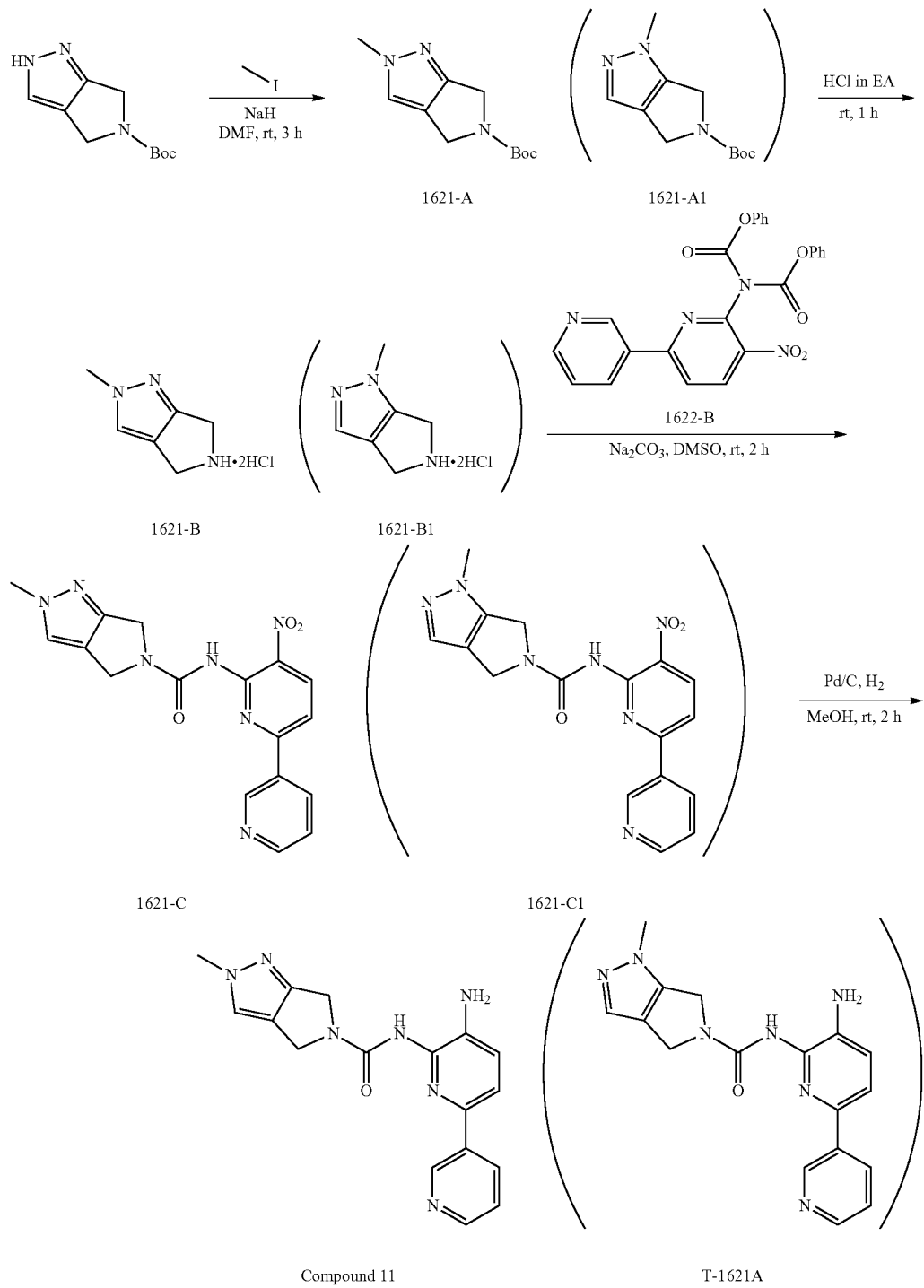

Compound 11                    T-1621A

Synthesis of 1621-A and 1621-A1.

A mixture of tert-butyl 4,6-dihydropyrrolo[3,4-c]pyrazole-5(2H)-carboxylate (350 mg, 1.67 mmol) and CH$_3$I (474 mg, 3.34 mmol) in dry DMF (5 mL) was cooled to 0° C., and then was treated with NaH (100 mg, 2.5 mmol, 60% w/w). The reaction mixture was allowed to warm to room temperature, and then was stirred at room temperature for 3 h, whereupon it was poured into ice water (30 mL) to quench. The mixture was extracted with EtOAc (3×12 mL), and the combined organic layers were combined and washed with brine (20 mL), dried over anhydrous Na$_2$SO$_4$ and then concentrated in vacuo. The residue was purified by column chromatography on silica gel (PE:EtOAc=4:1~3:2) to give a mixture of 1621-A and 1621-A1 (355 mg, 95.1%) as a colorless oil.

Synthesis of 1621-B and 1621-B1.

A mixture of 1621-A and 1621-A1 (355 mg, 1.59 mmol) was dissolved in HCl in EtOAc (4M, 12 mL), and the reaction mixture was stirred at room temperature for 1 h. When LCMS showed the reaction was finished, the solvent was removed in vacuo to give 1621-B and 1621-B1 (307 mg, 98.4%) as white solid which was taken on to the next step without further purification.

Synthesis of 1621-C and 1621-C1.

A mixture of 1621-B and 1621-B1 (270 mg, 1.38 mmol) and 1622-B (360 mg, 0.79 mmol) in DMSO (6 mL) was stirred at room temperature for 10 min, then Na$_2$CO$_3$ (670 mg, 6.32 mmol) was added, and the reaction mixture was stirred at room temperature for 2 h. After the reaction had gone to completion as indicated by LCMS, the mixture was diluted with water (40 mL) and extracted with EtOAc (3×12 mL). The combined organic layers were washed with brine (3×10 mL), dried over anhydrous Na$_2$SO$_4$ and then concentrated in vacuo. The residue was purified by column chromatography on silica gel (DCM:MeOH=100:1~60:1) to give a mixture of 1621-C and 1621-C1 (230 mg, 79.8%) as a yellow solid.

Synthesis of Compound 11 and 1621A.

A mixture of 1621-C and 1621-C1 (230 mg, 0.63 mmol) and Pd/C (230 mg) in MeOH (20 mL) was stirred at room temperature for 50 min under a H$_2$ atmosphere (1 atm). The Pd/C was then removed by filtration through Celite, the filtrate was concentrated, and the residue was purified by chiral HPLC (Column: Chiralcel OD-3; Solvent: MeOH; Flow rate: 2 mL/min; RT$_{1621}$=2.25 min, RT$_{1621A}$=3.07 min) to give Compound 11 (80 mg, 56.8%) as yellow solid and 1621A (40 mg, 56.8%) as yellow solid.

Example 12

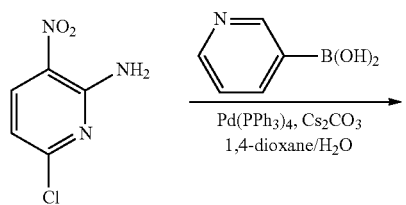

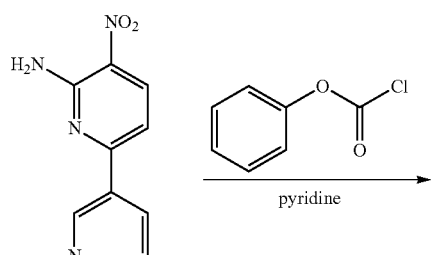

1622-A

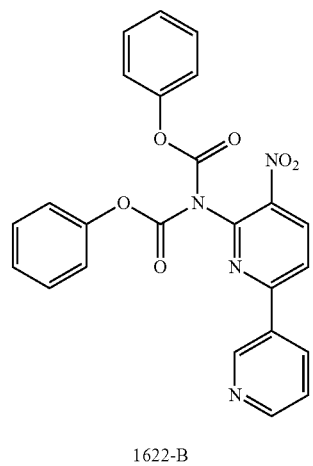

1622-B

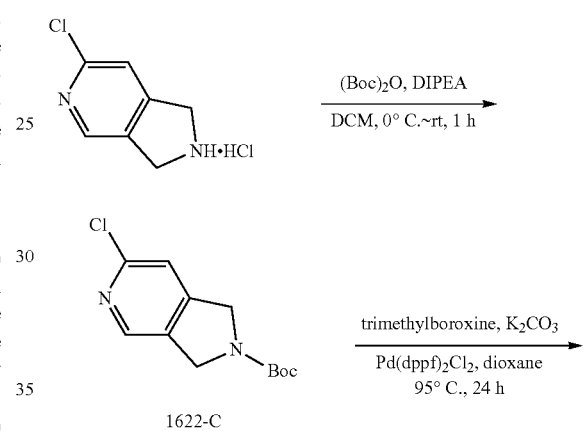

1622-C

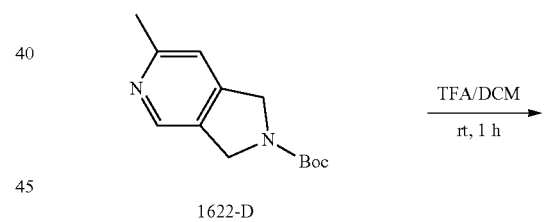

1622-D

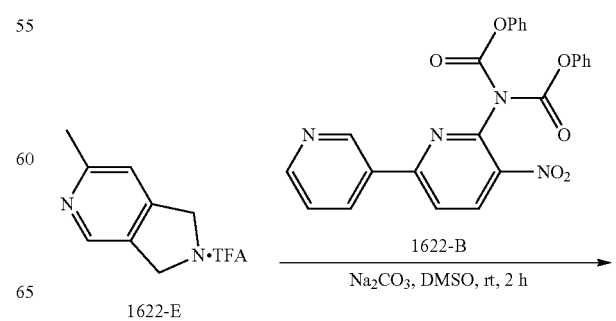

1622-E

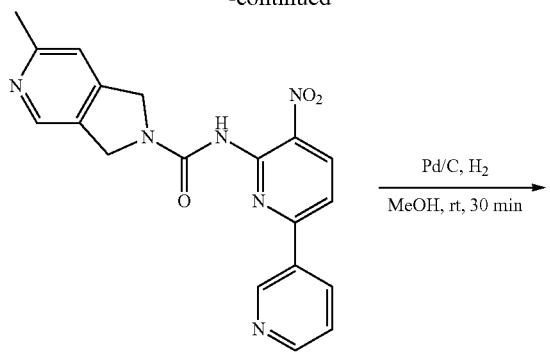

1622-F

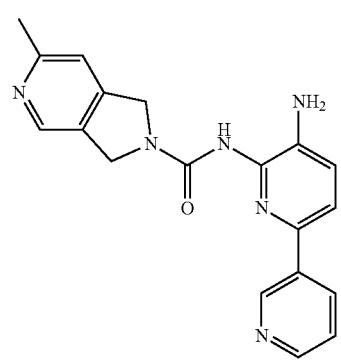

Compound 12

Synthesis of 1622-A.

A mixture of 6-chloro-3-nitropyridin-2-amine (9.00 g, 51.87 mmol), pyridin-3-ylboronic acid (7.66 g, 62.25 mmol) and $Cs_2CO_3$ (50.70 g, 115.6 mmol) in dioxane/$H_2O$ (200 mL/20 mL) was treated with $Pd(PPh_3)_4$ (3.00 g, 2.59 mmol) under a $N_2$ atmosphere. The mixture was stirred at 95° C. for 3 h and then concentrated in vacuo. The residue was dissolved in EtOAc (200 mL) and then water (200 mL) was added, and the layers were separated. The aqueous layer was extracted with EtOAc (100 mL×3), and the combined organic layers were washed with brine (100 mL×3) dried over anhydrous $Na_2SO_4$ and then concentrated in vacuo. The residue was purified by column chromatography on silica gel (PE:EtOAc=5:1~3:1) to give 1622-A (7.0 g, 64%) as a yellow solid Synthesis of 1622-B.

To a solution of 1622-A (2.00 g, 9.26 mmol) in pyridine (20.0 mL) was added phenyl carbonochloridate (4.33 g, 27.78 mmol) dropwise. After the addition was completed, the mixture was heated to 50° C. and stirred for 4 h. The mixture was then cooled to room temperature and concentrated in vacuo. The residue was purified by column chromatography on silica gel (DCM:EtOAc=8:1~2:1) to give 1622-B (3.80 g, 90%) as a yellow solid.

Synthesis of 1622-C.

A solution of of 6-chloro-2,3-dihydro-1H-pyrrolo[3,4-c] pyridine hydrochloride (5.00 g, 26.2 mmol) in DCM (200 mL) was cooled to 0° C. and treated with DIPEA (6.75 g, 52.4 mmol), added slowly, and the reaction mixture was stirred at 0° C. for 0.5 h. Then $(Boc)_2O$ was added slowly, and after the addition was complete the reaction was allowed to warm to room temperature and stirred for 1 h. After 1 h, the reaction had gone to completion as indicated by when LCMS, at which point the reaction mixture was diluted with water, and extracted with DCM, dried over $Na_2SO_4$, concentrated under reduced pressure and purified by flash column chromatography to obtain 1622-C (5.5 g, 83%) as white solid.

Synthesis of 1622-D.

A mixture of 1622-C (320 mg, 1.38 mmol), trimethylboroxine (522 mg, 4.14 mmol) and $K_2CO_3$ (952 mg, 6.9 mmol) in dioxane (15 mL) was treated with $Pd(dppf)_2Cl_2$ (57 mg, 0.07 mmol) under a $N_2$ atmosphere. The mixture was stirred at 95° C. for 24 h and then concentrated in vacuo. The residue was dissolved with EtOAc (20 mL) and the solution was washed with brine (20 mL×3). The organic layer was dried over anhydrous $Na_2SO_4$ and then concentrated in vacuo. The residue was purified by column chromatography on silica gel (PE:EtOAc=5:1~2:1) to give 1622-D (160 mg, 50%) as a white solid.

Synthesis of 1622-E.

A solution of 1622-D (160 mg, 0.68 mmol) in DCM (5 mL) was treated with TFA (2 mL) and stirred at room temperature for 1 h, at which point LCMS indicated that the reaction was finished. The solvent was then removed in vacuo to give 1622-E as a crude product which was used directly in the next step.

Synthesis of 1622-F.

A mixture of 1622-B (190 mg, 0.42 mmol) and 1622-E (crude product from last step) in DMSO (5 mL) was stirred at room temperature for 10 min, then $Na_2CO_3$ (222 mg, 2.1 mmol) was added and the reaction mixture was stirred at room temperature for 2 h. After the reaction was completed as indicated by LCMS, the mixture was diluted with water (30 mL) and extracted with EtOAc (10 mL×3). The combined organic layers were washed with brine (10 mL×3), dried over anhydrous $Na_2SO_4$ and then concentrated in vacuo. The residue was purified by column chromatography on silica gel (DCM:MeOH=100:1~50:1) 1622-F (100 mg, 63%) as a yellow solid Synthesis of Compound 12.

A mixture of 1622-F (100 mg, 0.32 mmol) and Pd/C (100 mg) in MeOH (10 mL) was stirred at room temperature for 30 min under a $H_2$ atmosphere (1 atm). The Pd/C was then removed by filtration through Celite, the filtrate was concentrated and the residue was purified by Prep-TLC (DCM:MeOH=10:1) to give Compound 12 (52 mg, 56%) as a white solid.

Example 13—Intentionally Omitted

Example 14

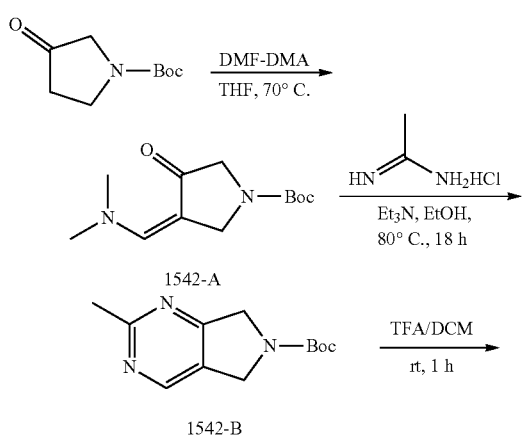

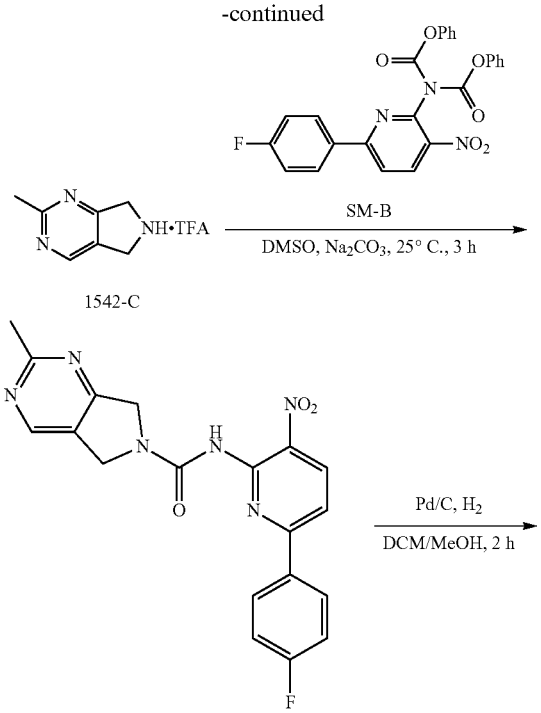

Synthesis of 1542-C.

To a solution of 1542-B (16.0 g, 68.0 mmol) in DCM (100 mL) cooled to 0° C. was added TFA (100 mL) dropwise. The reaction mixture was allowed to warm to room temperature, and then stirred at room temperature for 1 h. The solvent was removed in vacuo to give 1542-C as a crude product which was used directly in the next step. MS 136.0 [M+H]+.

Synthesis of 1542-D.

To a solution of SM-B (16.0 g, 33.8 mmol) and 1542-C (68.0 mmol, crude product from last step) in DMSO (160 mL) was added Na$_2$CO$_3$ (35.0 mg, 338 mmol). The resulting mixture was stirred at room temperature for 3 h. The mixture was then diluted with water (500 mL) and the precipitate was collected by filtration. The filter cake was recrystallized from DCM (200 mL) to provide 1542-D (9.4 g, 70%) as a brown solid. MS 395.4 [M+H]+.

Synthesis of Compound 14.

To a solution of 1542-D (9.4 g, 23.8 mmol) and Pd/C (1.88 g) in DCM/MeOH (200 mL/200 mL) was stirred at room temperature for 2 h under an atmosphere of H$_2$ (1 atm). The Pd/C was then removed by filtration through Celite, the filtrate was concentrated, and the residue was purified by column chromatography on silica gel (MeOH:EtOAc=0:1~10:1) to give Compound 14 (3.8 g, 44%) as a gray solid. MS 365.4 [M+H]+.

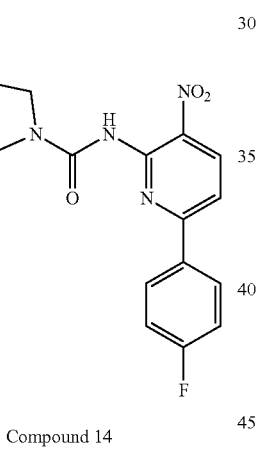

Compound 14

Synthesis of 1542-A.

A solution of tert-butyl 3-oxopyrrolidine-1-carboxylate (30.0 g, 162.0 mmol) and DMF-DMA (58.0 g, 486.5 mmol) in THF (300 mL) was stirred at 70° C. for 12 h. The reaction mixture was then concentrated to give 1542-A as a crude product which was used directly in the next step. MS 241.2 [M+H]+.

Synthesis of 1542-B.

A mixture of 1542-A (162.0 mmol, crude product from last step), acetimidamide hydrochloride (61.0 g, 648.0 mmol) and Et$_3$N (65.0 g, 648.0 mmol) in EtOH (450 mL) was stirred at 80° C. for 16 h. The mixture was then cooled to room temperature and diluted with water (500 mL), then extracted with EtOAc (400 mL×3). The combined organic layers were washed with brine (100 mL×3), dried over anhydrous Na$_2$SO$_4$ and then concentrated in vacuo. The residue was purified by column chromatography on silica gel (PE:EtOAc=10:1~1:1) to give 1542-B (16.0 g, 42%) as a gray solid. MS 236.1 [M+H]+.

Example 15

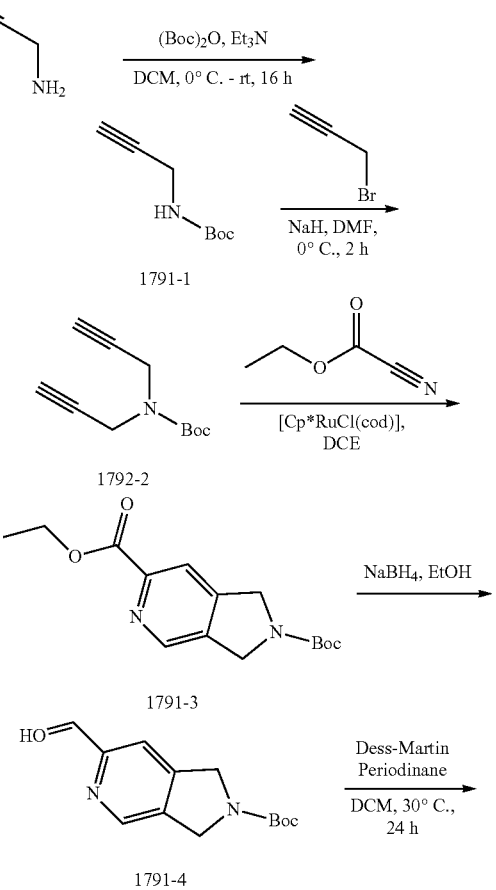

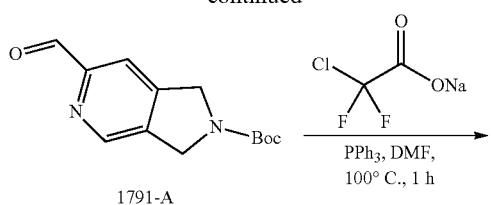

1791-A

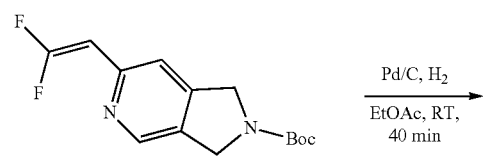

1791-B

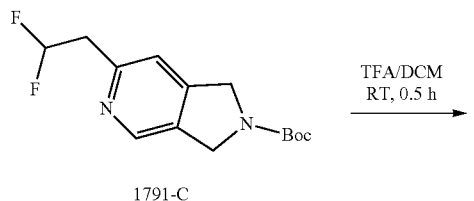

1791-C

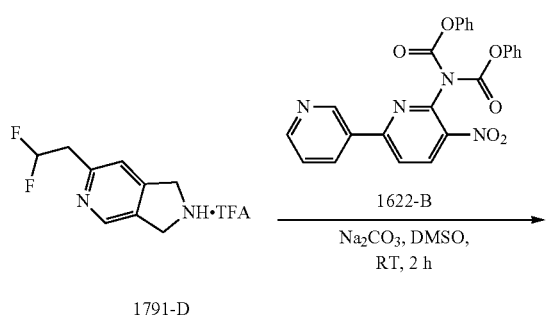

1791-D

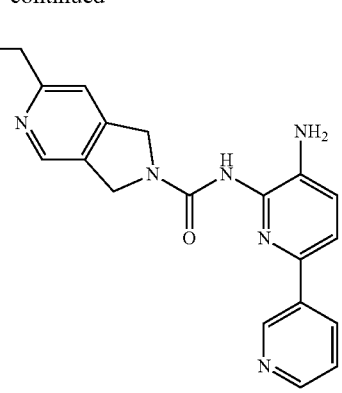

Compound 15

Synthesis of 1791-1.

A solution of prop-2-yn-1-amine (5.0 g, 90.9 mmol) and Et$_3$N (18.4 g, 181.8 mmol) in DCM (100 mL) was cooled to 0° C., and then treated with (Boc)$_2$O (23.8 g, 109.1 mmol). The resulting reaction mixture was allowed to warm to room temperature, and was stirred at room temperature for 16 h. The mixture was then diluted with DCM (200 mL), washed with brine (100 mL×3), and the organic layer was dried over Na$_2$SO$_4$ and then concentrated in vacuo. The residue was purified by column chromatography on silica gel (PE:EtOAc=100:1~10:1) to give 1791-1 (10 g, 71%) as a colorless oil. MS 178.3 [M+23]$^+$, 100.3 [M−56]$^+$.

Synthesis of 1791-2.

A solution of 1791-1 (10 g, 64.5 mmol) in DMF (200 mL) was cooled to 0° C. and treated with NaH (60% in mineral oil) (2.84 g, 71 mmol), added slowly. The resulting reaction mixture was allowed to warm to room temperature, and was stirred at room temperature for 1 h. Then 3-bromoprop-1-yne (9.2 g, 77.4 mmol) was added to the reaction mixture, and stirring was continued at room temperature for 2 h. The mixture was then quenched with water (500 mL), and extracted with t-BuOMe (250 mL×3). The combined organic layers were washed with brine (200 mL×3), dried over anhydrous Na$_2$SO$_4$ and then concentrated in vacuo. The residue was purified by column chromatography on silica gel (PE:EtOAc=100:1~10:1) to give 1791-2 (12 g, 96%) as a yellow oil. MS 138.1 [M−56]$^+$.

Synthesis of 1791-3.

To a solution of ethyl carbonocyanidate (4.10 g, 41.4 mmol) and [Cp*RuCl(cod)] (394 mg, 1.0 mmol) in DCE (40 mL) was added a solution of 1791-2 (4.0 g, 20.7 mmol) in DCE (80 mL) dropwise over 30 min under a N$_2$ atmosphere. The resulting mixture was stirred at 40° C. for 16 h. The solvent was then removed in vacuo, and the residue was purified by column chromatography on silica gel (PE:EtOAc=10:1~2:1) to give 1791-3 (2.1 g, 35%) as a tan solid. MS 293.3 [M+H]$^+$.

Synthesis of 1791-4.

To a solution of 1791-3 (2.0 g, 6.8 mmol) in anhydrous ethanol was added NaBH$_4$ (1.56 g, 41.1 mmol) at room temperature. The reaction mixture was stirred at room temperature for 16 h, whereupon the mixture was quenched with water (50 mL), and extracted with DCM (30 mL×3). The combined organic layers were washed with brine (30 mL×3), dried over anhydrous Na$_2$SO$_4$ and then concentrated in vacuo. The residue was purified by column chromatography on silica gel (PE:EtOAc=50:1~5:1) to give 1791-4 (1.2 g, 70%) as a white solid. MS 251.1 [M+H]+.

Synthesis of 1791-A.

A mixture of 1791-4 (500 mg, 2.0 mmol) and Dess-Martin Periodinane (1.7 g, 4.0 mmol) in DCM (20 mL) was stirred at 30° C. for 24 h. The precipitate was then removed by filtration through Celite, and the filtrate was concentrated under reduced pressure. The residue was purified by column chromatography on silica gel (DCM:MeOH=100:1~50:1) to give 1791-A (450 mg, 91%) as a white solid. MS 149.3 [M–100]+.

Synthesis of 1791-B.

A mixture of sodium 2-chloro-2,2-difluoroacetate (228 mg, 1.8 mmol) and PPh3 (472 mg, 1.8 mmol) in DMF (10 mL) was stirred at room temperature for 2 h. Then 1791-A (300 mg, 1.2 mmol) was added, and the resulting mixture was heated to 100° C. and stirred at 100° C. for 1 h. The mixture was then cooled to room temperature and diluted with water (30 mL), then extracted with EtOAc (20 mL×3). The combined organic layers were washed with brine (20 mL×3), dried over anhydrous Na2SO4 and then concentrated in vacuo. The residue was purified by column chromatography on silica gel (DCM:MeOH=100:1~30:1) to give 1791-B (220 mg, 60%) as a white solid. MS 283.3 [M+H]+.

Synthesis of 1791-C.

A mixture of 1791-B (200 mg, 0.71 mmol) and Pd/C (120 mg) in EtOAc (15 mL) was stirred under a H2 atmosphere (1 atm) at room temperature for 40 min. The Pd/C was then removed by filtration through Celite, and the filtrate was concentrated to give 1791-C (170 mg, 84.4%) as a brown solid. MS 285.2 [M+H]+.

Synthesis of 1791-D.

To a solution of 1791-C (170 mg, 0.60 mmol) in DCM (6 mL) was added TFA (1.5 mL). Then the solution was stirred at room temperature for 0.5 h. The solvent was removed in vacuo to give 1791-D as a crude product which was taken on to the next step without purification. MS 185.2 [M+H]+.

Synthesis of 1791-E.

A solution of 1791-D (0.60 mmol, crude product from last step) and 1622-B (143 mg, 0.31 mmol) in DMSO (5 mL) was treated with Na2CO3 (394 mg, 3.72 mmol), and the mixture was stirred at room temperature for 2 h. The reaction mixture was then diluted with water (20 mL), extracted with EtOAc (10 mL×4), the combined organic layers were washed with brine (10 mL×3), dried over anhydrous Na2SO4 and then concentrated in vacuo. The residue was purified by column chromatography on silica gel (DCM:MeOH=50:1~30:1) to give 1791-E (80 mg, 60%) as a yellow solid. MS 427.1 [M+H]+.

Synthesis of Compound 15.

A mixture of 1791-E (80 mg, 0.19 mmol) and Pd/C (100 mg) in MeOH/EtOAc (8 mL/8 mL) was stirred under a H2 atmosphere (1 atm) at room temperature for 40 min. The Pd/C was then removed by filtration through Celite, the filtrate was concentrated and the residue was purified by Prep-HPLC to give Compound 15 (33 mg, 44%) as white solid. MS 397.2 [M+H]+.

Example 16

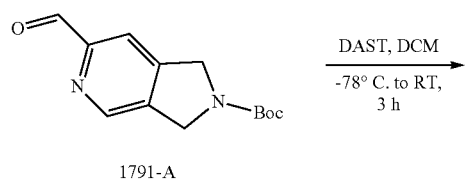

1791-A

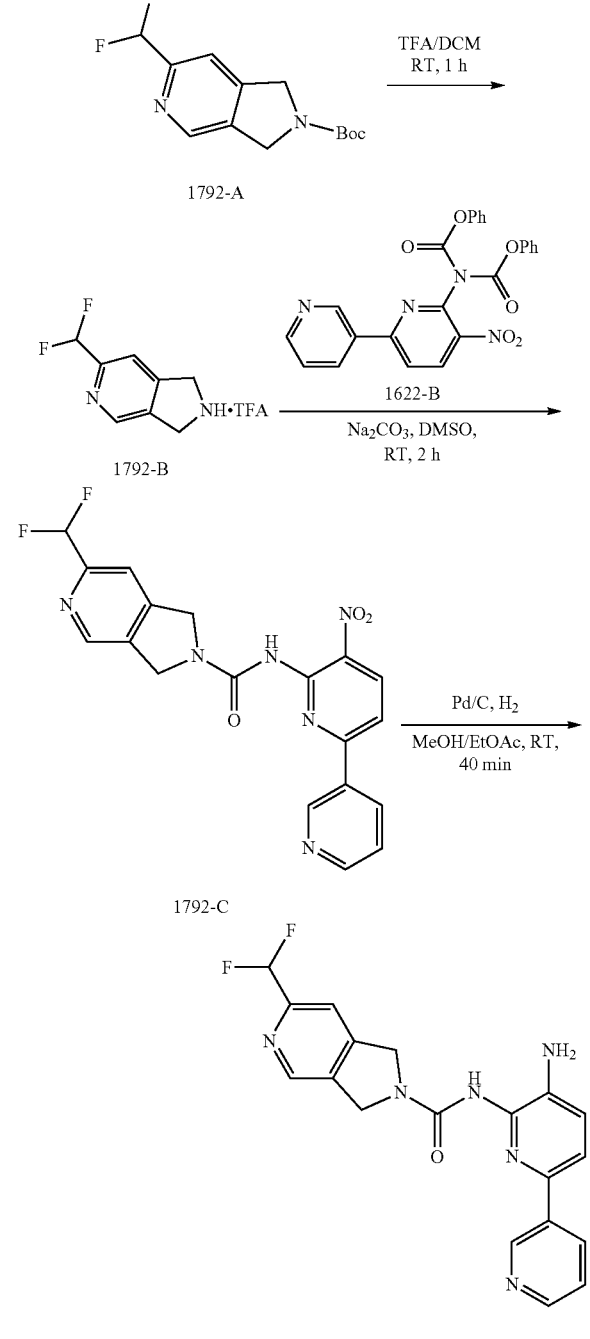

Synthesis of 1792-A.

To a solution of 1791-A (125 mg, 0.5 mmol) in DCM (5 mL) was added DAST (201 mg, 1.25 mmol) dropwise at −78° C. The reaction mixture was then warmed to room temperature and stirred for 3 h. The mixture was then diluted with DCM (15 mL), washed with brine (10 mL×3), dried over anhydrous Na2SO4 and then concentrated in vacuo. The residue was purified by column chromatography on silica gel (DCM:MeOH=100:1~30:1) to give 1792-A (110 mg, 81%) as a white solid. MS 271.2 [M+H]+.

Synthesis of 1792-B.

A solution of 1792-A (110 mg, 0.41 mmol) in DCM (4 mL) was cooled to 0° C. and then TFA (2 mL) was added dropwise. The reaction mixture was allowed to warm to RT and stirred at room temperature 1 h. The solvent was removed in vacuo to give 1792-B as a crude product which was taken on to the next step without purification. MS 171.4 [M+H]⁺.

Synthesis of 1792-C.

To a mixture of 1792-B (0.41 mmol, crude product from last step) and 1622-B (186 mg, 0.41 mmol) in DMSO (5 mL) was added Na₂CO₃ (217 mg, 2.05 mmol), and the reaction mixture was stirred at 25° C. for 2 h. The mixture was then diluted with water (20 mL), extracted with EtOAc (10 mL×3), and the combined organic layers were washed with brine (10 mL×3), dried over anhydrous Na₂SO₄ and then concentrated in vacuo. The residue was purified by column chromatography on silica gel (DCM:MeOH=100:1~30:1) to give 1792-C (110 mg, 67%) as a yellow solid. MS 413.2 [M+H]⁺.

Synthesis of Compound 16.

A mixture of 1792-C (110 mg, 0.27 mmol) and Pd/C (110 mg) in MeOH/EtOAc (5 mL/5 mL) was stirred under a H₂ atmosphere (1 atm) at room temperature for 1 h. The Pd/C was then removed by filtration through Celite, the filtrate was concentrated and the residue was purified by Prep-TLC (DCM:MeOH=15:1) to give Compound 16 (50 mg, 48%) as a yellow solid. MS 383.2 [M+H]⁺.

Example 17

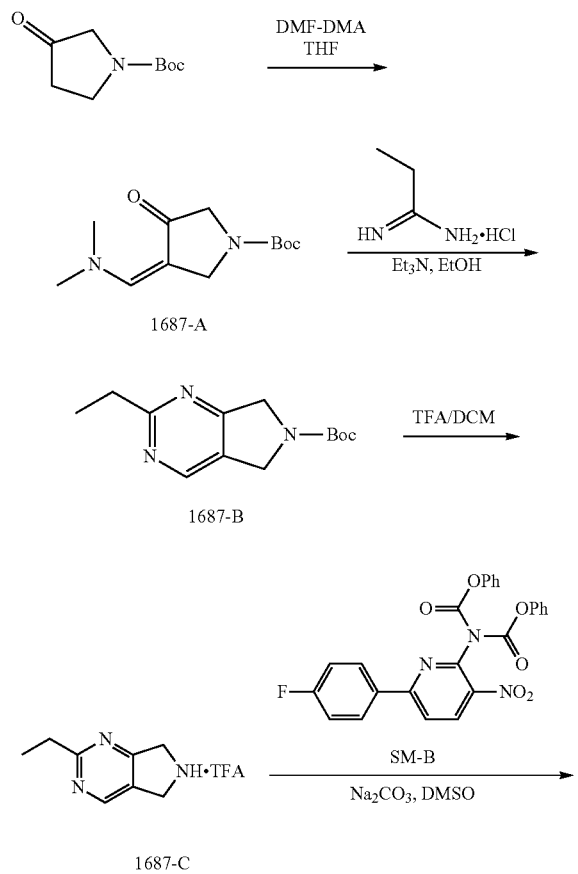

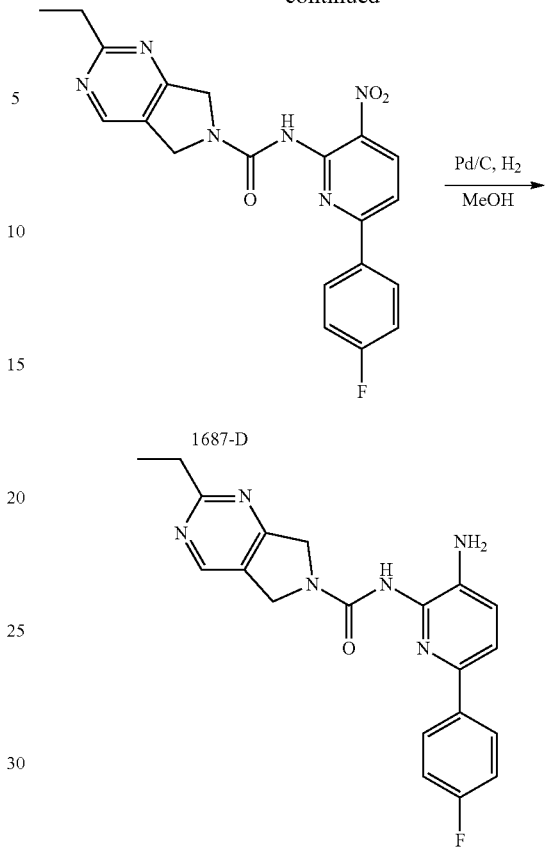

Synthesis of 1687-A.

A solution of tert-butyl 3-oxopyrrolidine-1-carboxylate (4.0 g, 21.6 mmol) and DMF-DMA (7.6 g, 64.8 mmol in THF (40 mL) was stirred at 70° C. for 16 h. The solution was concentrated in vacuo to give 1687-A as a crude product which was used directly in the next step. MS 241.3 [M+H]⁺.

Synthesis of 1687-B.

To a solution of 1687-A (8.2 mmol, crude product from last step) in EtOH (10 mL) was added Et₃N (4.1 g, 41.0 mmol) and propionimidamide hydrochloride (3.55 g, 32.8 mmol). The resulting solution was stirred at 80° C. for 24 h. After the mixture was cooled to room temperature, the mixture was diluted with water (50 mL) and extracted with DCM (30 mL×3). The combined organic layers were washed with brine (30 mL×3), dried over anhydrous Na₂SO₄ and then concentrated in vacuo. The residue was purified by column chromatography on silica gel (PE:DCM=10:1~1:2) to give 1687-B (1.0 g, 49%) as a brown solid. MS 250.3 [M+H]⁺.

Synthesis of 1687-C.

To a solution of 1687-B (1.0 g, 4.02 mmol) in DCM (10 mL) was added TFA (5 mL) in dropwise fashion. The reaction mixture was stirred at room temperature for 1 h, then was concentrated in vacuo to give 1687-C as a crude product which was used directly in the next step. MS 150.3 [M+H]⁺.

Synthesis of 1687-D.

A mixture of SM-B (300 mg, 0.63 mmol) and 1687-C (0.82 mmol, crude product from last step) in DMSO (8 mL) was treated with Na₂CO₃ (537 mg, 5.07 mmol), and the reaction mixture was stirred at room temperature for 2 h. The mixture was then diluted with water (20 mL), and extracted with EtOAc (20 mL×3). The combined organic layers were washed with brine (20 mL×3), dried over anhydrous $Na_2SO_4$ and then concentrated in vacuo. The residue was purified by column chromatography on silica gel (DCM:MeOH=100:1~50:1) to give 1687-D (150 mg, 58%) as a yellow solid. MS 409.4 $[M+H]^+$.

Synthesis of Compound 17.

A mixture of 1687-D (100 mg, 0.25 mmol) and Pd/C (100 mg) in MeOH (10 mL) was stirred under a $H_2$ atmosphere (1 atm) at room temperature for 1 h. The Pd/C was then removed by filtration through Celite, the filtrate was concentrated and the residue was purified by Prep-TLC (DCM: MeOH=10:1) to give Compound 17 (25 mg, 27%) as a yellow solid (MS 379.4 $[M+H^{1+}]$).

TABLE 1

Spectrometric Data for Compounds

| No. | Structure | MS Calc | MS found | $^1$H NMR Data (400 MHz, DMSO-$d_6$) |
|---|---|---|---|---|
| 1 | 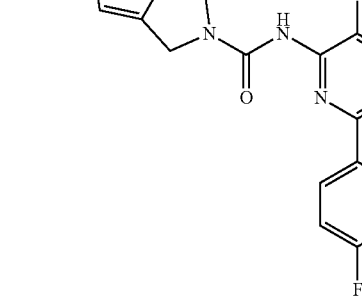 | 394 | 395 | δ 8.49 (s, 1H), 7.98 (dd, J = 8.8, 5.6 Hz, 2H), 7.75 (s, 1H), 7.57 (d, J = 8.2 Hz, 1H), 7.23 (t, J = 8.8 Hz, 2H), 7.18 (d, J = 8.0 Hz, 1H), 5.62-5.55 (m, 1H), 5.17 (s, 2H), 4.93-4.90 (m, 4H), 4.56 (d, J = 21.6 Hz, 4H). |
| 2 | 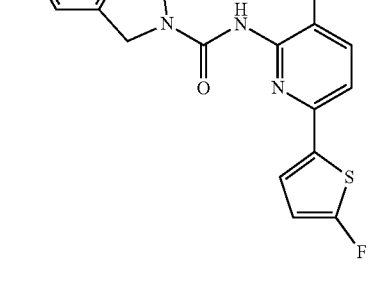 | 370 | 371 | δ 8.70 (s, 1H), 8.58 (s, 1H), 7.51(d, J = 8.0 Hz, 1H), 7.17 (t, J = 4.0 Hz, 1H), 7.12 (d, J = 8.4 Hz, 1H), 6.68-6.66 (m, 1H), 5.20 (s, 2H), 4.76 (d, J = 13.2 Hz, 4H), 2.64 (s, 3H). |
| 3 | 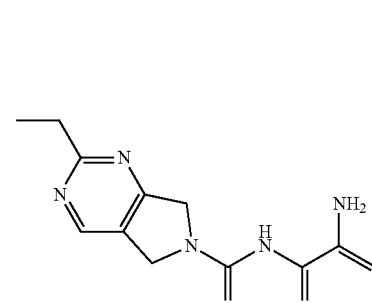 | 366 | 367 | δ 8.73 (s, 1H), 8.59 (s, 1H), 7.58-7.46 (m, 2H), 7.41 (dd, J = 5.0, 1.0 Hz, 1H), 7.12 (d, J = 8.2 Hz, 1H), 7.06 (dd, J = 5.0, 3.7 Hz, 1H), 5.18 (s, 2H), 4.77 (d, J = 8.2 Hz, 4H), 2.92 (q, J = 7.6 Hz, 2H), 1.29 (t, J = 7.6 Hz, 3H). |

TABLE 1-continued
Spectrometric Data for Compounds
| No. | Structure | MS Calc | MS found | ¹H NMR Data (400 MHz, DMSO-d₆) |
|---|---|---|---|---|
| 4 | 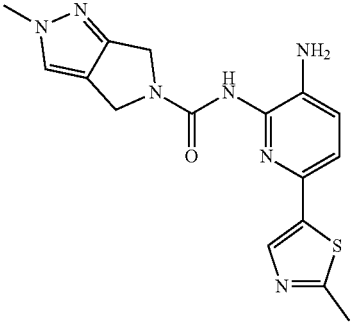 | 355 | 356 | δ 8.43 (s, 1H), 7.99 (s, 1H), 7.55-7.51 (m, 2H), 7.13 (d, J = 8.2 Hz, 1H), 5.24 (s, 2H), 4.49 (s, 4H), 3.85 (s, 3H), 2.62 (s, 3H). |
| 5 | 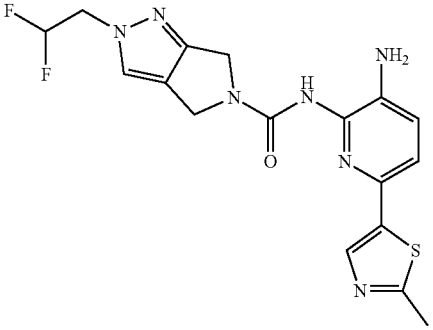 [SMILES: Cc1ncc(-c2ccc(N)c(NC(=O)N3Cc4cn(CC(F)F)nc4C3)n2)s1] | 405 | 406 | δ 8.47 (s, 1H), 7.99 (s, 1H), 7.65 (s, 1H), 7.52 (d, J = 8.0 Hz, 1H), 7.12 (d, J = 8.0 Hz, 1H), 6.36 (tt, J = 55.2, 4.0 Hz, 1H), 5.24 (s, 2H), 4.67-4.59 (m, 6H), 2.62 (s, 3H). |
| 6 | 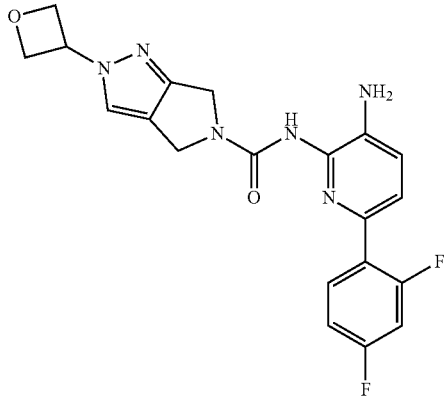 [SMILES: Nc1ccc(-c2ccc(F)cc2F)nc1NC(=O)N1Cc2cn(C3COC3)nc2C1] | 412 | 413 | δ 8.51 (s, 1H), 7.94 (dd, J = 16.0, 9.0 Hz, 1H), 7.74 (s, 1H), 7.41 (dd, J = 8.0, 1.9 Hz, 1H), 7.32-7.27 (m, 1H), 7.19-7.14 (m, 2H), 5.72-5.55 (m, 1H), 5.26 (s, 2H), 4.94-4.88 (m, 4H), 4.55 (d, J = 21.2 Hz, 4H). |
| 7 | 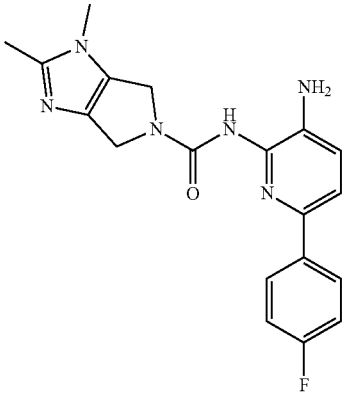 [SMILES: Cc1nc2c(n1C)CN(C(=O)Nc1nc(-c3ccc(F)cc3)ccc1N)C2] | 366 | 367 | δ 8.40 (s, 1H), 7.98 (dd, J = 8.4, 5.6 Hz, 2H), 7.57 (d, J = 8.0 Hz, 1H), 7.22 (t, J = 8.2 Hz, 2H), 7.17 (d, J = 8.4 Hz, 1H), 5.14 (s, 2H), 4.53-4.42 (m, 4H), 3.53 (s, 3H), 2.30 (s, 3H). |

TABLE 1-continued

Spectrometric Data for Compounds

| No. | Structure | MS Calc | MS found | ¹H NMR Data (400 MHz, DMSO-d$_6$) |
|---|---|---|---|---|
| 8 | 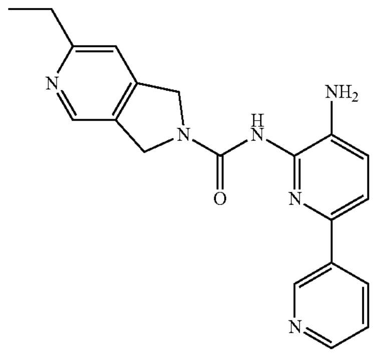 [SMILES: CCc1cc2c(cn1)CN(C(=O)Nc1nc(-c3cccnc3)ccc1N)C2] | 360 | 361 | δ 9.14 (d, J = 1.6 Hz, 1H), 8.59 (s, 1H), 8.49-8.47 (m, 2H), 8.27 (dt, J = 8.4, 2.0 Hz, 1H), 7.69-7.67 (d, J = 8.4 Hz, 1H), 7.44-7.41 (m, 1H), 7.30 (s, 1H), 7.19 (d, J = 8.4 Hz, 1H), 5.31 (s, 2H), 4.80 (s, 4H), 2.77 (q, J = 7.6 Hz, 2H), 1.24 (t, J = 7.6 Hz, 3H). |
| 9 | 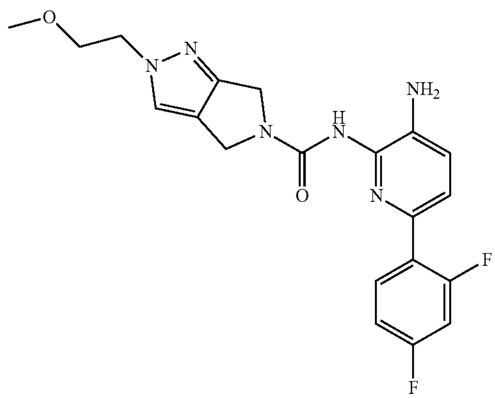 [SMILES: COCCn1cc2c(n1)CN(C(=O)Nc1nc(-c3ccc(F)cc3F)ccc1N)C2] | 414 | 415 | δ 8.48 (s, 1H), 7.98-7.91 (m, 1H), 7.57 (s, 1H), 7.41 (dd, J = 8.0, 2.0 Hz, 1H), 7.32-7.26 (m, 1H), 7.18-7.13 (m, 2H), 5.25 (s, 2H), 4.52 (s, 4H), 4.27-4.24 (t, J = 5.4 Hz, 2H), 3.69-3.66 (t, J = 5.2 Hz, 2H), 3.24 (s, 3H). |
| 11 | 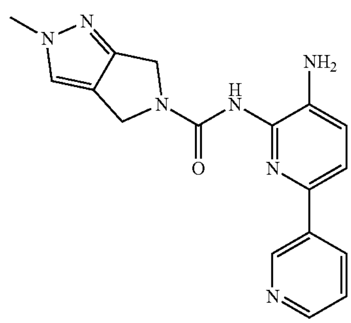 [SMILES: Cn1cc2c(n1)CN(C(=O)Nc1nc(-c3cccnc3)ccc1N)C2] | 355 | 356 | δ 9.15 (s, 1H), 8.48 (s, 2H), 8.29-8.26 (m, 1H), 7.68-7.66 (d, J = 8 Hz, 1H), 7.56 (s, 1H), 7.44-7.40 (m, 1H), 7.21-7.19 (d, J = 8 Hz, 1H), 5.28 (s, 2H), 4.52 (s, 4H), 3.85 (s, 3H) |
| 12 | 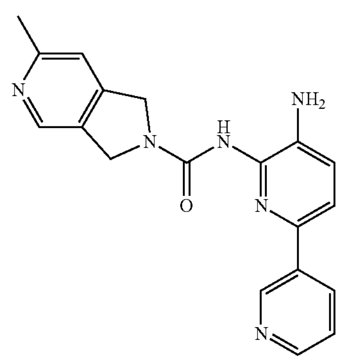 [SMILES: Cc1cc2c(cn1)CN(C(=O)Nc1nc(-c3cccnc3)ccc1N)C2] | 346 | 347 | ¹H NMR (400 MHz, CDCl$_3$) δ 9.11 (d, J = 1.8 Hz, 1H), 8.59-8.55 (m, 1H), 8.51 (s, 1H), 8.27-8.08 (m, 1H), 7.47 (d, J = 8.1 Hz, 1H), 7.34 (dd, J = 7.5, 4.8 Hz, 1H), 7.20 (d, J = 8.1 Hz, 1H), 7.16 (s, 1H), 6.95 (s, 1H), 4.90 (m, 4H), 4.67 (s, 2H), 2.61 (s, 3H). |

TABLE 1-continued

Spectrometric Data for Compounds

| No. | Structure | MS Calc | MS found | ¹H NMR Data (400 MHz, DMSO-$d_6$) |
|---|---|---|---|---|
| 14 | 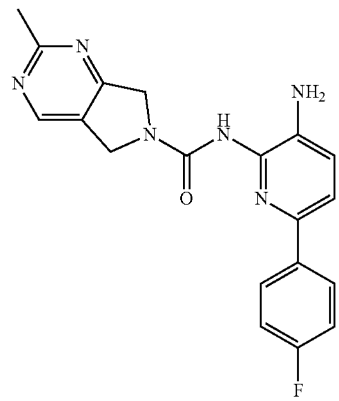 [SMILES: Cc1ncc2c(n1)CN(C(=O)Nc1nc(-c3ccc(F)cc3)ccc1N)C2] | 364 | 365 | δ 8.71 (s, 1H), 8.63 (s, 1H), 7.99-7.96 (q, J = 5.6 Hz, 2H), 7.59-7.57 (d, J = 8.0 Hz, 1H), 7.25-7.16 (m, 3H), 5.20 (s, 2H), 4.79-4.77 (d, J = 8.8 Hz, 4H), 2.64 (s, 3H). |
| 15 | 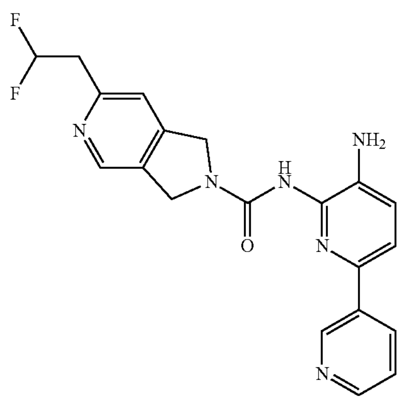 [SMILES: Nc1ccc(-c2cccnc2)nc1NC(=O)N1Cc2cnc(CC(F)F)cc2C1] | 396 | 397 | δ 9.14 (m, 1H), 8.61-8.57 (m, 2H), 8.48 (m, 1H), 8.29-8.26 (m, 1H), 7.69-7.67 (m, 1H), 7.44-7.40 (m, 2H), 7.20-7.18 (m, 1H), 6.44 (tt, J = 56.0, 4.8 Hz, 1H), 5.31 (s, 2H), 4.83 (s, 4H), 3.45-3.36 (m, 2H). |
| 16 | 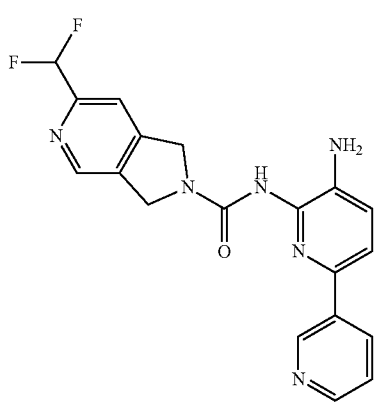 [SMILES: Nc1ccc(-c2cccnc2)nc1NC(=O)N1Cc2cnc(C(F)F)cc2C1] | 382 | 383 | δ 9.14 (d, J = 2.0 Hz, 1H), 8.71 (s, 1H), 8.65 (s, 1H), 8.48 (dd, J = 4.4, 1.2 Hz, 1H), 8.29-8.26 (m, 1H), 7.78 (s, 1H), 7.68 (d, J = 8.4 Hz, 1H), 7.44-7.41 (m, 1H), 7.19 (d, J = 8.4 Hz, 1H), 7.00 (t, J = 54.8 Hz, 1H), 5.32 (s, 2H), 4.90 (s, 4H). |

TABLE 1-continued

Spectrometric Data for Compounds

| No. | Structure | MS Calc | MS found | $^1$H NMR Data (400 MHz, DMSO-$d_6$) |
|---|---|---|---|---|
| 17 | 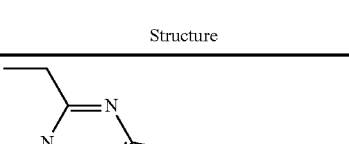 | 378 | 379 | δ 8.74 (s, 1H), 8.61 (s, 1H), 8.00-7.96 (m, 2H), 7.58 (d, J = 8.2 Hz, 1H), 7.25-7.16 (m, 3H), 5.18 (s, 2H), 4.78 (d, J = 9.1 Hz, 4H), 2.92 (q, J = 7.5 Hz, 2H), 1.29 (t, J = 7.6 Hz, 3H). |

HDAC2 and HDAC1 Enzymatic Assay

The following describes an assay protocol for measuring the deacetylation of a peptide substrate by the enzymes HDAC2 or HDAC1. Enzyme, substrate, and cofactors are combined in a well of a microtiter plate and incubated for 3 hours at 25° C. At the end of the incubation, the reaction is quenched by the addition of an SDS-containing buffer. Substrate and product are separated and quantified electrophoretically using the microfluidic-based LabChip 3000 Drug Discovery System from Caliper Life Sciences. The peptide substrate used in this assay is FAM-TSRHK(AC)KL-CONH2 (FAM is carboxyfluorescein). Peptide should be >98% purity by Capillary Electrophoresis.

1. To a well of a 384-well plate, add 5 μL of 2× enzyme buffer. Using Labcyte Echo 550, add 100 nl compound. Enzyme and compound may be pre-incubated at this time if desired.
2. Add 5 μL of 2× substrate buffer.
3. Incubate plate at 25° C. for 17 hours.
4. Terminate reaction by adding 40 μL of 1.55× stop buffer.
5. Create job on a Caliper LabChip® 3000 Drug Discovery System.
6. Load the plate and start electrophoresis using blue laser (480 nm) for excitation and green CCD (520 nm) for detection (CCD2).

Reaction time=17 hours; Reaction temperature=25° C.

Final Assay Reaction Mixture 100 mM HEPES, pH 7.5 0.1% BSA 0.01% Triton X-100 25 mM KCl 1% DMSO (from compound) 1 μM FAM-TSRHK(AC)KL-CONH2 5 nM HDAC Enzyme (specific activity may vary from lot-to-lot, and enzyme concentration may need to be adjusted to yield~10-20% conversion of substrate to product).

Substrate and product peptides present in each sample are separated electrophoretically using the LabChip 3000 capillary electrophoresis instrument. As substrate and product peptides are separated, two peaks of fluorescence are observed. Change in the relative fluorescence intensity of the substrate and product peaks is the parameter measured, reflecting enzyme activity. Capillary electrophoregramms (RDA acquisition files) are analyzed using HTS Well Analyzer software (Caliper Life Sciences). The kinase activity in each sample is determined as the product to sum ratio (PSR): P/(S+P), where P is the peak height of the product peptide and S is the peak height of the substrate peptide. For each compound, enzyme activity is measured at various concentrations (12 concentrations of compound spaced by 3× dilution intervals). Negative control samples (0%-inhibition in the absence of inhibitor) and positive control samples (100%-inhibition, in the presence of 20 mM EDTA) are assembled in replicates of four and are used to calculate %-inhibition values for each compound at each concentration. Percent inhibition ($P_{inh}$) is determined using following equation: $P_{inh}=(PSR_{0\%}-PSR_{inh})/(PSR_{0\%}-PSR_{100\%})*100$, where $PSR_{inh}$ is the product sum ratio in the presence of inhibitor, $PSR_{0\%}$ is the average product sum ration in the absence of inhibitor and $PSR_{100}\%$ is the average product sum ratio in 100%-inhibition control samples.

The IC50 values of inhibitors are determined by fitting the inhibition curves ($P_{inh}$ versus inhibitor concentration) by 4 parameter sigmoidal dose-response model using XLfit 4 software (IBDS).

The results of this assay for certain compounds are reported in Table 2, below. In the table, "A" indicates a $K_d$ value of between 0.1 μM and 0.5 μM and "B" a $K_d$ value of greater than 0.5 μM and less than or equal to 5.0 μM.

TABLE 2

| Compound No. | HDAC2 IC50, (uM) | HDAC1 IC50, (uM) |
|---|---|---|
| 1 | C | B |
| 2 | C | B |
| 3 | C | B |
| 4 | C | C |
| 5 | C | B |
| 6 | B | B |
| 7 | C | C |
| 8 | B | B |
| 9 | C | B |
| 11 | C | C |
| 12 | C | C |
| 14 | C | B |
| 15 | C | C |

TABLE 2-continued

| Compound No. | HDAC2 IC50, (uM) | HDAC1 IC50, (uM) |
| --- | --- | --- |
| 16 | C | C |
| 17 | B | B |

HDAC2 Enzymatic Inhibition Assay in SY5Y Cell Lysate

Cell Culture and Inhibitor Treatments

SH-SY5Y cells (Sigma) were cultured in Eagle's Modified Essential Medium supplemented with 10% fetal bovine serum and pen/strep. Twenty-four hours prior to compound dosing 20 uL of cells were plated in white 384 well plates at a density of 1,500 cells/well. Compounds were serially diluted in neat DMSO and then diluted 1:100 v/v into media without FBS and mixed. Media was removed from the plated cells and the diluted compounds in serum free media (1% v/v final DMSO) were added and incubated at 37.0 for five hours. Ten uL of HDAC-Glo 2 reagent with 0.1% Triton X-100 was then added, the plate was mixed and allowed to develop at room temperature for 100 minutes. Plates were then read with a Spectramax LMax luminometer employing a 0.4 s integration time. Dose response curves were constructed with normalized data where CI-994 at 100 uM was defined as 100% inhibition and DMSO alone as 0% inhibition.

The results of this assay for certain compounds are reported in Table 3, below. In the table, "A" indicates an $IC_{50}$ value of between 0.1 µM and 1 µM; "B" indicates an a $IC_{50}$ value of between 1.0 µM and 1.5 µM; and "C" indicates an a $IC_{50}$ value of greater than 1.5 µm.

TABLE 3

| Compound No. | HDAC2 IC50, SY5Y Cell Lysate (uM) |
| --- | --- |
| 1 | A |
| 2 | B |
| 3 | A |
| 4 | A |
| 5 | A |
| 6 | A |
| 7 | A |
| 8 | A |
| 9 | A |
| 11 | A |
| 12 | A |
| 14 | A |
| 15 | A |
| 16 | C |
| 17 | B |

Erythroid and Myeloid CFU Assay

Compounds were tested to evaluate the potential effects on human erythroid and myeloid progenitors using colony forming cell assays. Clonogenic progenitors of human erythroid (CFU-E, BFU-E), granulocyte-monocyte (CFU-GM) and multipotential (CFU-GEMM) lineages were assessed in a semi-solid methylcellulose-based media formulation containing rhIL-3 (10 ng/mL), rhGM-SCF (10 ng/mL), rhSCF (50 ng/mL) and Epo (3 U/mL).

Cells

Normal human bone marrow light density cells derived from normal bone marrow (NorCal Biologics, California), were stored in the gaseous phase of liquid nitrogen (−152° C.) until required for the assay. On the day of the experiment, the cells were thawed rapidly, the contents of each vial was diluted in 10 mL of Iscove's modified Dulbecco's medium containing 10% fetal bovine serum (IMDM+10% FBS) and washed by centrifugation (approximately 1200 r.p.m. for 10 minutes, room temperature). The supernatant was discarded and the cell pellets resuspended in a known volume of IMDM+10% FBS. A cell count (3% glacial acetic acid) and viability assessment (trypan blue exclusion test) was performed for the bone marrow sample.

Compounds

On the day of the experiment, the compounds were dissolved in DMSO to a stock concentration of 10 mM. Serial dilutions were prepared from the stock concentration to achieve concentrations of 2 and 0.4 mM. When added to the methylcellulose-based media at 1:1000 (v/v), the final test concentrations of 10, 2 and 0.4 µM were achieved. Additionally, 5-FU was evaluated at 1.0, 0.1 and 0.01 µg/mL.

Method Summary

Clonogenic progenitors of the human erythroid (CFU-E and BFU-E) and myeloid (CFU-GM) lineages were set up in the methylcellulose-based media formulations described above. All compounds were added to the medium to give the final desired concentrations (10, 2 and 0.4 µM). 5-Fluorouracil (Sigma Aldrich) was used as a positive control for progenitor proliferation (inhibition of colony growth) and was introduced to the human bone marrow cultures at 1.0, 0.1, and 0.01 µg/mL. Solvent control cultures (containing no compound but 0.1% DMSO) as well as standard controls (containing no compound and no DMSO) were also initiated.

Human myeloid and erythroid progenitor assays were initiated at $2.0 \times 10^4$ cells per culture. Following 14 days in culture, myeloid and erythroid colonies were assessed microscopically and scored by trained personnel. The colonies were divided into the following categories based on size and morphology: CFU-E, BFU-E, CFU-GM and CFU-GEMM.

Statistical Analyses of CFC Numbers

The mean±one standard deviation of three replicate cultures was calculated for progenitors of each category (CFU-E, BFU-E, etc.). Two-tailed t-tests were performed to assess if there was a difference in the number of colonies generated between solvent control and treated cultures. Due to the potential subjectivity of colony enumeration, a p value of less than 0.01 is deemed significant. To calculate the concentration of 50% inhibition of colony growth ($IC_{50}$) for each compound, a dose response curve was generated plotting the log of the compound concentration versus the percentage of control colony growth using XLfit software (IDBS). The concentration of 50% inhibition of colony growth ($IC_{50}$) was calculated based on the sigmoid curve fit using Dose-Response, One-Site Model formula: $y = A + [(B-A)/(1+((C/x)^D))]$, where A=the initial value (baseline response), B=maximum response, C=center (drug concentration that provokes a response halfway between A and B) and D=slope of the curve at midpoint. Further, plots and additional dose response curves were generated using GraphPad Prism 7.0.

Morphological Assessment of Colonies

Photographs were taken of representative hematopoietic progenitor-derived colonies from various lineages, illustrating colonies in the presence of the solvent control as well as colonies in the presence of the test compounds.

Erythroid (CFU-E and BFU-E), myeloid (CFU-GM) and multi-potential (CFU-GEMM) colony enumeration was performed by trained personnel. The distribution of colony types as well as general colony and cellular morphology was analyzed. For statistical analysis colony numbers in compound treated cultures were compared to the solvent control cultures. 5-FU was used as a positive control for toxicity in these assays and the inhibitory effects obtained for this compound were exactly as expected. The experiment was used to evaluate the potential effect of test compounds on human erythroid and myeloid progenitor proliferation in a methylcellulose-based medium. The $IC_{50}$ values were calculated from XLfit. Dose response curves for erythroid and myeloid toxicity generated by XLfit. Finally, nonlinear regression curve fitting and $IC_{50}s\pm95\%$ CI, were calculated by Prism 7.0.-GEMM. Results are shown in Table 4.

As shown from the data, certain structural modifications were found to have a profound effect on safety. For example, in certain instances, the replacement of a 4-fluorophenyl group (such as in Comparator 2 and Comparator 3) with more polar ring systems such as 2-methyl-1,3-thiazol-5-yl (Compound 4) or pyridyl (Compounds 8, 11, and 12) afforded higher % control remaining in both the erythroid and myeloid lineage. This same safety advantage was gained by replacing the 4-fluorophenyl group in pyrrolopyridine compounds (such as Comparator 3) with a 3-pyridyl group (Compound 8 and Compound 12). Installing a polar substituent on the pyrazole ring of the pyrrolopyrazole of Comparator 2 also generated an improved safety profile along with when an oxetan-3-yl substituent (Compound 1) was replaced a methyl in Comparator 2. A similar improvement in safety profile was achieved by exchanging a 4-fluorophenyl group for a 2,4-difluorophenyl group in the pyrrolopyrazole series. By, replacing the 4-fluorophenyl of Comparator 6 with a 2,4-difluorophenyl group, Compound 9 also realized an improved safety profile, particularly in the myeloid lineage.

TABLE 4

| Compound | Structure | Erythroid % control @ 10 uM dose | Myeloid % control @ 10 uM dose |
| --- | --- | --- | --- |
| Comparator 2 | 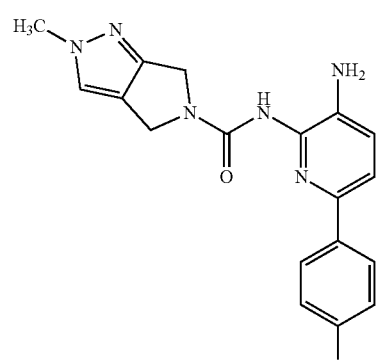 | 15.7 | 30.4 |
| 4 | 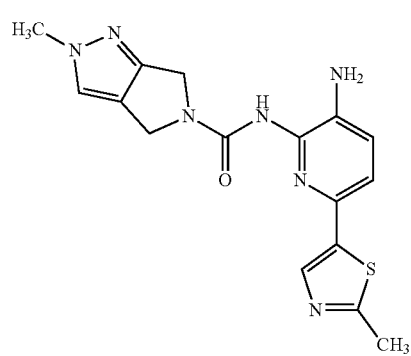 | 53 | 96 |

TABLE 4-continued

| Compound | Structure | Erythroid % control @ 10 uM dose | Myeloid % control @ 10 uM dose |
|---|---|---|---|
| 11 | 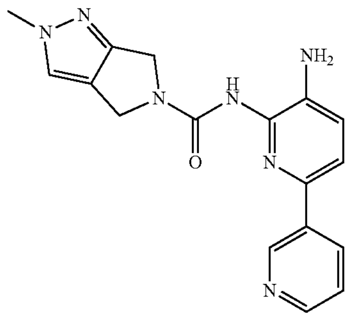 [SMILES: Cn1cc2c(n1)CN(C(=O)Nc1nc(-c3cccnc3)ccc1N)C2] | 94 | 103 |
| Comparator 6 | 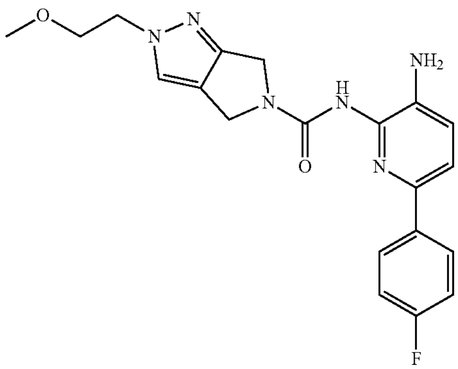 [SMILES: COCCn1cc2c(n1)CN(C(=O)Nc1nc(-c3ccc(F)cc3)ccc1N)C2] | 28 | 39 |
| 9 | 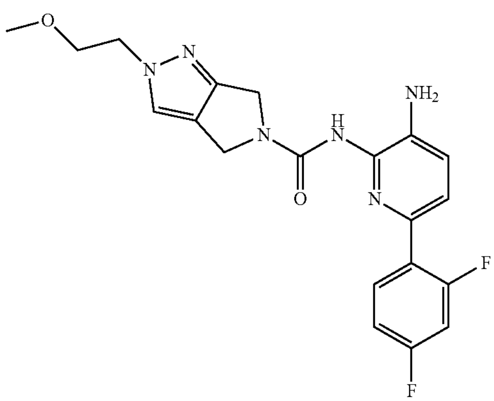 [SMILES: COCCn1cc2c(n1)CN(C(=O)Nc1nc(-c3ccc(F)cc3F)ccc1N)C2] | 40.4 | 62.8 |
| Comparator 3 | 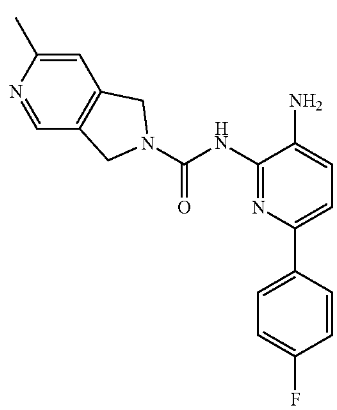 [SMILES: Cc1cc2c(cn1)CN(C(=O)Nc1nc(-c3ccc(F)cc3)ccc1N)C2] | 25.7 | 66.1 |

TABLE 4-continued

| Compound | Structure | Erythroid % control @ 10 uM dose | Myeloid % control @ 10 uM dose |
| --- | --- | --- | --- |
| 12 | 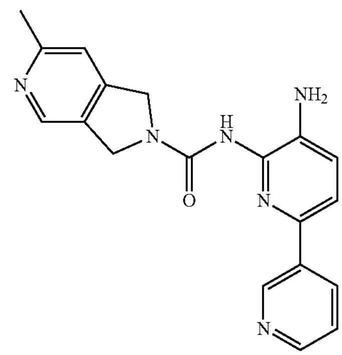 [SMILES: Cc1cc2c(cn1)CN(C(=O)Nc1nc(-c3cccnc3)ccc1N)C2] | 93 | 104 |
| 8 | 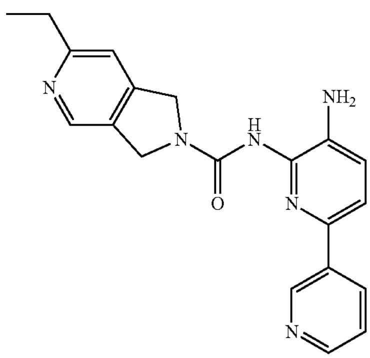 [SMILES: CCc1cc2c(cn1)CN(C(=O)Nc1nc(-c3cccnc3)ccc1N)C2] | 98 | 102 |
| Comparator 1 | 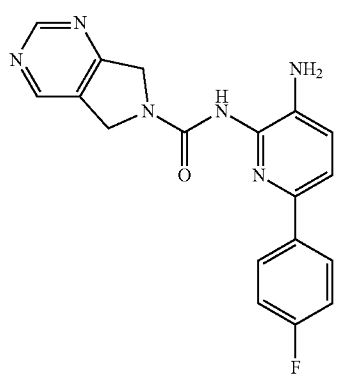 [SMILES: Nc1ccc(-c2ccc(F)cc2)nc1NC(=O)N1Cc2cncnc2C1] | 47.1 | 83.9 |
| 1 | 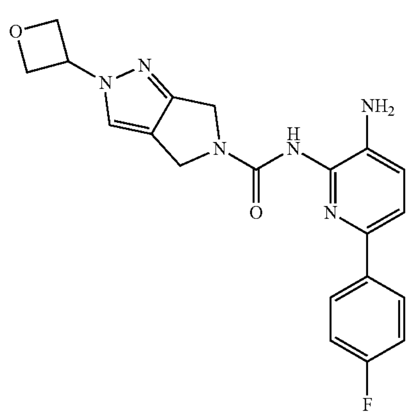 [SMILES: Nc1ccc(-c2ccc(F)cc2)nc1NC(=O)N1Cc2cn(C3COC3)nc2C1] | 37 | 54 |

TABLE 4-continued

| Compound | Structure | Erythroid % control @ 10 uM dose | Myeloid % control @ 10 uM dose |
| --- | --- | --- | --- |
| 14 | 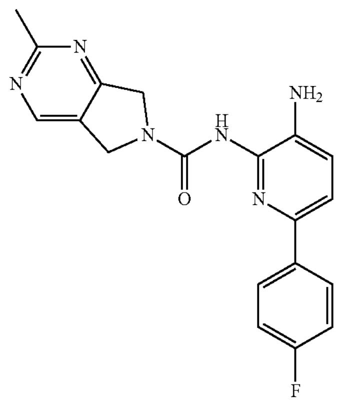 [SMILES: Cc1ncc2c(n1)CN(C(=O)Nc1nc(-c3ccc(F)cc3)ccc1N)C2] | 53 | 112 |
| 2 | 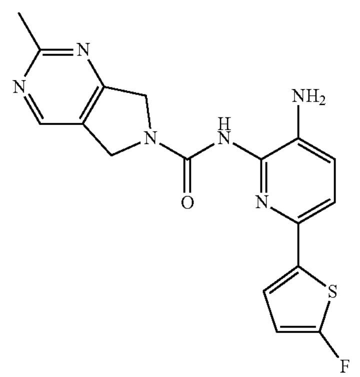 [SMILES: Cc1ncc2c(n1)CN(C(=O)Nc1nc(-c3ccc(F)s3)ccc1N)C2] | 40 | 87 |
| 3 | 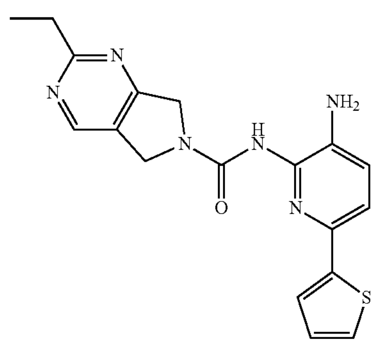 [SMILES: CCc1ncc2c(n1)CN(C(=O)Nc1nc(-c3cccs3)ccc1N)C2] | 46.6 | 89.4 |
| 17 | 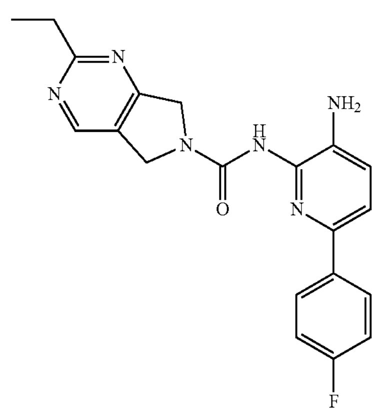 [SMILES: CCc1ncc2c(n1)CN(C(=O)Nc1nc(-c3ccc(F)cc3)ccc1N)C2] | 59.6 | 79.1 |

TABLE 4-continued

| Compound | Structure | Erythroid % control @ 10 uM dose | Myeloid % control @ 10 uM dose |
|---|---|---|---|
| Comparator 5 | 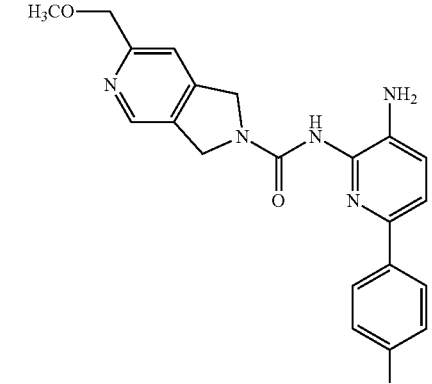 | 22.9 | 58.9 |

Assessment of Brain and Plasma Exposure for Rodin's Compounds Following Intravenous (IV) and Oral (PO) Administration to Mice Compounds were dosed in mice at either 10 mg/kg or 30 mg/kg PO, and were dosed at 1 mg/kg IV. Three animals for collection at each time point for plasma via bleeding at 0.25, 0.5, 1, 4, 12 and 24 h. Terminal bleeding for plasma and sampling for brain at 0.25, 0.5, 1, 4, 12 and 24 h (also three animals per brain exposure time point group). Total of six time points for plasma and six time points for brain.

Sample Collection:

Plasma: The animal was restrained manually at the designated time points, approximately 150 μL blood/time point was collected into $K_2$EDTA tube via retro orbital puncture or cardiac puncture under anesthesia with Isoflurane. The blood sample was centrifuged (2000 g, 4° C., 5 min) to generate plasma within 30 min after bleeding.

Brain: At the designated time points, a mid-line incision was made in the animals scalp and the skin was retracted. Using small bone cutters and rongeurs, removed the skull overlying the brain. Removed the brain using a spatula and rinse with cold saline. Placed the brain in screw-top tubes, and then stored the tubes under −70° C. until analysis. Results are shown in Table 5.

As shown from the data below, the addition of alkyl groups (ethyl or methyl) to the carbon position between the pyrimidine nitrogens (e.g., Compounds 2, 3, 14, and 17) led to increased half life (with both IV and PO dosing) and decreased clearance (IV), as well as improved brain exposure relative to unsubstituted counterparts (e.g., Comparator 1 and Comparator 6).

TABLE 5

| Compound | Structure | Brain Cmax @ 10 mpk ng/g (*scaled for comparison) | Projected free brain @ 10 mpk (uM) (*scaled for comparison) | IV PK $T_{1/2}$ (hr) | IV PK Cl (L/hr/kg) |
|---|---|---|---|---|---|
| Comparator 1 | 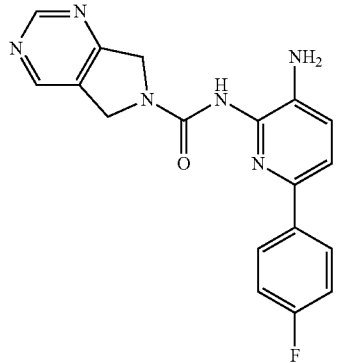 [SMILES: Nc1ccc(-c2ccc(F)cc2)nc1NC(=O)N1Cc2cncnc2C1] | 158* | 0.111* | Not available | Not available |

TABLE 5-continued

| Compound | Structure | Brain Cmax @ 10 mpk ng/g (*scaled for comparison) | Projected free brain @ 10 mpk (uM) (*scaled for comparison) | IV PK T$_{1/2}$ (hr) | IV PK Cl (L/hr/kg) |
|---|---|---|---|---|---|
| Comparator 6 | 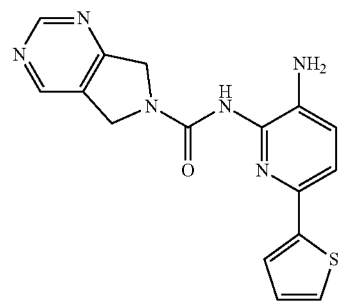 [SMILES: Nc1ccc(-c2cccs2)nc1NC(=O)N1Cc2cncnc2C1] | 100 | 0.103 | 0.152 PO = 0.557 | 8.33 |
| 14 | 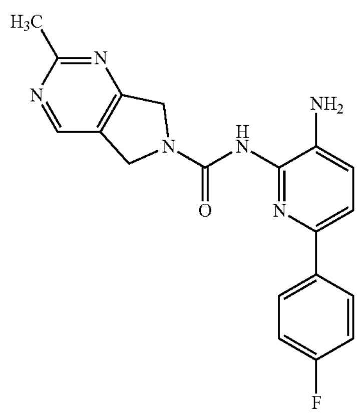 [SMILES: Cc1ncc2c(n1)CN(C(=O)Nc1nc(-c3ccc(F)cc3)ccc1N)C2] | 633 | 0.403 | 2.09 PO = 3.22 | 0.859 |
| 17 | 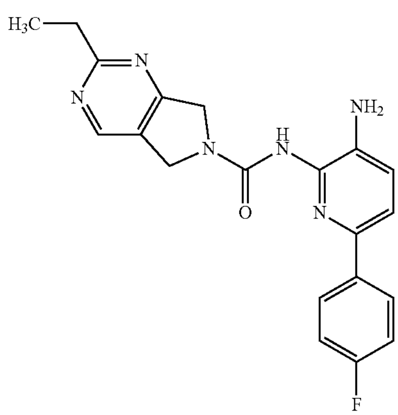 [SMILES: CCc1ncc2c(n1)CN(C(=O)Nc1nc(-c3ccc(F)cc3)ccc1N)C2] | 1241 | 0.568 | 2.07 PO = 2.54 | 1.49 |
| 3 | 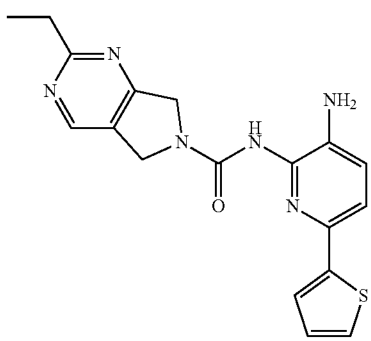 [SMILES: CCc1ncc2c(n1)CN(C(=O)Nc1nc(-c3cccs3)ccc1N)C2] | 526 | 0.387 | 0.737 PO = 1.48 | 1.50 |

TABLE 5-continued
| Compound | Structure | Brain Cmax @ 10 mpk ng/g (*scaled for comparison) | Projected free brain @ 10 mpk (uM) (*scaled for comparison) | IV PK T$_{1/2}$ (hr) | IV PK Cl (L/hr/kg) |
|---|---|---|---|---|---|
| 2 | 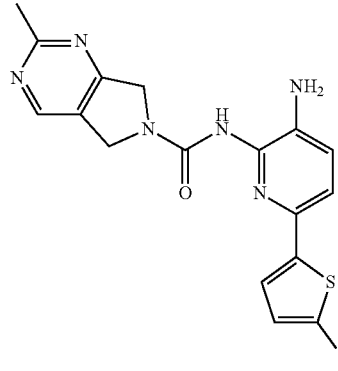 | 760 | 0.438 | 0.643<br>PO = 1.25 | 4.06 |
| 1 | 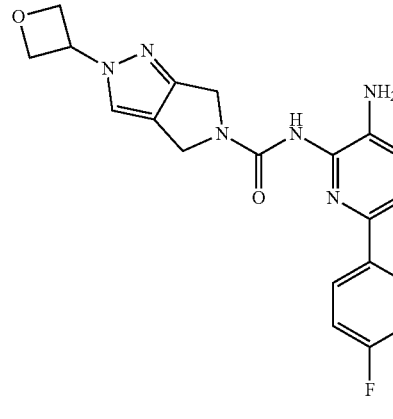 | 636 | 0.324 | 3.11<br>PO = 2.05 | 0.421 |
| 4 | 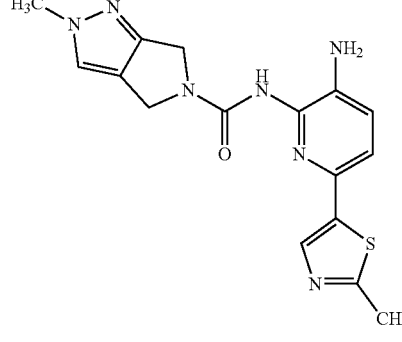 | 324 | 0.479 | 1.86<br>PO = 2.12 | 0.536 |
| 5 | 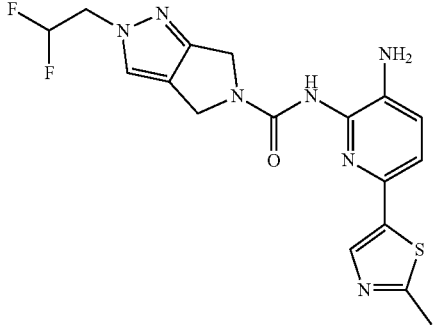 [SMILES: Cc1ncc(-c2ccc(N)c(NC(=O)N3Cc4cn(CC(F)F)nc4C3)n2)s1] | 277 | 0.302 | 2.81<br>PO = 2.33 | 0.354 |

TABLE 5-continued
| Compound | Structure | Brain Cmax @ 10 mpk ng/g (*scaled for comparison) | Projected free brain @ 10 mpk (uM) (*scaled for comparison) | IV PK $T_{1/2}$ (hr) | IV PK Cl (L/hr/kg) |
|---|---|---|---|---|---|
| 7 | 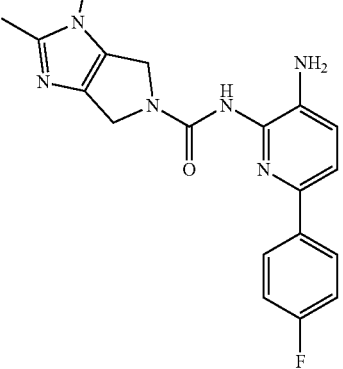 | 102 | 0.050 | 3.06<br>PO = 2.95 | 1.71 |
| 8 | 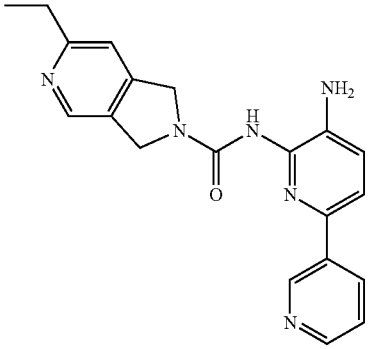 [SMILES: CCc1cc2c(cn1)CN(C(=O)Nc1nc(-c3cccnc3)ccc1N)C2] | 279 | 0.222 | 0.628<br>PO = 1.27 | 2.11 |
| 9 | 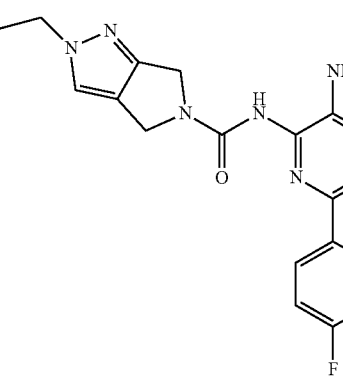 | 1533<br>1383 | 0.881<br>0.795 | 0.644<br>PO = 1.39,<br>1.01 | 1.67 |
| 11 | 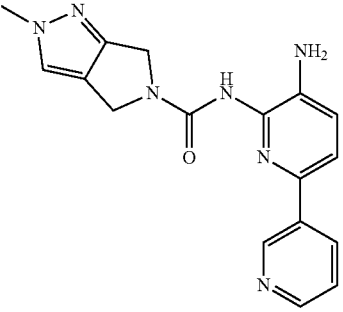 [SMILES: Cn1cc2c(n1)CN(C(=O)Nc1nc(-c3cccnc3)ccc1N)C2] | 369 | 0.664 | 7.53<br>PO = 2.90 | 1.07 |

TABLE 5-continued

| Compound | Structure | Brain Cmax @ 10 mpk ng/g (*scaled for comparison) | Projected free brain @ 10 mpk (uM) (*scaled for comparison) | IV PK $T_{1/2}$ (hr) | IV PK Cl (L/hr/kg) |
| --- | --- | --- | --- | --- | --- |
| 12 | 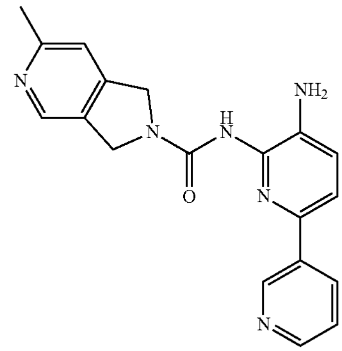 [SMILES: Cc1cc2c(cn1)CN(C(=O)Nc1nc(-c3cccnc3)ccc1N)C2] | 237 | 0.386 | 0.513 PO = 3.67 | 1.77 |

*Indicates compound dosed 30 mg/kg PO, and data has been scaled to compare to the 10 mg/kg PO data obtained for other compounds.

In Vitro Evaluation of Compounds on Human Megakaryocyte Progenitor CFC Proliferation in Normal Bone Marrow Compounds were tested to evaluate the potential effects on human megakaryocyte progenitor proliferation in the CFU-Mk assay. Clonogenic progenitors of the human megakaryocyte (CFU-Mk) lineage were assessed in a semi-solid, collagen-based matrix containing rhIL-3 (10 ng/mL), rhIL-6 (10 ng/mL) and rhTpo (50 ng/mL).

Cells

Normal human bone marrow light density cells (lot #0170525), derived from normal bone marrow (NorCal Biologics, California), were stored at −152° C. until required for the assay. On the day of the experiment, the cells were thawed rapidly, the contents of each vial was diluted in 10 mL of Iscove's modified Dulbecco's medium containing 10% fetal bovine serum (IMDM+10% FBS) and washed by centrifugation (approximately 1200 r.p.m. for 10 minutes, room temperature). The supernatant was discarded and the cell pellets resuspended in a known volume of IMDM+10% FBS. A cell count (3% glacial acetic acid) and viability assessment (trypan blue exclusion test) was performed for the bone marrow sample.

Compounds

All compounds were used as solutions in DMSO at 10 mM. Two different dosing paradigms were used depending on the study, either a six point dose response with top concentration of 20 µM, or a three point dose response with a top concentration of 10 µM. In six point dose response studies, compounds were tested at six distinct concentrations (20, 6.7, 2.2, 0.74, 0.25 and 0.082 µM), with serial dilutions prepared from the 10 mM stock concentration to achieve concentrations of 6.7, 2.2, 0.74, 0.25 and 0.082 mM. When added to the collagen-based media at 1:1000 (v/v), the final desired test concentrations were achieved. In order to generate the 20 µM final concentration, 8 µL of the 10 mM stock was added to the appropriately labeled tube. For the three point dose response studies, serial dilutions were prepared from the stock concentration to achieve concentrations of 2 and 0.4 mM. When added to the collagen-based media at 1:1000 (v/v), the final test concentrations of 10, 2 and 0.4 µM were achieved.

Method Summary

Clonogenic progenitors of the human megakaryocytic (CFU-Mk) lineages were set up in the media formulation described above. All compounds were added to the medium to give the final desired concentrations (20, 6.67. 2.22, 0.74, 0.25, and 0.082 µM). Solvent control cultures (containing no compound but 0.2% DMSO), as well as a standard control (containing no compound and no DMSO), were also initiated.

Human megakaryocyte progenitor assays were initiated with $1.8 \times 10^5$ cells per culture (lot #0170525). Following 14-16 days in culture, the cultures were transferred from the 35 mm dishes to labeled glass slides, were fixed (methanol/acetone) and then stained using an anti-human CD41 antibody and an alkaline phosphate detection system according to manufacturers' instructions. The colonies were assessed microscopically and scored by trained personnel and divided into the following categories based on size; CFU-Mk (3-20), CFU-Mk (21-49), CFU-Mk (≥50).

Statistical Analyses of CFC Numbers

The mean±1 standard deviation of three replicate cultures was calculated for the progenitors. Two-tailed standard t-tests were performed to assess if there was a difference in the number of colonies generated between solvent control and treated cultures. Due to the potential subjectivity of colony enumeration, a p value of less than 0.01 is deemed significant. To calculate the concentration of 50% inhibition of colony growth ($IC_{50}$) for each compound, a dose response curve was generated plotting the log of the compound concentration versus the percentage of control colony growth using Graphpad Prism 7.

Results

Megakaryocyte colony enumeration was performed by trained personnel. In addition, the distribution of colony types as well as general colony and cellular morphology was analyzed. The variance in colony number detected in replicate cultures was representative of the historical coefficient of variation for colony enumeration using these types of assays. The number and distribution of colonies detected in the solvent control (0.2% DMSO) was not significantly different from the standard control (containing no compound and no DMSO). For statistical analysis colony numbers in compound treated cultures were compared to the solvent control cultures. The megakaryocyte progenitor assay allows for the evaluation of more primitive progenitors, detected by the presence of large colonies (CFU-Mk≥50), the intermediate progenitors (CFU-Mk 21-49), detected by the presence of medium sized colonies, as well as the most mature progenitors (CFU-Mk 3-20), detected by the presence of small colonies. The total CFU-Mk value is the sum of the CFU-Mk (3-20), CFU-Mk (21-49) and CFU-Mk (≥50). $IC_{50}$ values are determined based on the total CFU-Mk.

Results are shown in Table 6 (IC50 shown for 6-point dose response; % control remaining @ 10 uM dose shown for 3-point dose response).

TABLE 6

| Compound | Structure | CFU-Mk Total IC50 (uM) | % Control CFU-Mk Total @ 10 uM dose |
|---|---|---|---|
| 2 | 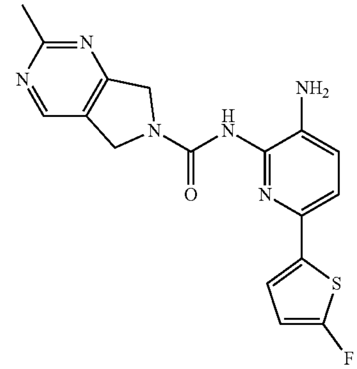 [SMILES: Cc1ncc2c(n1)CN(C(=O)Nc1nc(-c3ccc(F)s3)ccc1N)C2] | 2 | — |
| 3 | 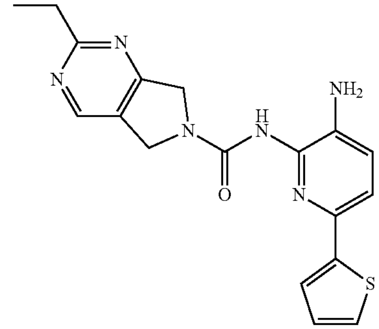 [SMILES: CCc1ncc2c(n1)CN(C(=O)Nc1nc(-c3cccs3)ccc1N)C2] | 2 | — |
| 5 | 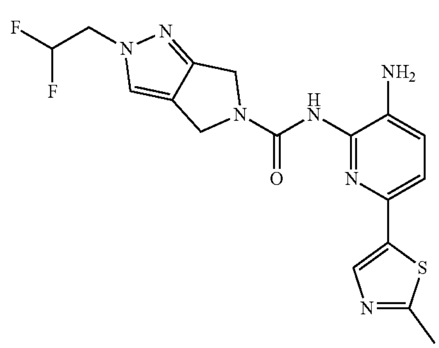 [SMILES: Cc1ncc(-c2ccc(N)c(NC(=O)N3Cc4cn(CC(F)F)nc4C3)n2)s1] | — | 36 |

TABLE 6-continued
| Compound | Structure | CFU-Mk Total IC50 (uM) | % Control CFU-Mk Total @ 10 uM dose |
|---|---|---|---|
| 9 | 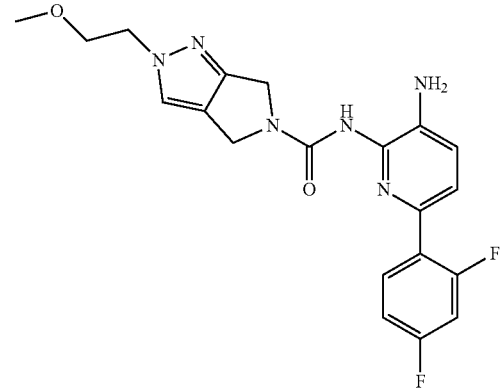 [SMILES: COCCn1cc2c(n1)CN(C(=O)Nc1nc(-c3ccc(F)cc3F)ccc1N)C2] | 10.8 | — |
| 12 | 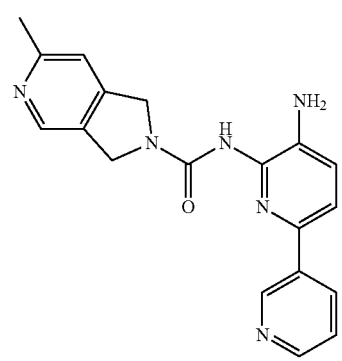 [SMILES: Cc1cc2c(cn1)CN(C(=O)Nc1nc(-c3cccnc3)ccc1N)C2] | >20 | — |
| 14 | 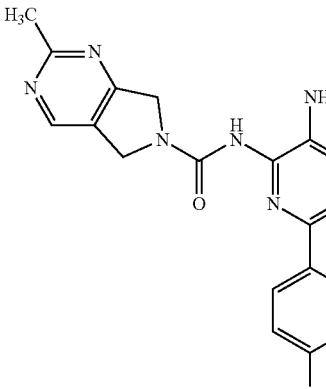 | — | 31 |

TABLE 6-continued

| Compound | Structure | CFU-Mk Total IC50 (uM) | % Control CFU-Mk Total @ 10 uM dose |
|---|---|---|---|
| 17 | 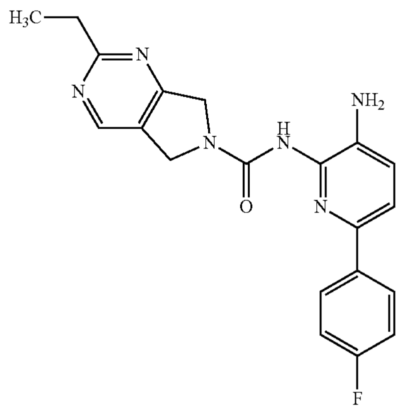 [SMILES: CCc1ncc2c(n1)CN(C(=O)Nc1nc(-c3ccc(F)cc3)ccc1N)C2] | — | 28 |

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:
1. A compound of the formula:

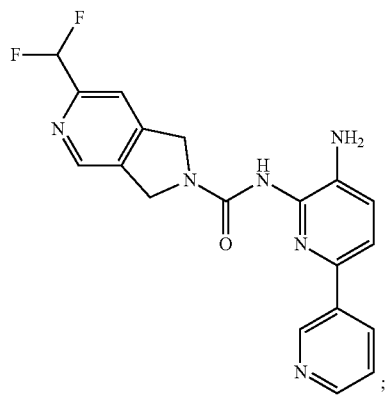

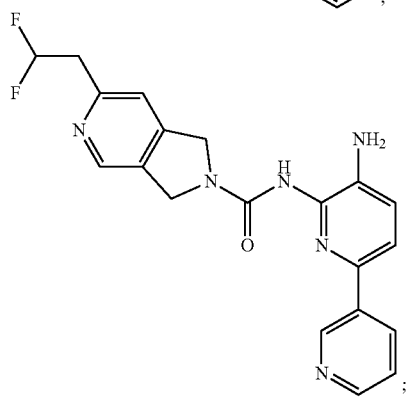

-continued

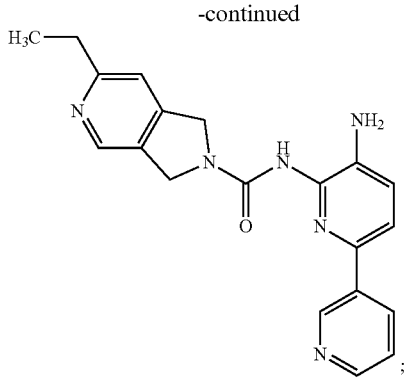

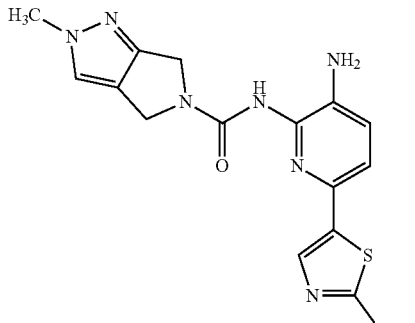

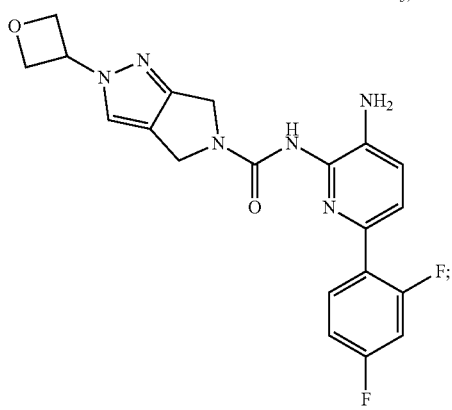

91
-continued
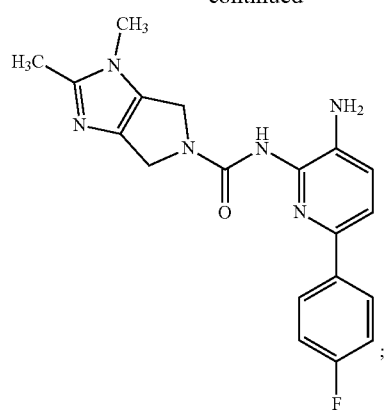
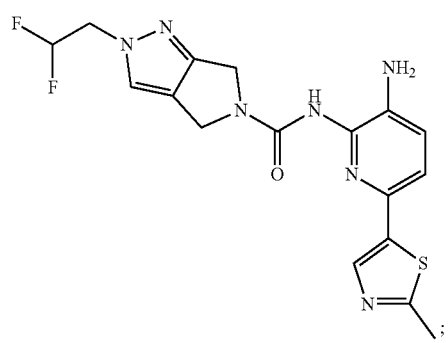
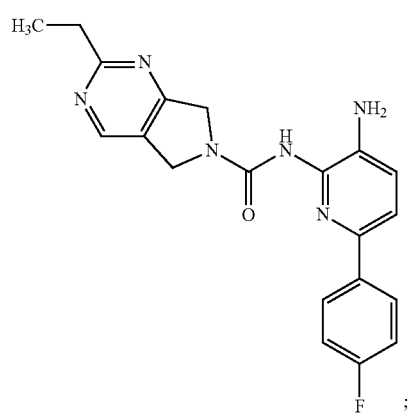
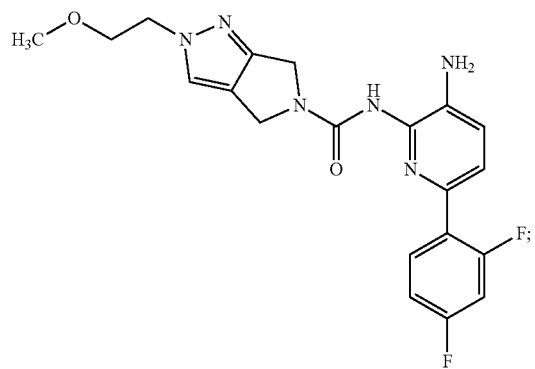
92
-continued
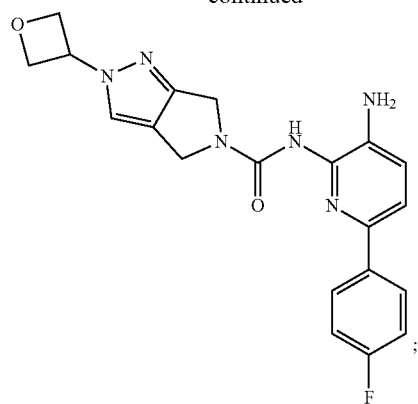
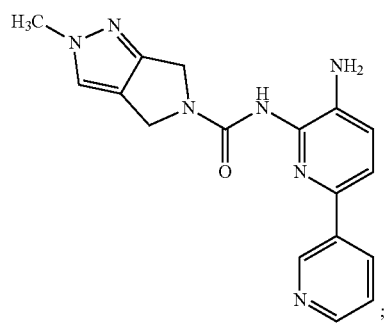
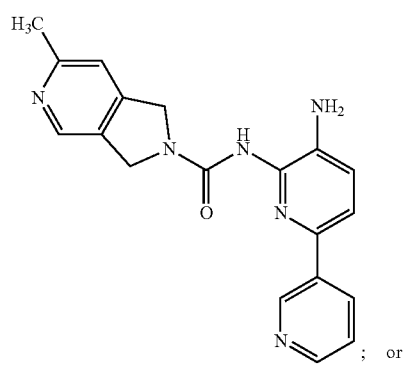
; or
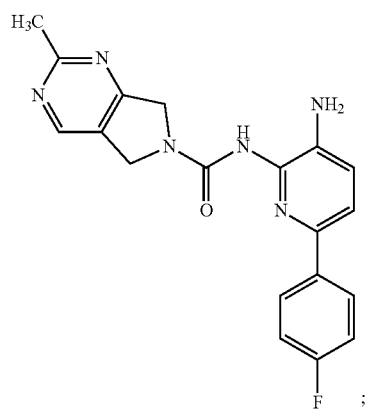
;
or a pharmaceutically acceptable salt thereof.

2. The compound of claim 1, wherein the compound is of the Formula:

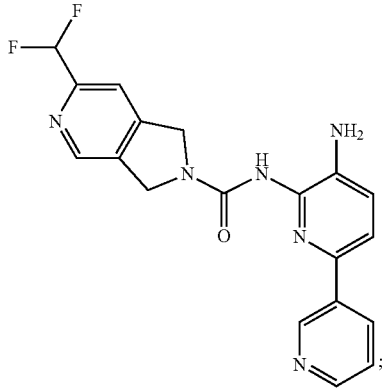 [SMILES: Nc1ccc(-c2cccnc2)nc1NC(=O)N1Cc2cnc(C(F)F)cc2C1]

or a pharmaceutically acceptable salt thereof.

3. The compound of claim 1, wherein the compound is of the Formula:

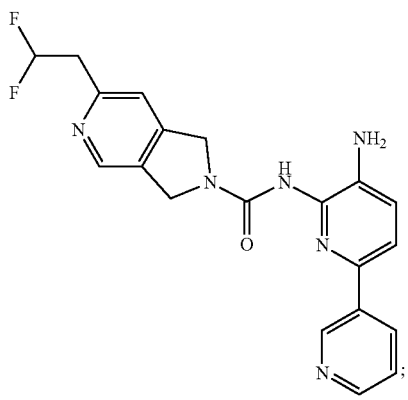 [SMILES: Nc1ccc(-c2cccnc2)nc1NC(=O)N1Cc2cnc(CC(F)F)cc2C1]

or a pharmaceutically acceptable salt thereof.

4. The compound of claim 1, wherein the compound is of the Formula:

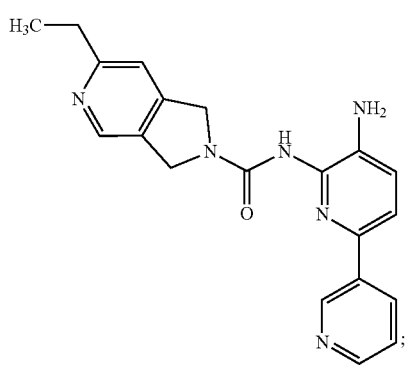 [SMILES: CCc1cc2c(cn1)CN(C(=O)Nc1nc(-c3cccnc3)ccc1N)C2]

or a pharmaceutically acceptable salt thereof.

5. The compound of claim 1, wherein the compound is of the Formula:

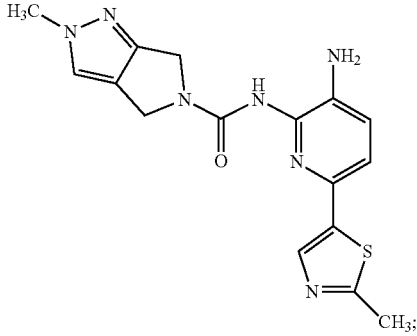 [SMILES: Cc1ncc(-c2ccc(N)c(NC(=O)N3Cc4cn(C)nc4C3)n2)s1]

or a pharmaceutically acceptable salt thereof.

6. The compound of claim 1, wherein the compound is of the Formula:

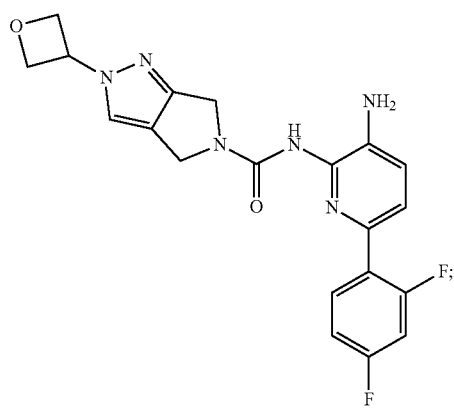 [SMILES: Nc1ccc(-c2ccc(F)cc2F)nc1NC(=O)N1Cc2cn(C3COC3)nc2C1]

or a pharmaceutically acceptable salt thereof.

7. The compound of claim 1, wherein the compound is of the Formula:

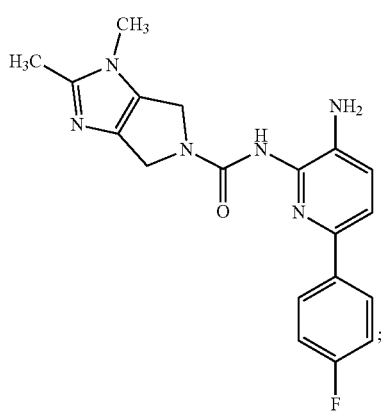 [SMILES: Cc1nc2c(n1C)CN(C(=O)Nc1nc(-c3ccc(F)cc3)ccc1N)C2]

or a pharmaceutically acceptable salt thereof.

8. The compound of claim 1, wherein the compound is of the Formula:

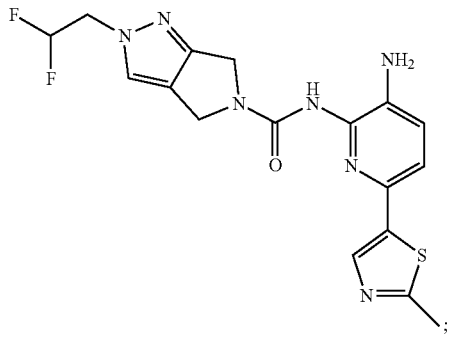 [SMILES: Cc1ncc(-c2ccc(N)c(NC(=O)N3Cc4cn(CC(F)F)nc4C3)n2)s1]

or a pharmaceutically acceptable salt thereof.

9. The compound of claim 1, wherein the compound is of the Formula:

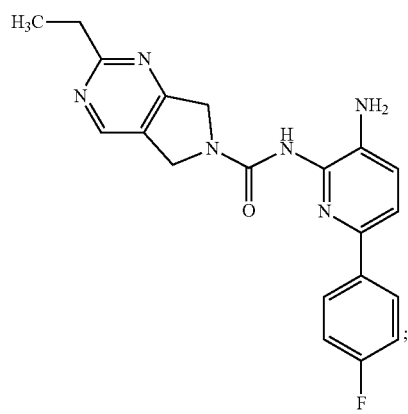 [SMILES: CCc1ncc2c(n1)CN(C(=O)Nc1nc(-c3ccc(F)cc3)ccc1N)C2]

or a pharmaceutically acceptable salt thereof.

10. The compound of claim 1, wherein the compound is of the Formula:

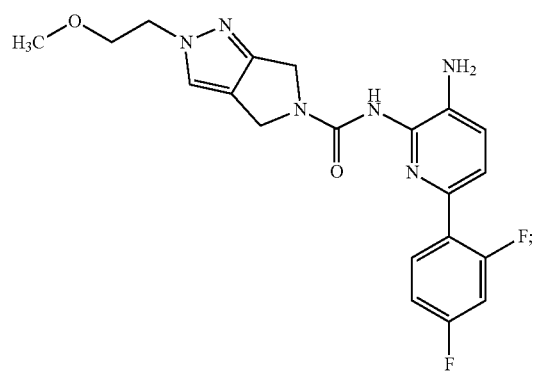 [SMILES: COCCn1cc2c(n1)CN(C(=O)Nc1nc(-c3ccc(F)cc3F)ccc1N)C2]

or a pharmaceutically acceptable salt thereof.

11. The compound of claim 1, wherein the compound is of the Formula:

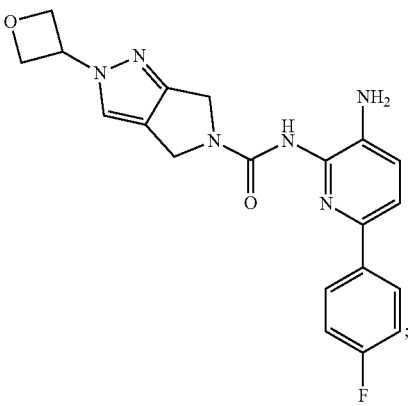 [SMILES: Nc1ccc(-c2ccc(F)cc2)nc1NC(=O)N1Cc2cn(C3COC3)nc2C1]

or a pharmaceutically acceptable salt thereof.

12. The compound of claim 1, wherein the compound is of the Formula:

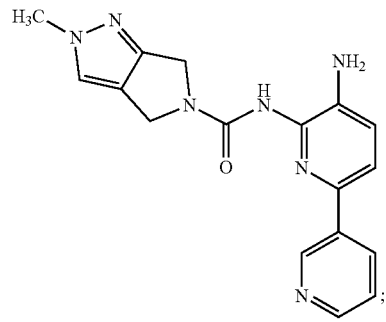 [SMILES: Cn1cc2c(n1)CN(C(=O)Nc1nc(-c3cccnc3)ccc1N)C2]

or a pharmaceutically acceptable salt thereof.

13. The compound of claim 1, wherein the compound is of the Formula:

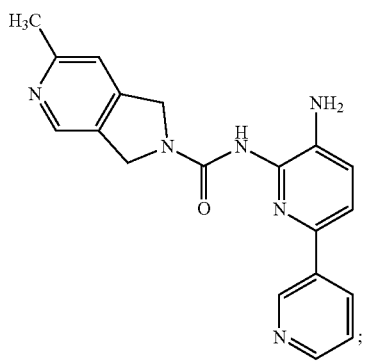 [SMILES: Cc1cc2c(cn1)CN(C(=O)Nc1nc(-c3cccnc3)ccc1N)C2]

or a pharmaceutically acceptable salt thereof.

14. The compound of claim 1, wherein the compound is of the Formula:

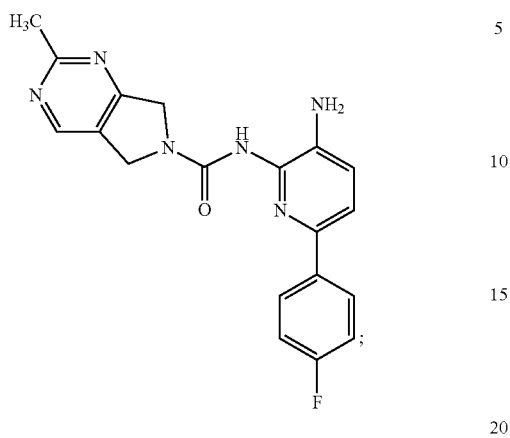

or a pharmaceutically acceptable salt thereof.

15. A composition comprising a compound of claim 1, or a pharmaceutically acceptable salt thereof; and a pharmaceutically acceptable carrier.

16. A method of inhibiting HDAC activity in a subject comprising the step of administering to the subject in need thereof an effective amount of a compound of claim 1, or a pharmaceutically acceptable salt thereof, or the composition of claim 15.

* * * * *